US011453886B2

(12) United States Patent
Muyldermans et al.

(10) Patent No.: US 11,453,886 B2
(45) Date of Patent: Sep. 27, 2022

(54) VIRUS-LIKE PARTICLES AND USES THEREOF

(71) Applicants: CENTRE NATIONAL DE LA RECHERCHE SCIENTIFIQUE, Paris (FR); UNIVERSITE DE STRASBOURG, Strasbourg (FR);

(Continued)

(72) Inventors: Serge Muyldermans, Hoeilaart (BE); Gérard Demangeat, Ostheim (FR); Ahmed Ghannam, Strasbourg (FR); Léa Ackerer, Vendenheim (FR); Caroline Hemmer, Colmar (FR); Christophe Ritzenthaler, Sélestat (FR); Vianney Poignavent, Strasbourg (FR)

(73) Assignees: CENTRE NATIONAL DE LA RECHERCHE SCIENTIFIQUE, Paris (FR); UNIVERSITE DE STRASBOURG, Strasbourg (FR);

(Continued)

( * ) Notice: Subject to any disclaimer, the term of this patent is extended or adjusted under 35 U.S.C. 154(b) by 0 days.

(21) Appl. No.: 16/492,619

(22) PCT Filed: Mar. 13, 2018

(86) PCT No.: PCT/EP2018/056256
§ 371 (c)(1),
(2) Date: Sep. 10, 2019

(87) PCT Pub. No.: WO2018/167070
PCT Pub. Date: Sep. 20, 2018

(65) Prior Publication Data
US 2020/0048649 A1 Feb. 13, 2020

(30) Foreign Application Priority Data
Mar. 13, 2017 (EP) ..................... 17305265

(51) Int. Cl.
C12N 7/00 (2006.01)
C12N 15/82 (2006.01)
C07K 16/10 (2006.01)

(52) U.S. Cl.
CPC .......... *C12N 15/8257* (2013.01); *C07K 16/10* (2013.01); *C07K 2317/569* (2013.01); *C12N 2770/32023* (2013.01)

(58) Field of Classification Search
None
See application file for complete search history.

(56) References Cited

U.S. PATENT DOCUMENTS 10,501,501 B2  12/2019  Belval et al.
2018/0265552 A1  9/2018  Belval et al.
2020/0040041 A1  2/2020  Belval et al.

FOREIGN PATENT DOCUMENTS

WO    WO 2015/110601    7/2015

OTHER PUBLICATIONS

Oliver et al., "Genetic structure and molecular variability of Grapevine fanleaf virus populations," Virus Research 152: 30-40 (Year: 2010).*

(Continued)

*Primary Examiner* — M Franco G Salvoza
(74) *Attorney, Agent, or Firm* — Saliwanchik, Lloyd & Eisenschenk

(57) ABSTRACT

The present invention relates to GFLV virus-like particles and the uses thereof in various fields, such as the pharmaceutical, agro, or veterinary areas.

12 Claims, 15 Drawing Sheets

Figure 1:
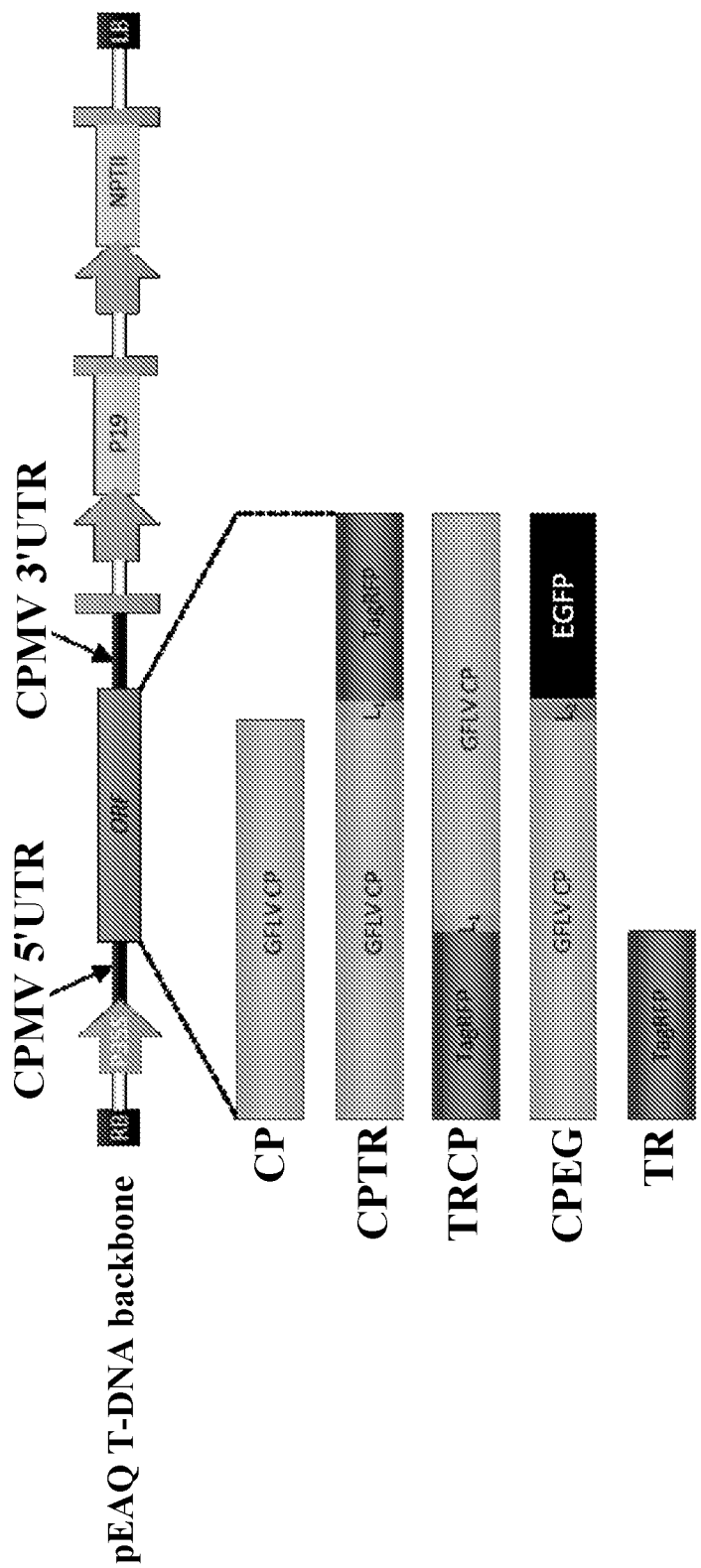

Specification includes a Sequence Listing.

(71) Applicants: INSTITUT NATIONAL DE LA RECHERCHE AGRONOMIQUE, Paris (FR); INSTITUT FRANCAIS DE LA VIGNE ET DU VIN, Le Grau du Roi (FR); VRIJE UNIVERSITEIT BRUSSEL, Brussels (BE)

(73) Assignees: INSTITUT NATIONAL DE LA RECHERCHE AGRONOMIQUE, Paris (FR); INSTITUT FRANCAIS DE LA VIGNE ET DU VIN, Le Grau du Roi (FR); VRIJE UNIVERSTEIT BRUSSEL, Brussels (BE)

(56) References Cited

OTHER PUBLICATIONS

Konterman et al., "Dual targeting strategies with bispecific antibodies," mAbs 4:2: 182-197 (Year: 2012).*

Noike et al., "Grapevine fanleaf virus (GFLV)-specific antibodies confer GFLV and Arabis mosaic virus (ArMV) resistance in Nicotiana benthamiana," Molecular Plant Pathology 10(1): 41-49 (Year: 2009).*

Hemmer et al., "Developpementet utilization de Nanobodies diriges contre le Grapevine fanleaf virus (GFLV) en lutte antivirale et comme biocapteur in planta," These Docteur, Universite De Strasbourg 1-184 (more legible copy) (Year: 2015).*

Belval, L. et al. "Display of whole proteins on inner and outer surfaces of grapevine fanleaf virus-like particles" *Plant Biotechnology Journal*, Jul. 29, 2016, pp. 2288-2299, vol. 14, No. 12.

Peyret, H. et al. "Tandem Fusion of Hepatitis B Core Antigen Allows Assembly of Virus-Like Particles in Bacteria and Plants with Enhanced Capacity to Accommodate Foreign Proteins" *PLOS ONE*, Apr. 1, 2015, pp. 1-20, vol. 10, No. 4.

Hemmer, C. et al. "Developpement et utilisation de Nanobodies diriges contre le *Grapevine fanleaf virus* (GFLV) en lutte antivirale et comme biocapteur in planta" *These Docteur, Universite De Strasbourg*, Jan. 1, 2015, pp. 1-184, retrieved from the Internet on Aug. 7, 2019: http://www.theses.fr/2015STRAJ085.pdf.

Written Opinion in International Application No. PCT/EP2018/056256, dated Jun. 8, 2018, pp. 1-7.

* cited by examiner

VIRUS-LIKE PARTICLES AND USES THEREOF

CROSS-REFERENCE TO RELATED APPLICATION

This application is the U.S. national stage application of International Patent Application No. PCT/EP2018/056256, filed Mar. 13, 2018.

The Sequence Listing for this application is labeled "Seq-List-replace.txt" which was created on Sep. 19, 2019 and is 94 KB. The entire content of the sequence listing is incorporated herein by reference in its entirety.

FIELD OF THE INVENTION

The present invention relates to virus-like particles and their uses in various fields such as the pharmaceutical, agrosciences, or veterinary areas.

BACKGROUND OF THE INVENTION

The use of virus-like particles ("VLPs") made from virus capsid-derived proteins and their use to deliver or expose antigens has been disclosed in the art.

For instance, VLPs have been made from animal viruses such as retroviruses or AAVs. Such VLPs, however, require complex structures and are not always convenient to produce.

VLPs derived from plant viruses have also been described. For instance, Sainsbury et al. (Annual Review of Phytopathology 2010 48:437-455) reports the production of VLPs from Cowpea Mosaic virus. Such constructs, however, require co-expression and assembly of two distinct subunits (L and S) or expression of a precursor polypeptide and a protease, rendering resulting VLPs difficult to correctly fold and produce.

Denis et al. (Virology 363 (2007) 59-68) have used the capsid protein of Papaya mosaic virus to expose short HCV viral epitopes. Similarly, Natilla and Hammond (Journal of Virological Methods 178 (2011) 209-215) have prepared VLPs from a capsid protein of a Maize Rayado Fino virus conjugated to a short (8 amino acids) peptide. Other examples were reported with Tobacco mosaic virus (examples) Tomato Bushy stunt virus (Kumar et al. 2009, Virology 388, 185-190), Potato virus Y (Kalnciema et al 2012 Molecular Biotechnology 52 2,129) or Artichoke mottle crinkle virus (Arcangeli et al, Journal of Biomolecular Structure and Dynamics Volume 32, Issue 4, 2014).

In each of these constructs, however, the resulting VLPs allowed coupling of generally only small molecules, and/or required assembly of distinct sub-units, and/or allowed only exposure of a peptide to the exterior of the VLP and/or generated large filamentous rather than icosahedral VLP structures comprising or not nucleic acids.

The present invention provides improved VLPs derived from Grapevine fanleaf virus (GFLV), having improved and unexpected properties.

SUMMARY OF THE INVENTION

The present invention relates to VLPs derived from GFLV coat proteins and the uses thereof. In a first aspect, the present invention shows that the coat protein of GFLV may be used to produce stable VLPs. The invention further shows that GFLV coat protein is a very versatile protein which allows the genetic fusion of large foreign compounds to the N- and/or C-terminal thereof without losing its ability to form VLPs. In addition, the present invention shows that the genetic fusion of a compound the N-terminal leads to its internalization into the VLPs, making the compound inaccessible to antibodies ("caging"). It is therefore possible to produce VLPs having two distinct properties: the surface exposure and/or the protection by internalization (caging) of compounds of interest. Moreover, the VLPs are produced from the self-assembly of a single type of coat protein, are quite small in size (approx. 30 nm outer diameter) and simple in structure and nucleic acid-free. Also and advantageously, the coat proteins of GFLV may be fused to very large proteins (above 200 amino acids) without losing their ability to assemble into VLPs. To our knowledge, no single viral protein has been described in the art having all of these properties simultaneously.

In a second aspect, the present invention shows that VLPs derived from GFLV coat proteins can be simultaneously conjugated to two or three different types of anti-GFLV coat protein antibodies or antibody derivatives, said antibodies or antibody derivatives being attached to large proteins. For instance, the VLPs can be conjugated to up to 60 anti-GFLV coat protein antibodies or antibody derivatives by particle for each type of antibodies or antibody derivatives. Accordingly, with three different antibodies, the VLP can bear up to 180 antibodies.

Accordingly, the present invention relates to a virus-like particle comprising a Grapevine fanleaf virus (GFLV) coat protein and at least two different anti-GFLV coat protein antibodies or antibody derivatives. Preferably, the at least two different anti-GFLV coat protein antibodies or antibody derivatives do not compete with each other for the binding to the GFLV coat protein. Optionally, the particle comprises at least three different anti-GFLV coat protein antibodies or antibody derivatives, preferably in which the at least three different anti-GFLV coat protein antibodies or antibody derivatives do not compete with each other for the binding to the GFLV coat protein. In one embodiment, the antibody derivative is a ScFv derived from conventional immunoglobulins or a Nanobody or VHH derived from heavy-chain only immunoglobulins found in Camelids.

In a preferred embodiment, one, two or three of the at least two or three different anti-GFLV coat protein antibodies or antibody derivatives comprise the sequences of a set of CDR 1, CDR 2 and CDR 3 from one of the following groups:

| Group | CDR1 SEQ ID NO: | CDR2 SEQ ID NO: | CDR3 SEQ ID NO: | Nanobody |
|---|---|---|---|---|
| I | 34 | 35 | 36 | 23 |
|  | 37 | 38 | 39 | p75 |
|  | 40 | 41 | 42 | 101 |
|  | 43 | 44 | 45 | 126 |
|  | 46 | 47 | 48 | p71 |
| II | 49 | 50 | 51 | p59 |
|  | 52 | 53 | 54 | 125 |
|  | 55 | 56 | 57 | 155 |
|  | 58 | 59 | 60 | 37 |
|  | 61 | 62 | 63 | 77 |
|  | 64 | 65 | 66 | 171 |
|  | 67 | 68 | 69 | 159 |
|  | 70 | 71 | 72 | p25 |
|  | 73 | 74 | 75 | 172 |
| III | 76 | 77 | 78 | 122 |
| IV | 79 | 80 | 81 | 15 |
|  | 82 | 83 | 84 | p77 |

-continued

| Group | CDR1 SEQ ID NO: | CDR2 SEQ ID NO: | CDR3 SEQ ID NO: | Nanobody |
|---|---|---|---|---|
| V | 85 | 86 | 87 | 34 |
|   | 88 | 89 | 90 | 80 |
| VI | 91 | 92 | 93 | 38 |
| VII | 94 | 95 | 96 | 137 |
| VIII | 97 | 98 | 99 | 139 |
| IX | 100 | 101 | 102 | p12 |

In a more specific embodiment, one, two or three of the at least two or three different anti-GFLV coat protein antibodies or antibody derivatives comprise a sequence from one of the following groups:

| Group | SEQ ID NO: | Nanobody (Nb) |
|---|---|---|
| I | 9 | 23 |
|   | 10 | p75 |
|   | 8 | 101 |
|   | 7 | 126 |
|   | 11 | p71 |
| II | 12 | p59 |
|   | 13 | 125 |
|   | 14 | 155 |
|   | 15 | 37 |
|   | 16 | 77 |
|   | 17 | 171 |
|   | 18 | 159 |
|   | 19 | p25 |
|   | 20 | 172 |
| III | 21 | 122 |
| IV | 22 | 15 |
|   | 23 | p77 |
| V | 24 | 34 |
|   | 25 | 80 |
| VI | 26 | 38 |
| VII | 27 | 137 |
| VIII | 28 | 139 |
| IX | 29 | p12 |

Preferably, the at least two or three different anti-GFLV coat protein antibodies or antibody derivatives are each selected in a different group among groups I to IX, more preferably among Groups I, II and III.

In one embodiment,
a first anti-GFLV coat protein antibody or antibody derivative is selected from Group I, a second anti-GFLV coat protein antibody or antibody derivative is selected from Group II and optionally a third anti-GFLV coat protein antibody or antibody derivative is selected from Group III; or
a first anti-GFLV coat protein antibody or antibody derivative is selected from Group I, a second anti-GFLV coat protein antibody or antibody derivative is selected from Group III and optionally a third anti-GFLV coat protein antibody or antibody derivative is selected from Group II; or
a first anti-GFLV coat protein antibody or antibody derivative is selected from Group II, a second anti-GFLV coat protein antibody or antibody derivative is selected from Group III and optionally a third anti-GFLV coat protein antibody or antibody derivative is selected from Group I.

In a more specific embodiment,
a first anti-GFLV coat protein antibody or antibody derivative is selected from the group consisting of Nb23 and Nbp75, a second anti-GFLV coat protein antibody or antibody derivative is selected from the group consisting of Nbp59, Nb125 and Nb155, and optionally a third anti-GFLV coat protein antibody or antibody derivative is Nb122; or
a first anti-GFLV coat protein antibody or antibody derivative is selected from the group consisting of Nb23 and Nbp75, a second anti-GFLV coat protein antibody or antibody derivative is Nb122 and optionally a third anti-GFLV coat protein antibody or antibody derivative is selected from the group consisting of Nbp59, Nb125 and Nb155; or
a first anti-GFLV coat protein antibody or antibody derivative is selected from the group consisting of Nbp59, Nb125 and Nb155, a second anti-GFLV coat protein antibody or antibody derivative is Nb122, and optionally a third anti-GFLV coat protein antibody or antibody derivative is selected from the group consisting of Nb23 and Nbp75.

Preferably, the at least two or three different anti-GFLV coat protein antibodies or antibody derivatives are conjugated to a compound, preferably a different compound for each anti-GFLV coat protein antibody or antibody derivative.

Optionally, the GFLV coat protein is conjugated to a compound by covalent coupling in N-terminal of the GFLV coat protein.

In a particular embodiment, the GFLV coat protein comprises SEQ ID NO: 1, or a sequence having at least 80% identity to SEQ ID NO: 1, preferably at least 90%.

The compound can be a therapeutic, diagnostic or imaging agent or a tag, preferably a polypeptide or a peptide. Conjugation to the compound may be covalent (e.g., through genetic fusion or chemical coupling) and/or non-covalent (e.g., through ligand mediated binding).

The present invention also relates to a pharmaceutical composition comprising one or more virus-like particles of the present invention.

The present invention further relates to a method of producing virus-like particles of the present invention, comprising (i) providing a GFLV coat protein, optionally conjugated to a compound, (ii) allowing said GFLV coat protein, alone or in mixture with other proteins, to form virus-like particles, and (iii) coupling the particles of (ii) to at least two different anti-GFLV coat protein antibodies or antibody derivatives as disclosed in the present document.

In addition, the present invention relates to a composition comprising at least two or three different anti-GFLV coat protein antibodies or antibody derivatives as disclosed in the present document. Preferably, the at least two or three different anti-GFLV coat protein antibodies or antibody derivatives are conjugated to a compound, preferably a different compound for each anti-GFLV coat protein antibody or antibody derivative.

The present invention relates to the use of a composition comprising at least two or three different anti-GFLV coat protein antibodies or antibody derivatives as defined herein to make GFLV virus-like particles simultaneously conjugated to two or three different types of anti-GFLV coat protein antibodies or antibody derivatives.

The present invention also relates to the use of a GFLV VLP conjugated to two or three different types of anti-GFLV coat protein antibodies or antibody derivatives to deliver a compound to a subject.

The invention has wide utility in the pharmaceutical industry, to produce e.g., vaccines, adjuvants, drugs or imaging agents, for instance, for human or veterinary applications, as well as for research uses.

LEGEND TO THE FIGURES

FIG. 1: Schematic representation of pEAQ vector T-DNA region and constructs derived thereof. The backbone of the T-DNA region, extending from the right border (RB) to the left border (LB), is represented in grey shades. Open reading frame (ORF) of interest is flanked by sequences of Cowpea mosaic virus untranslated regions (CPMV UTRs) under control of Cauliflower mosaic virus 35S promoter (P35S). Native Grapevine fanleaf virus (GFLV) coat protein (CP) as well as its TagRFP- and EGFP-tagged variants were introduced by Gateway cloning as schematically indicated. L1 corresponds to the 7-amino-acid $Gly_3$-Ser-$Gly_3$ linker sequence. $L_2$ corresponds to the 15-amino-acid linker sequence resulting from Gateway recombination. Complete amino-acid-sequences of the expressed proteins are provided at the end of the document (sequence). P19: Tombusvirus P19 silencing suppressor. NPTII: neomycin phosphotransferase II gene.

Figure 2:
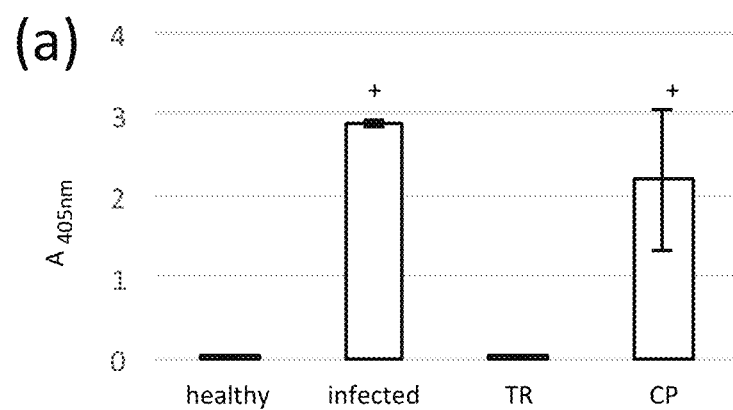
Figure 2:
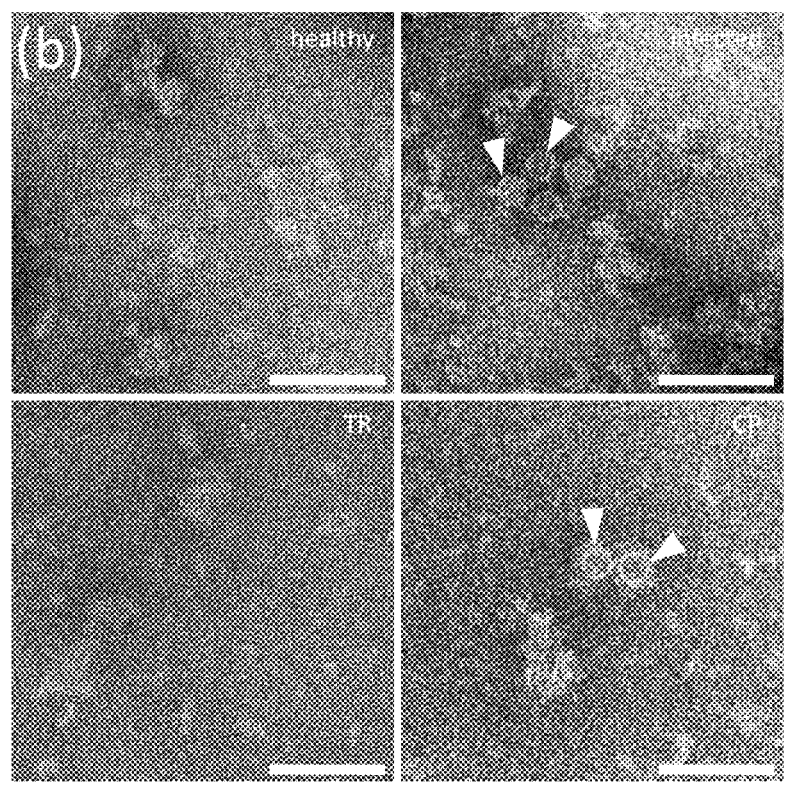

FIG. 2: Transient expression of GFLV CP in $N.$ $benthamiana$ leaves leads to VLP production. (a) Expression of GFLV CP in $N.$ $benthamiana$ leaves at 7 days post-agroinfiltration or at 14 days post-infection was determined by DAS-ELISA using anti-GFLV antibodies for detection and para-nitrophenylphosphate as substrate for alkaline phosphatase. Bars represent the mean absorbance obtained with three different leaves for each condition. Error-bars correspond to 95% confidence intervals. Samples were considered positive (+) when $O.D._{405nm}$ exceeded the healthy control sample mean value by at least a factor of three. (b) ISEM micrographs resulting from observations performed on the same extracts than analyzed by DAS-ELISA. Approximately 30 nm particles (arrowheads) were detected only in GFLV-infected and CP expressing samples. Scale bars: 100 nm.

Figure 3:
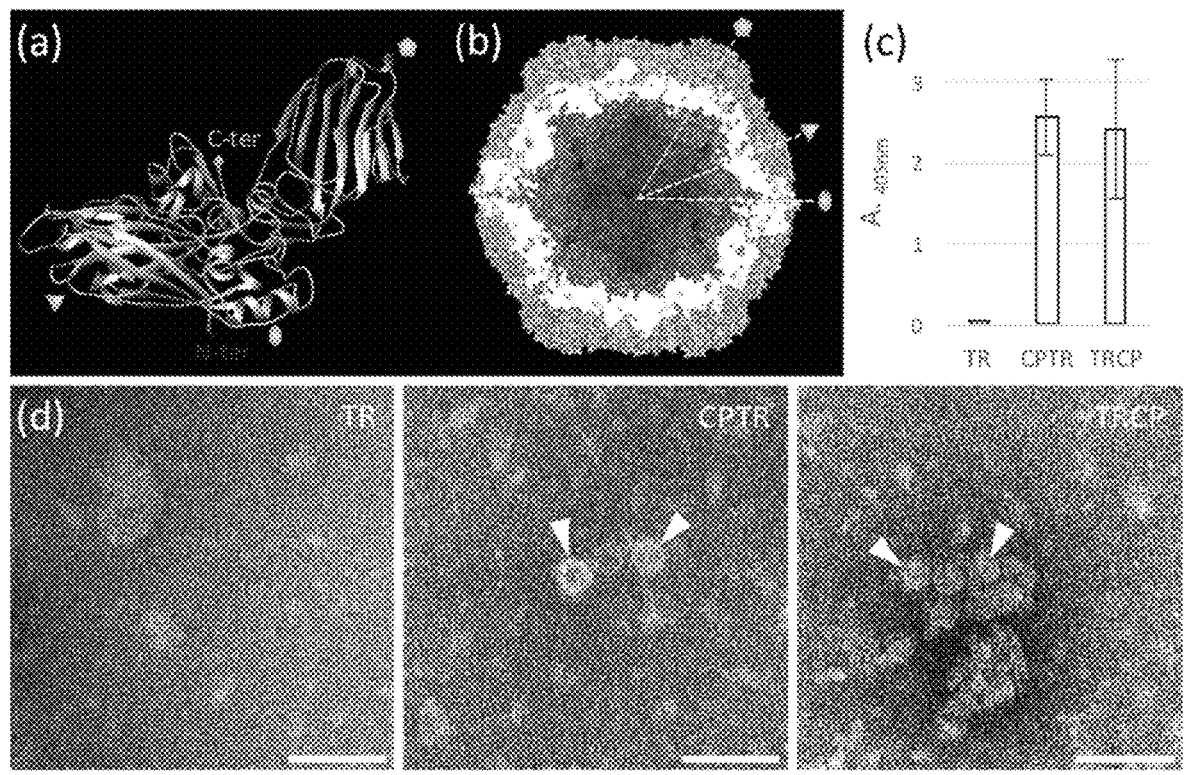

FIG. 3: Fusion of TagRFP (TR) to the N- or C-terminal ends of GFLV CP is compatible with VLP formation. (a) Ribbon diagram view of a GFLV CP subunit and (b) surface-shaded cross-section of a particle according to the 3 Å resolution atomic structure (PDB code 4V5T, Schellenberger et al., 2011). Positions of the CP N- and C-termini are indicated in dark grey and light grey, respectively. The pentagon, triangle and oval symbolize the icosahedral 5-fold, 3-fold and 2-fold icosahedral symmetry axes, respectively. Residues in the cross-section plane appear in white. (c) Expression of GFLV CP in $N.$ $benthamiana$ crude leaf extracts 7 days after agro-infiltration with TR, CPTR or TRCP. DAS-ELISA was performed using anti-GFLV antibodies and sample considered positive (+) when $O.D._{405\,nm}$ value exceeded the healthy control sample mean value by at least a factor of three. Bars represent the mean absorbance obtained with three different leaves for each condition. Error-bars correspond to 95% confidence intervals (d) ISEM micrographs resulting from observations performed on the same extracts than analysed by DAS-ELISA. Arrowheads point to VLPs trapped by anti-GFLV antibodies in CPTR and TRCP clarified leaf extracts. Scale bars: 100 nm.

Figure 4:
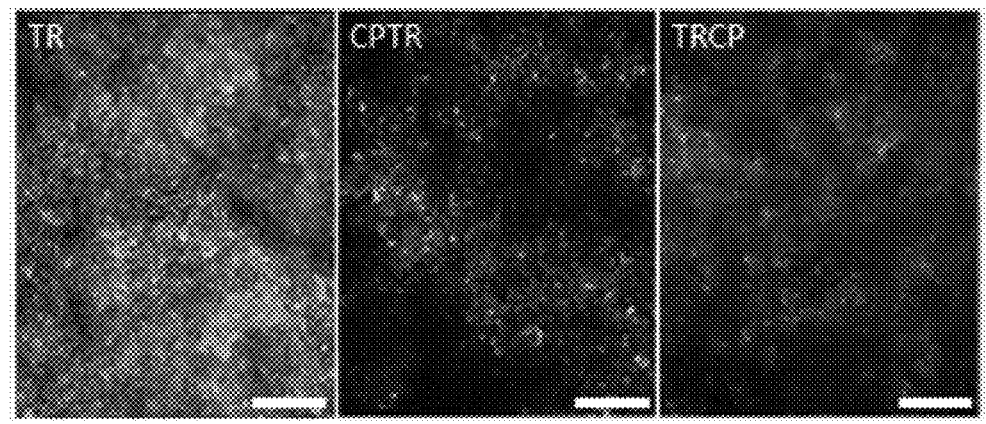

FIG. 4: Epifluorescence macroscopy images of agro-infiltrated $Nicotiana$ $benthamiana$ leaves expressing TR, CPTR or TRCP. Filters used for excitation and emission are as follow: $\lambda_{ex}625$-655- of $\lambda_{em665}$-715 nm. Scale bars: 300 µm.

Figure 5:
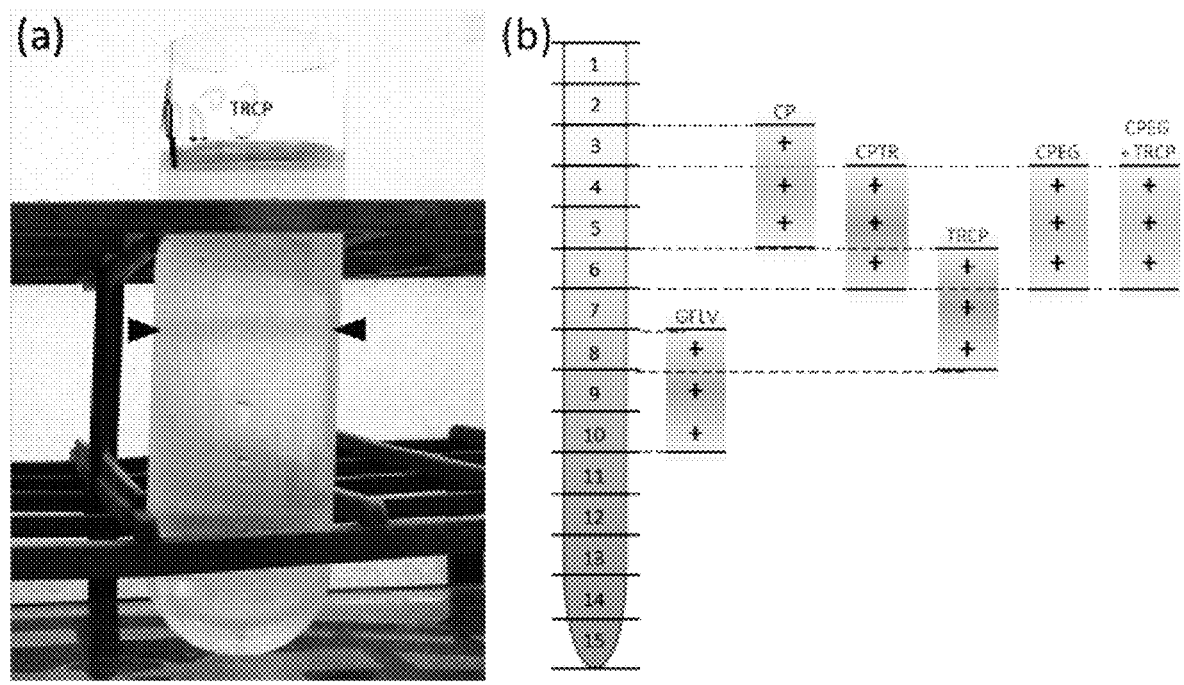

FIG. 5: Additional information concerning the purification of VLPs. (a) Bright pink band in light grey on the figure) after linear sucrose gradient centrifugation of TRCP VLPs (b) Schematic representation of the location of virus- and VLP-enriched fractions in linear sucrose gradients. The collected 2 mL fractions are numbered from 1 (top of the gradient) to 15 (bottom). RNA-containing virions were localized measuring the $O.D._{260}$ values of the different fractions. VLPs-enriched fractions were identified by semi-quantitative ELISA.

Figure 6:
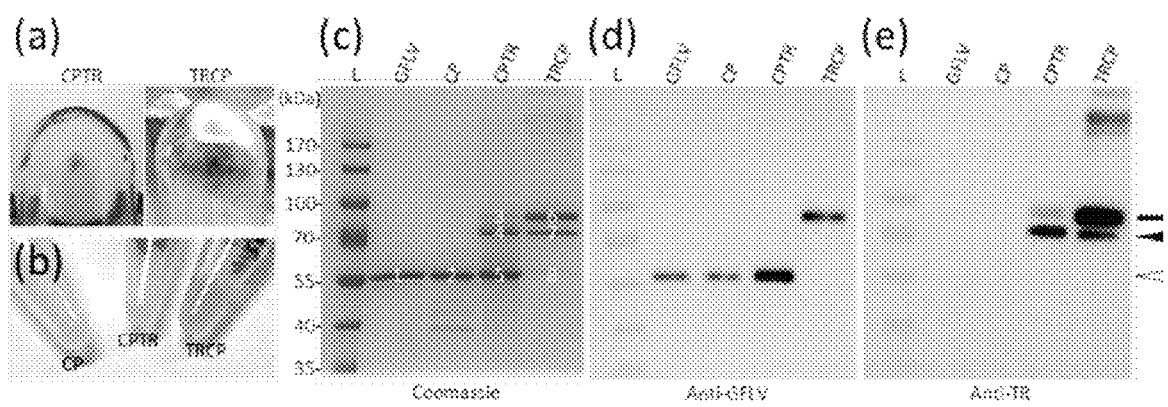

FIG. 6: Recombinant VLPs can be purified from CP, CPTR and TRCP expressing leaves. (a) Pink pellets (in dark grey on the figure) resulting from CPTR (left panel) and TRCP (right panel) purifications at final ultracentrifugation stage. (b) Purified CP, CPTR and TRCP in solution. Note the pink colour of CPTR and TRCP samples (in dark grey on the figure). (c) Coomassie-blue stained gel of GFLV, CP, CPTR and TRCP purified particles after SDS-Page. 6 µg of GFLV-particles equivalent were separated in each lane. Major bands in the gel are numbered from 1 to 8. (d and e) Corresponding western blotting analyses of GFLV, CP, CPTR and TRCP samples using anti-GFLV (d) or anti-TagRFP (TR, e) antibodies. 0.05 µg of GFLV-particles equivalent were used in each lane. White arrowhead indicates bands with expected size for CP. Arrow points to bands with expected size for full-length TRCP and CPTR fusions, respectively. Black arrowhead points to major TRCP or CPTR truncated products. L: molecular mass markers. Mass (kDa) are indicated to the left.

Figure 7:
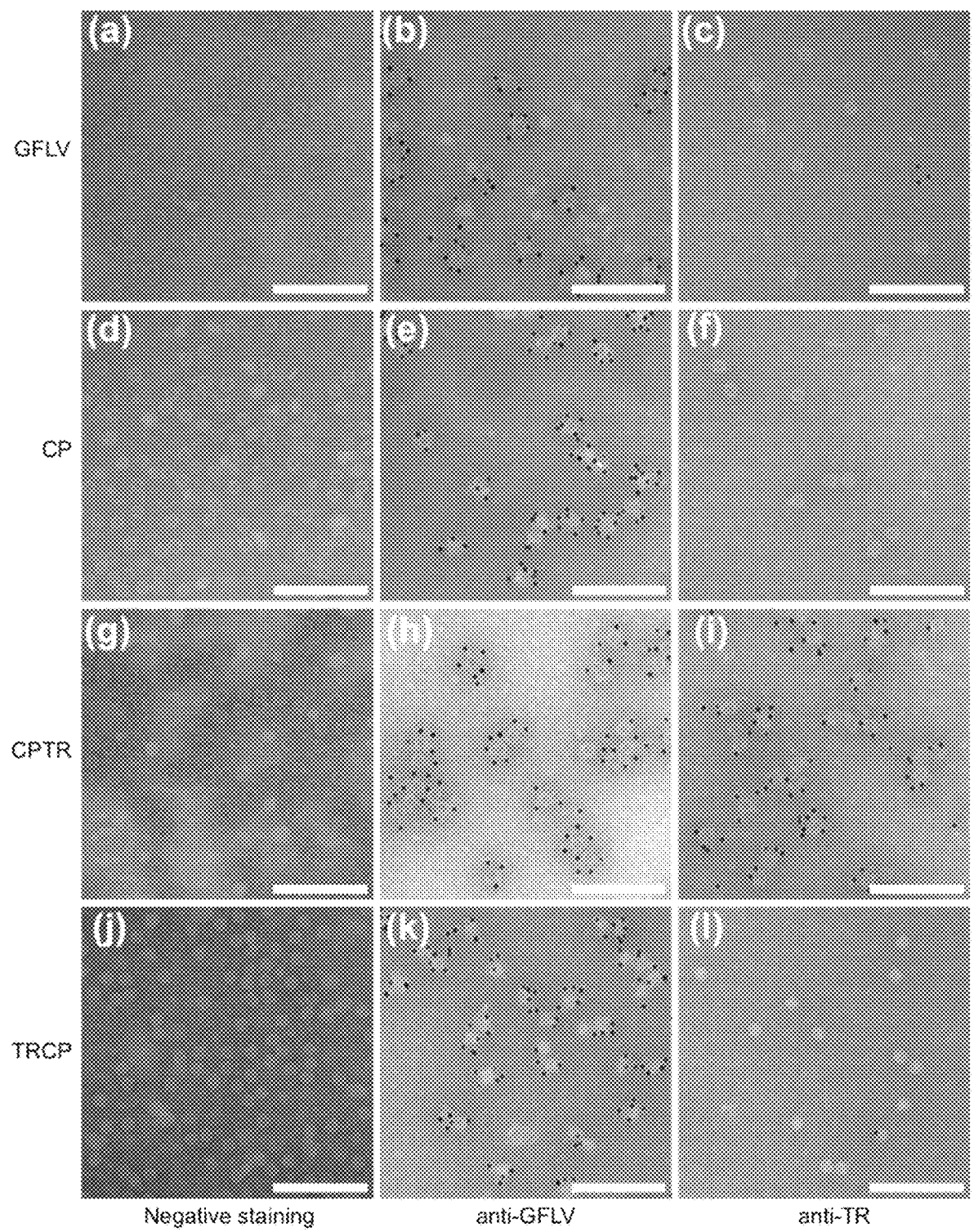

FIG. 7: Protein fused to the N- or C-terminal end of GFLV CPs are encaged or exposed to the outer surface of VLPs, respectively. Electron micrographs of purified GFLV (a, b, c), CP VLPs (d, e, f), CPTR VLPs (g, h, i) and TRCP VLPs (j, k, l). Samples were processed for negative staining only (a, d, g, j) or for ISEM using anti-GFLV (b, e, h, k) or anti-TR (c, f, i, l) antibodies and anti-rabbit antibodies conjugated to 10 nm colloidal gold particles for decoration. Scale bars: 200 nm.

Figure 8:
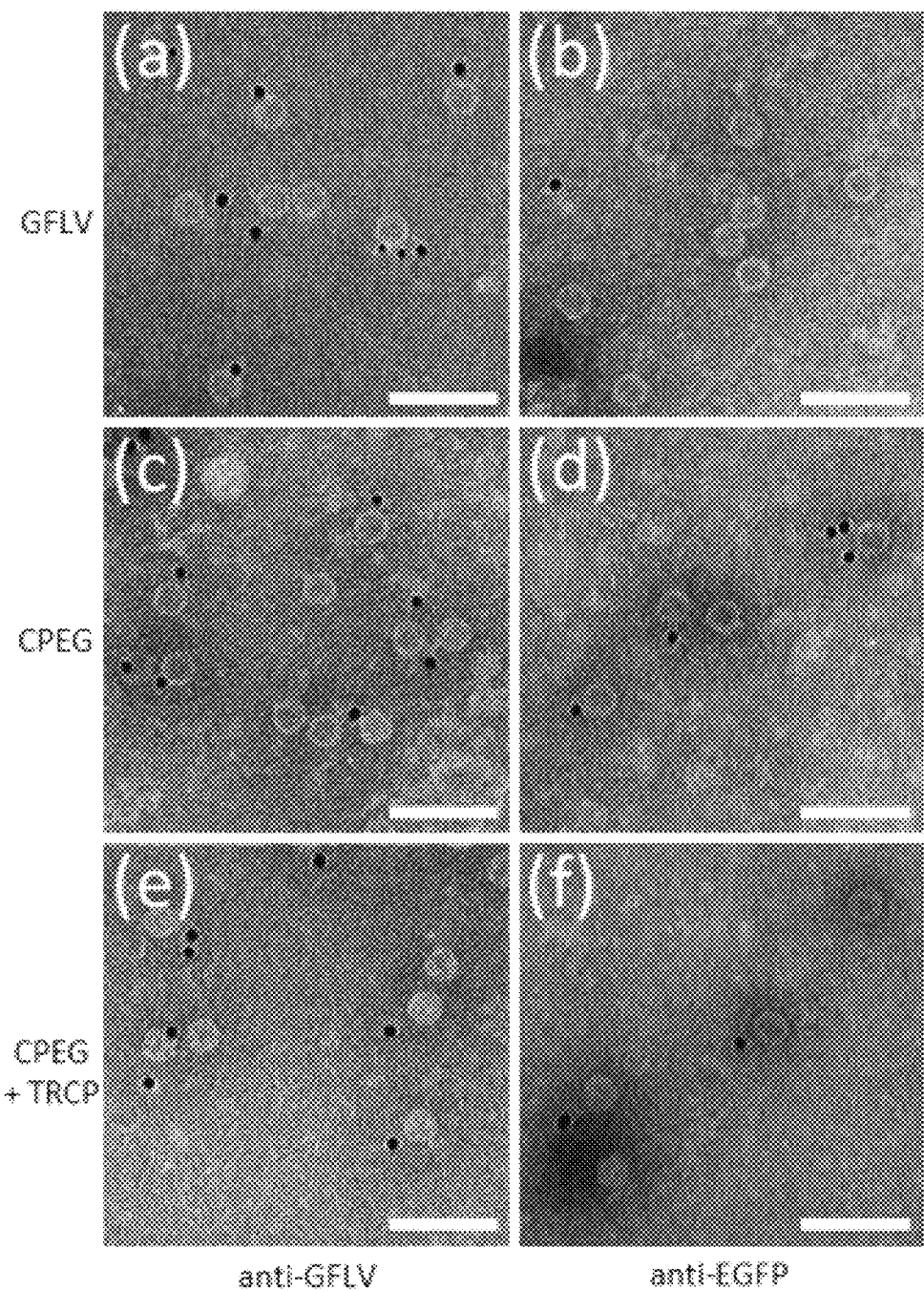

FIG. 8: VLPs can be purified from $N.$ $benthamiana$ leaves coexpressing CPEG and TRCP. Transmission electron micrographs of purified GFLV (a, b), CPEG VLPs (c, d) and CPEG+TRCP VLPs (e, f) after immunogold labeling. Samples were processed for ISEM using anti-GFLV (a, c, e) or anti-EGFP (b, d, f) antibodies and particles decorated using anti-mouse antibodies conjugated to 10 nm colloidal gold. Scale bars: 100 nm.

Figure 9:
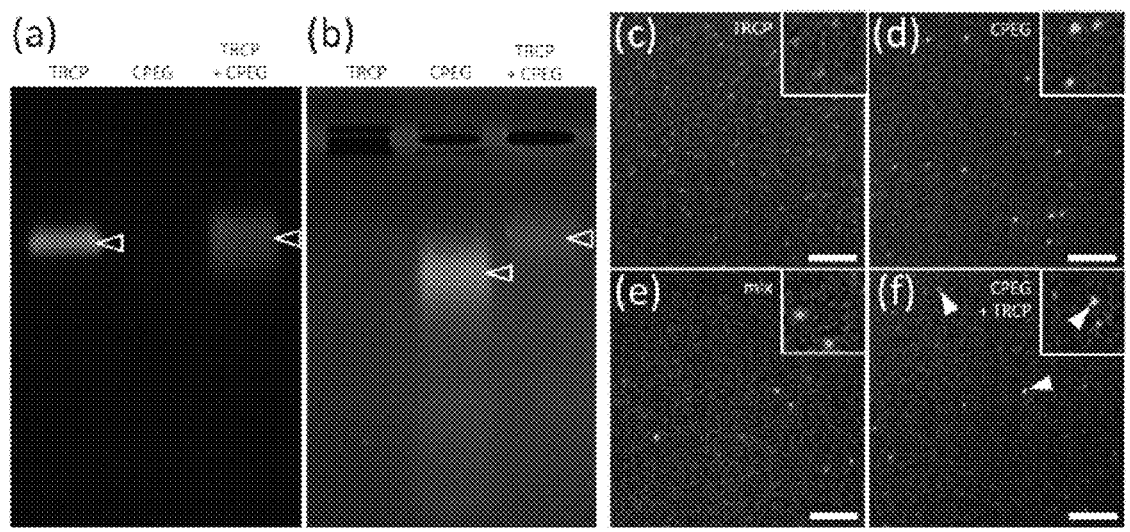

FIG. 9: Hybrid VLPs are produced upon coexpression of CPEG and TRCP. (a, b) Fluorescent imaging of TRCP, CPEG or CPEG+TRCP VLPs separated by native agarose gel electrophoresis. Imaging was done sequentially using a G:box imaging system, first at an excitation of $\lambda_{ex}480$-540 nm and an emission of $\lambda_{em}590$-660 nm to detect TagRFP (a), then at $\lambda_{ex}4450$-485 nm and $\lambda_{em}510$-540 nm to detect EGFP (b). Fluorescent VLPs in the gel are indicated by empty arrowheads. (c to f) Single particle microscopy images of purified TRCP (c), CPEG (d), mixed TRCP and CPEG VLPs at 1:1 ratio (e) and coexpressed CPEG+TRCP (f). Epifluorescence imaging was done sequentially at $\lambda_{ex}455$-495 nm-$\lambda_{em}505$-555 nm to detect EGFP and at $\Delta_{ex}532.5$-557.5-$\lambda_{em}570$-640 nm to detect TagRFP. White arrowheads point at hybrid VLPs. Scale bars: 5 µm.

Figure 10:
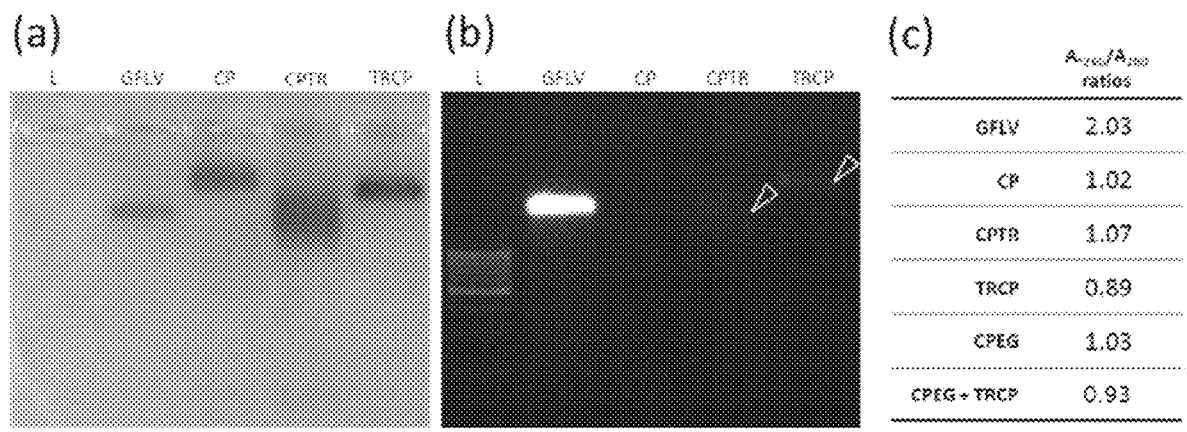

FIG. 10: Purified VLPs are nucleic acids-free. (a and b) Purified GFLV and CP, CPTR and TRCP VLPs separated by native agarose gel electrophoresis after Coomassie blue (a) and ethidium bromide staining (b). Arrowheads point to bands corresponding to cross-talk. (c) $O.D._{260}/O.D._{280}$ ratios of purified samples.

Figure 11:
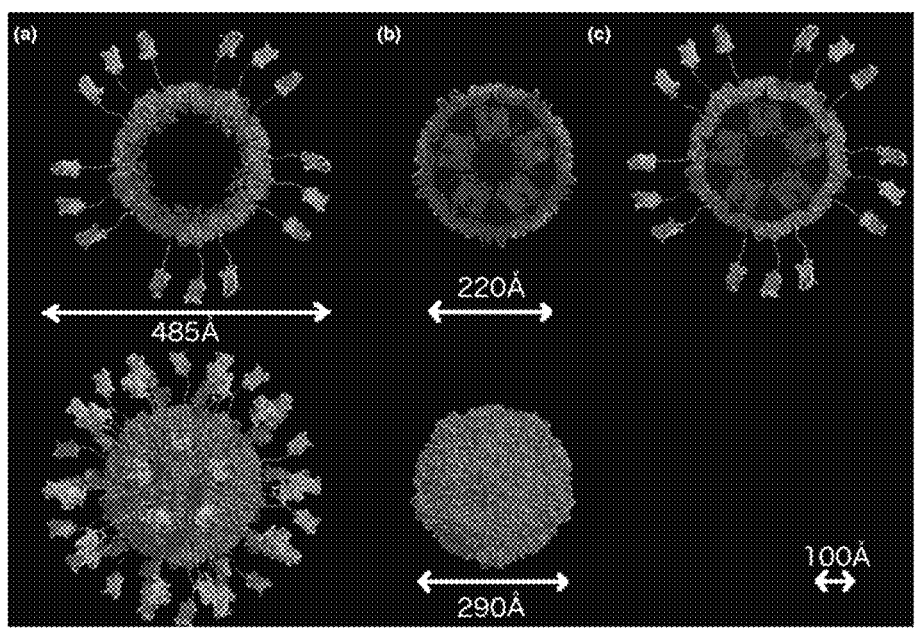

FIG. 11. Molecular models of fluorescent VLPs. (a) CPEG VLP including 60 CPs fused with EGFP in C-terminal position. (b) TRCP VLP including 60 CPs fused with TR in N-terminal position. (c) TRCPEG VLP including 60 CPs fused with EG in C-terminal and with TR in N-terminal positions. All VLPs are depicted in the same orientation in ribbon representation, with the CP, EGFP, TagRFP and linker peptide.

Figure 12:
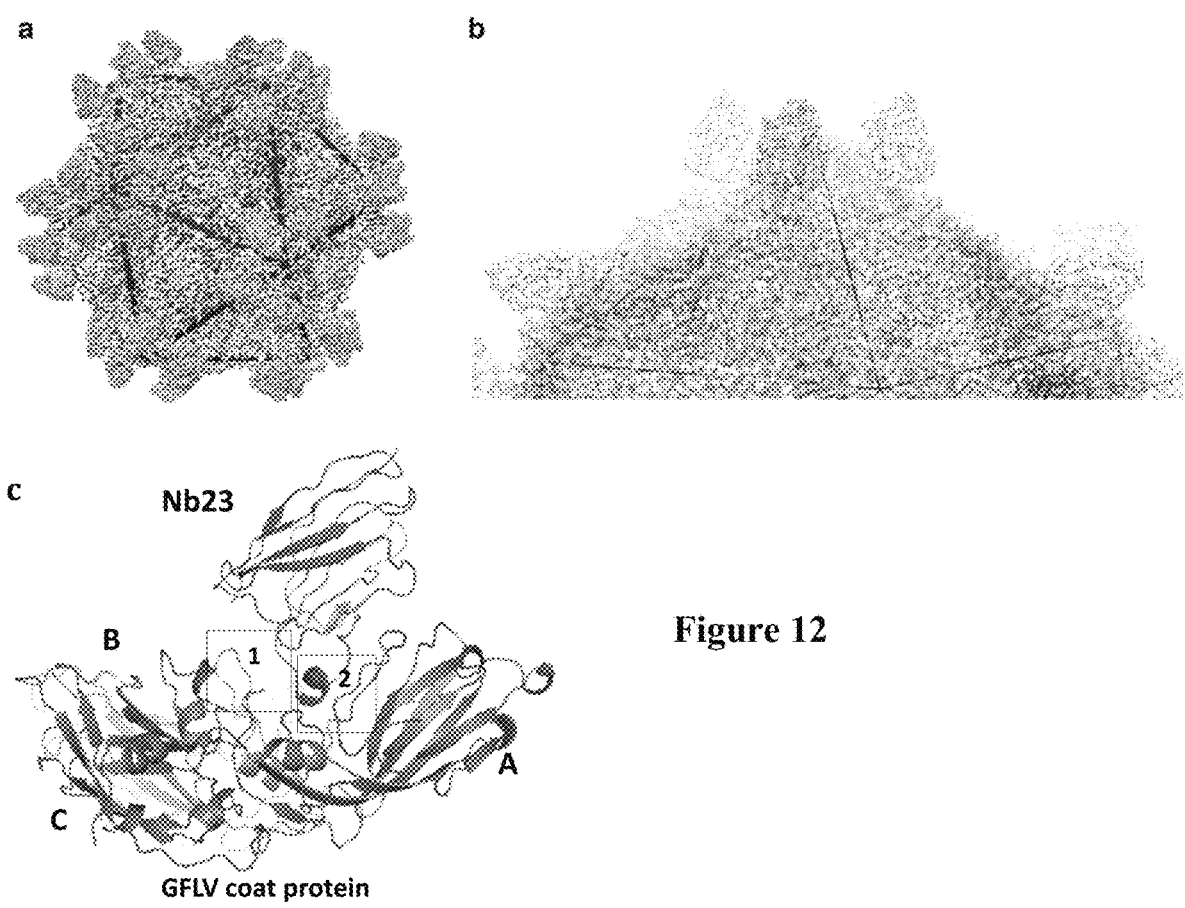

FIG. 12. The 2.8 Å resolution cryo-EM structure of the GFLV-Nb23 complex. a: Global 3D reconstruction of the GFLV-Nb23 complex with Nb23 shown in dark grey on the GFLV outer surface. Icosahedral edges are indicated by black triangles. Nb23 forms a stoichiometric 1:1 complex with the viral capsid protein (CP) resulting in 60 Nb23 bound per virion. b: Detailed view of the cryo-EM map with the fitted atomic model showing the three CP and three Nb23 per icosahedron face (c) A thin slice of the cryo-EM map reveals the intimate contact between Nb23 residues and GFLV surface in particular in regions 1 and 2.

Figure 13:
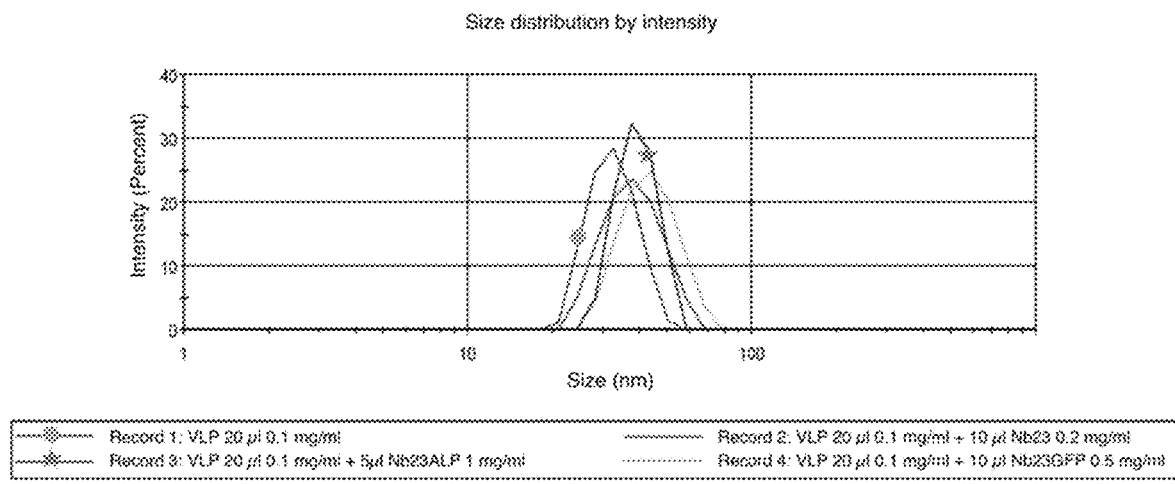

FIG. 13. Nb23-mediated decoration of TRCP VLP measured by dynamic light scattering (DLS). The graph corresponds to the size distribution by intensity of purified TRCP VLPs alone (grey curve marked with a plain circle sign) or decorated with either Nb23 (dark grey curve without marking), Nb23GFP (dark grey curve marked with a star sign) or Nb23:ALP (light grey curve without marking). All particles are monodisperse with diameters of 32.0+/−2 nm (mean+/−SD, n=3) for TRCP VLP, 37.8+/−2 nm (mean+/−SD, n=3) for VLP saturated with Nb23, 43.8+/−2 nm (mean+/−SD, n=3) for VLP saturated with Nb23:GFP and 40.0+/−2 nm (mean+/−SD, n=3) for VLP saturated with Nb23:ALP.

Figure 14:
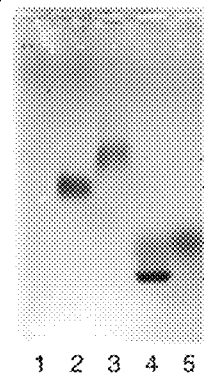

FIG. 14. TRCP VLP can be decorated with Nb23 and Nb23:GFP. TRCP VLP after native agarose gel electrophoresis and Coomassie blue staining. Lane 1: Nb23 alone. Lane 2: TRCP VLP decorated with Nb23. Lane 3: TRCP VLP alone. Lane 4: TRCP VLP decorated with Nb23:GFP. Lane 5: Nb23:GFP- or Nb23:GFP alone. Note the shifts in migration of the VLP when decorated (lanes 2 and 4 compared to 3). Note also that migration is dependent on the net charge of the complexes rather their molecular masses.

Figure 15:
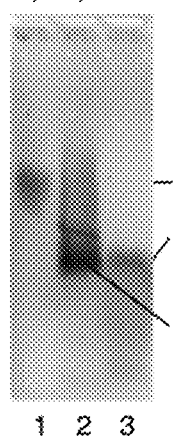

FIG. 15. Efficient display of Nb23ALP at the surface of RFP:CP-derived VLPs. TRCP VLP after native agarose gel electrophoresis, Coomassie blue staining and FastRed staining. Lane 1: TRCP VLP alone. Lane 2: TRCP VLP decorated with Nb23ALP. Lane 3: Nb23ALP alone. Note that Alkaline phosphatase remains functional upon binding to VLPs.

Figure 16:
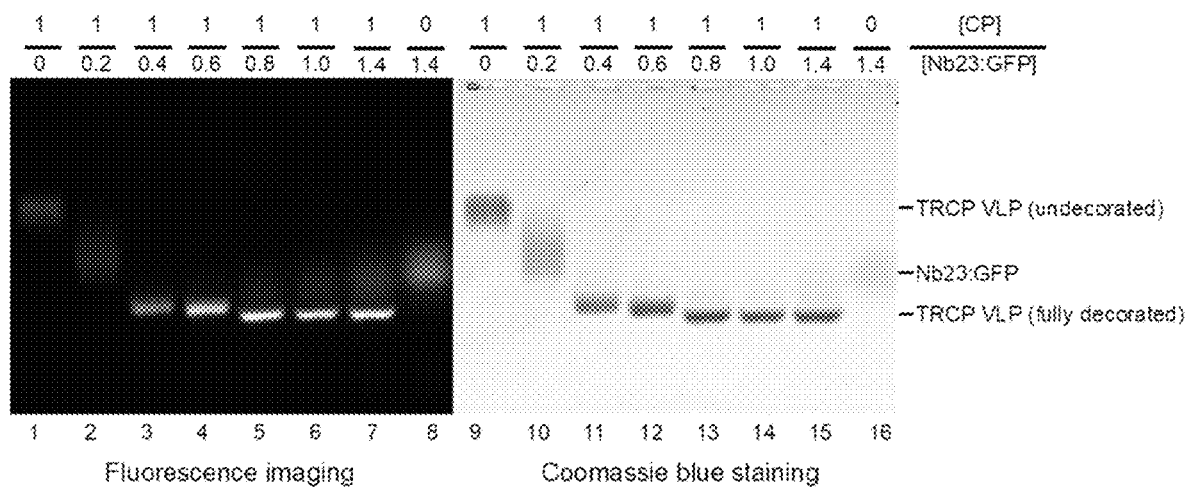

FIG. 16. Nb23GFP forms a stoichiometric 1:1 complex with the viral capsid protein (CP). TRCP VLP was incubated in the presence of increasing amounts of Nb23GFP and separated by native agarose gel electrophoresis. Molecular ratios between GFLV CP and Nb23:GFP are given above each lane. Gel was imaged under epifluorescence illumination (left) and after Coomassie blue staining (right). Note the progressive shift in migration of TRCP VLP that is proportional to the addition of Nb23GFP molecules. Note also that fully decorated TRCP VLP with Nb23GFP appear white (lanes 5 and 6) whereas TRCP VLP is dark grey and Nb23GFP is light grey.

Figure 17:
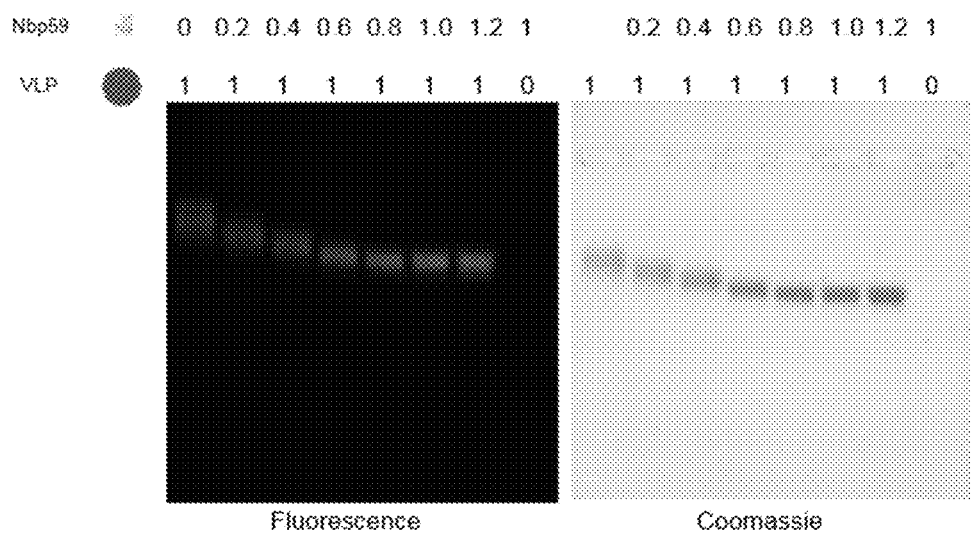

FIG. 17. Nbp59 forms a stoichiometric 1:1 complex with the viral capsid protein (CP). TRCP VLP was incubated in the presence of increasing amounts of Nbp59 and separated by native agarose gel electrophoresis. Molecular ratios between GFLV CP and Nbp59 are given above each lane. Gel was imaged under epifluorescence illumination (left) and after Coomassie blue staining (right). As for Nb23GFP, a progressive shift is observed in migration of TRCP VLP until 1:1 ratio between CP and Nbp59 is achieved.

Figure 18:
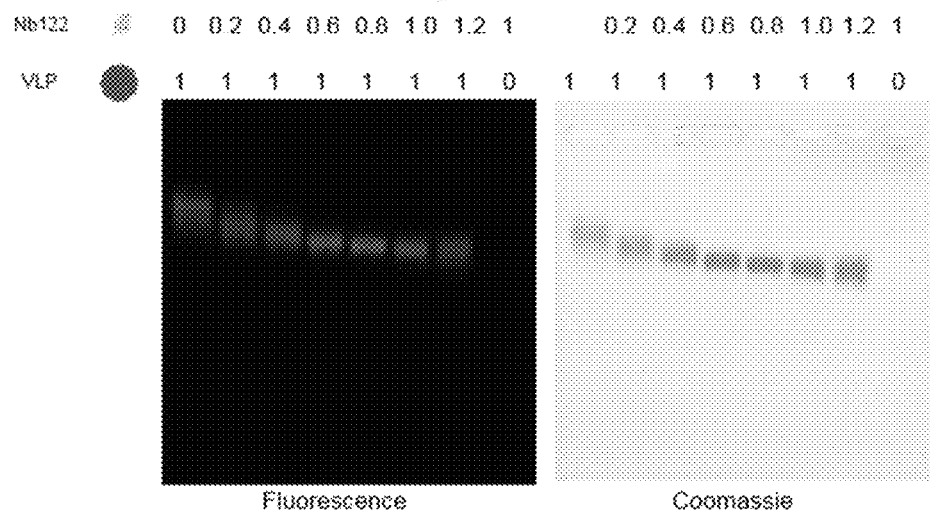

FIG. 18. Nb122 forms a stoichiometric 1:1 complex with the viral capsid protein (CP). TRCP VLP was incubated in the presence of increasing amounts of Nb122 and separated by native agarose gel electrophoresis. Molecular ratios between GFLV CP and Nb122 are given above each lane. Gel was imaged under epifluorescence illumination (left) and after Coomassie blue staining (right). As for Nb23GFP and Nbp59 a progressive shift is observed in migration of TRCP VLP until 1:1 ratio between CP and Nb122 is achieved.

Figure 19:
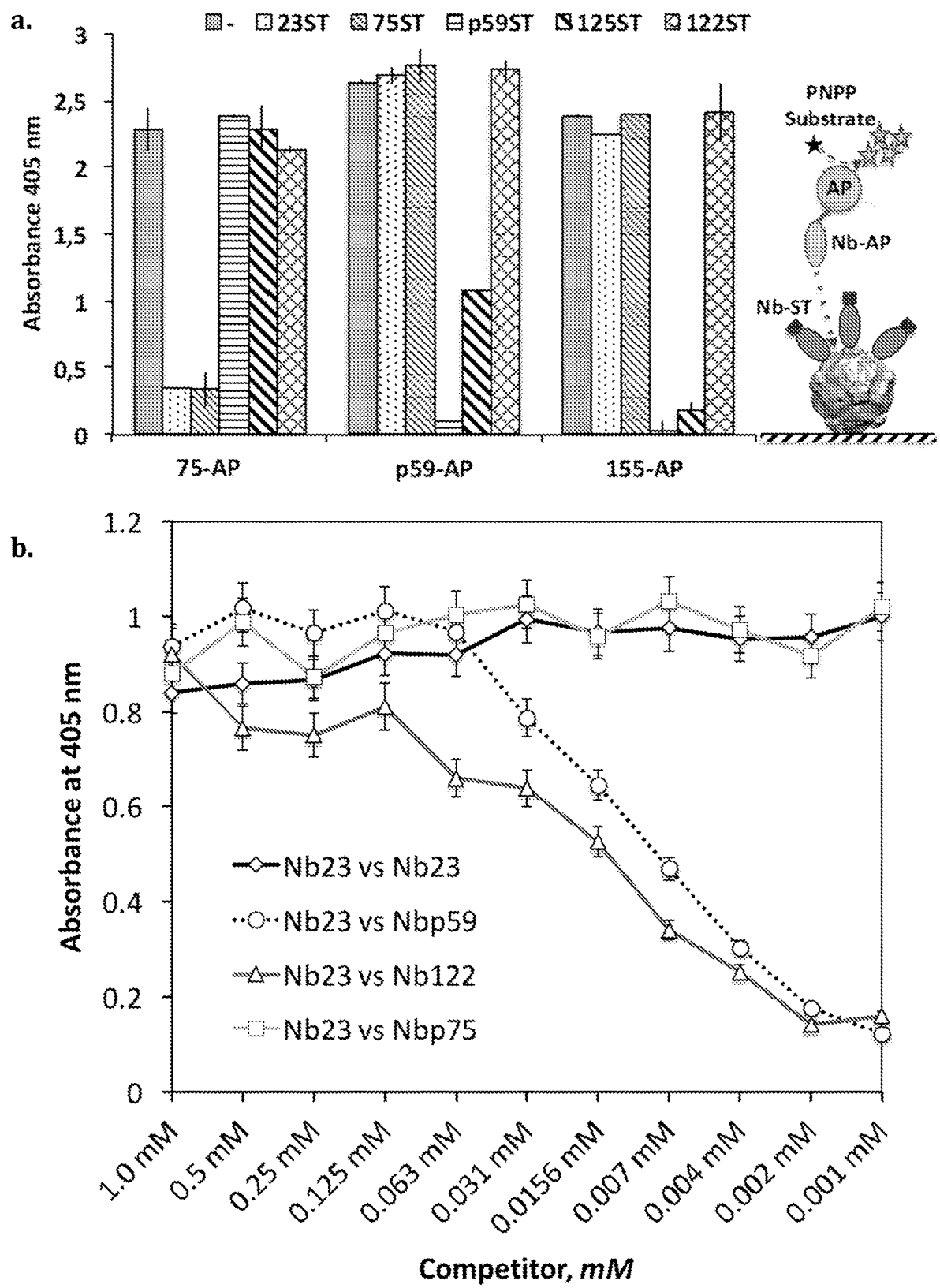

FIG. 19. Non-competitive nanobodies to Nb23 are affine to VLP-TRCP. (a) Competitive ELISA test against purified GFLV-13. Pure GFLV particles were directly coated on ELISA plates and incubated with anti-GFLV strep-tagged nanobodies (Nb23ST, Nb75ST, Nbp59ST, Nb125ST or Nb122ST) at 1:100 dilution in conjugate buffer. Viral particles complexed with NbSTs were challenged with anti-GFLV nanobodies fused to ALP (Nb75-AP, Nbp59-ALP or Nb155-AP) at a 1:500 dilution in conjugate buffer. Detection was realized using para-nitrophenylphosphate (PNPP) and absorbance measured at 405 nm with a Titertek Multiskan MCC/340 reader (Labsystems). (b) Competitive ELISA between Nb23 and Nbp59, Nbp75 and Nb122. Plates were coated directly with 100 ng of purified GFLV particles diluted in coating buffer before incubation with strep-tagged nanobodies (Nb23, Nb75, Nbp59 or Nb122) at a 1:100 dilution in conjugate buffer (stock solutions at 1 µg·µl$^{-1}$). A serial dilution of the same anti-GFLV nanobodies (Nb23, Nb75, Nbp59 or Nb122) fused to AP was added starting at 2 mM to reach final concentration of 1 µM. Competition assessment of tested nanobodies on viral epitopes was performed by challenging Nb23 with the different Nbs-ALP as competitors. Detection was realized using PNPP and absorbance at 405 nm measured with a Titertek Multiskan MCC/340 reader (Labsystems). Experiment was repeated six times (n=6).

Figure 20:
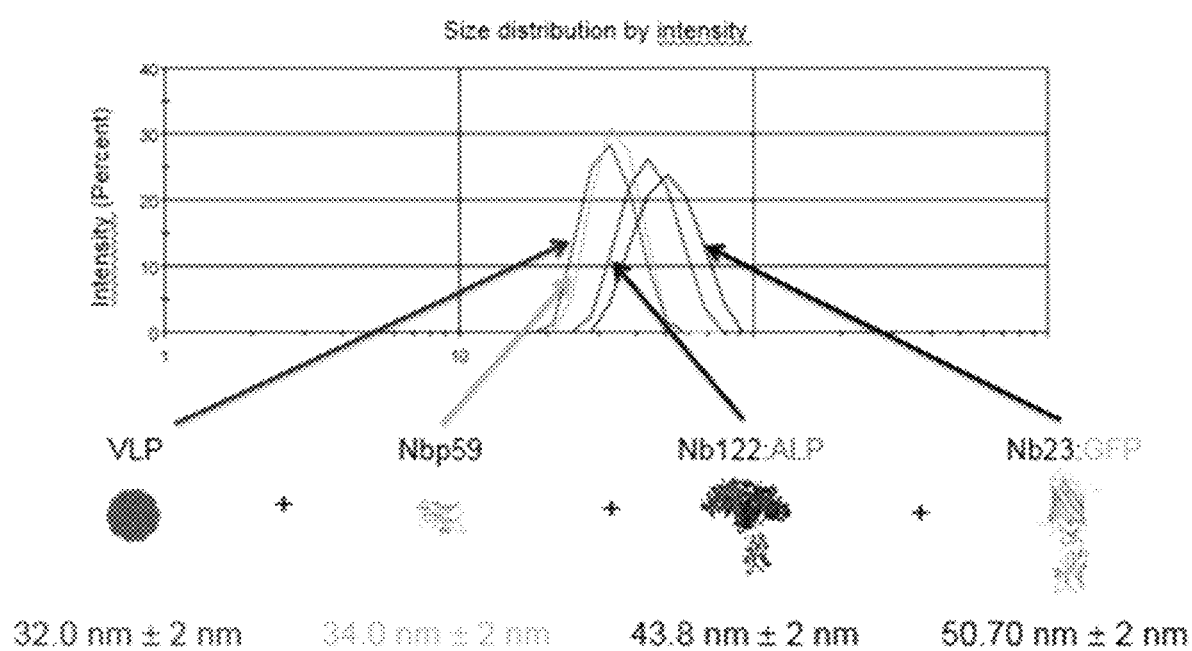

FIG. 20. Multiple decoration of VLP measured by dynamic light scattering (DLS). The graph corresponds to the size distribution by intensity of purified VLPs alone or decorated with either Nbp59, Nbp59 and Nb122:ALP or Nbp59 and Nb122:ALP and Nb23:GFP. All particles are monodisperse with diameters of 32.0+/−2 nm for VLP alone, 34.0+/−2 nm for VLP saturated with Nbp59, 43.8+/−2 nm for VLP saturated with Nbp59 and Nb122:ALP and 50.7+/−2 nm for VLP saturated with Nbp59 and Nb122:ALP and Nb23:GFP. The increase in size of the VLP confirms the successful displaying of two and even three different nanobodies on its surface.

Figure 21:
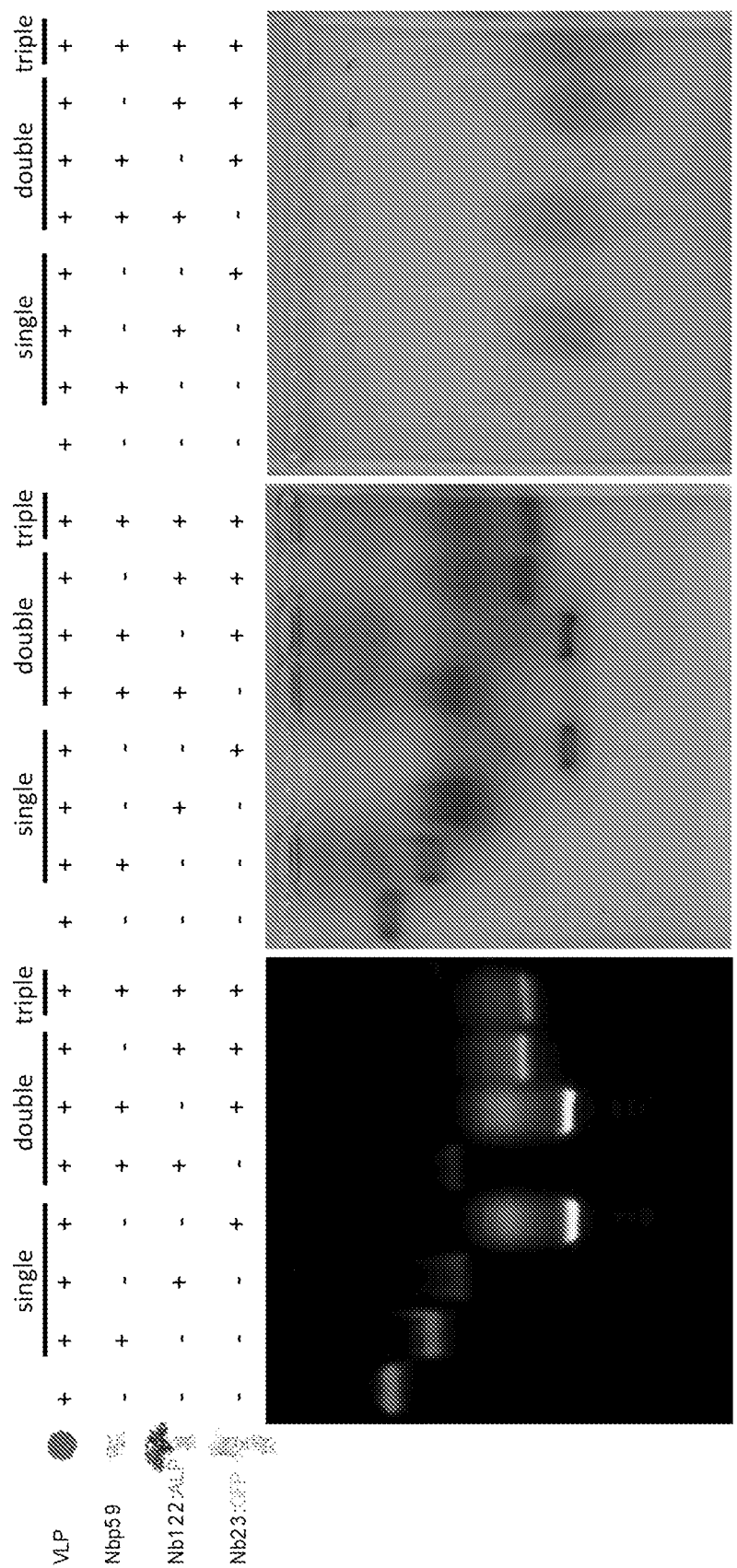

FIG. 21. Effective decoration of VLPs with single, double or triple combinations of Nanobodies. VLPs were incubated with different combinations of nanobodies (Nbp59 and/or Nb122:ALP and/or Nb23:GFP) and separated by native agarose gel electrophoresis. Tested combinations are displayed above each lane. Gel was imaged under epifluorescence illumination (left), after Coomassie blue staining (center) or after fast red staining (right). Note that for each different combination of nanobodies displayed on the surface of VLPs the migration pattern is different. This migration is dependent on the net charge rather than molecular masses. Green fluorescence outlines that the activity of the GFP tag is maintained and the protein is in native conformation. FastRed staining reveals that complexes displaying the Nb122:ALP on the surface still possess alkaline phosphatase activity.

Figure 22:
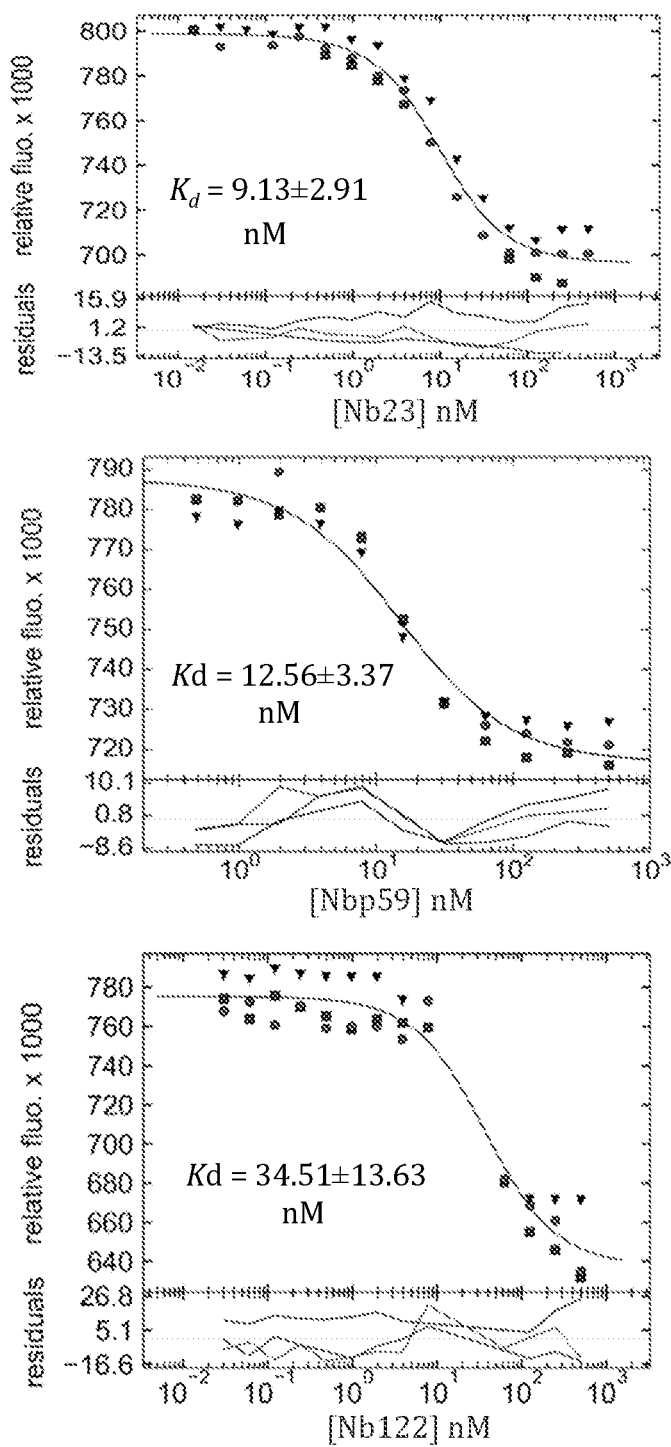

FIG. 22. Nb23, Nbp59 and Nb122 binding affinities to TRCP VLP determined by microscale thermophoresis (MST). Analyses were performed three times and led to a Kd of 9.13±2.91 nm for Nb23, 12.56±3.37 nm for Nbp59 and 34.51±13.63 nm for Nb122.

Figure 23:
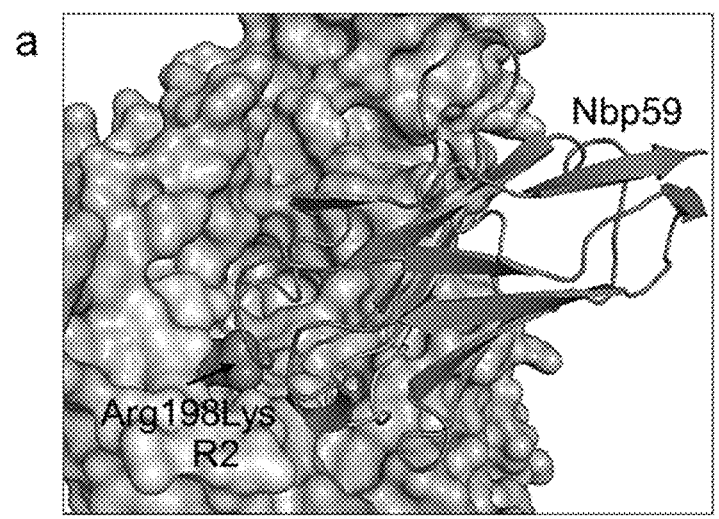
Figure 23:
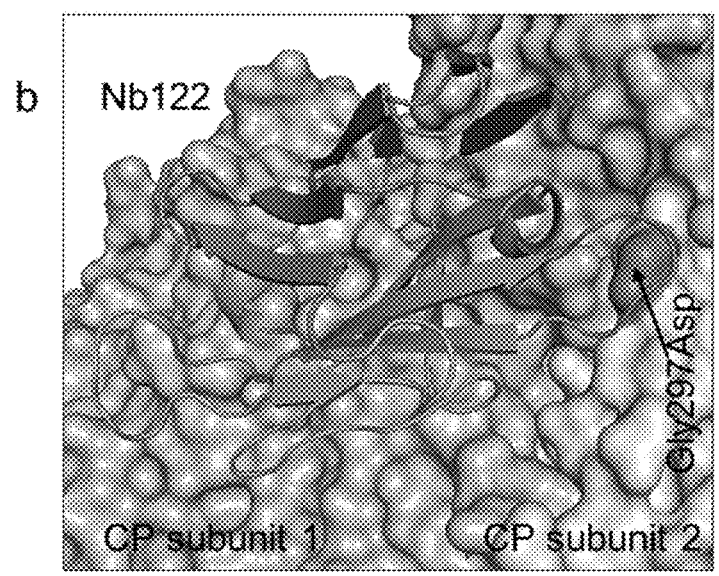
Figure 23:
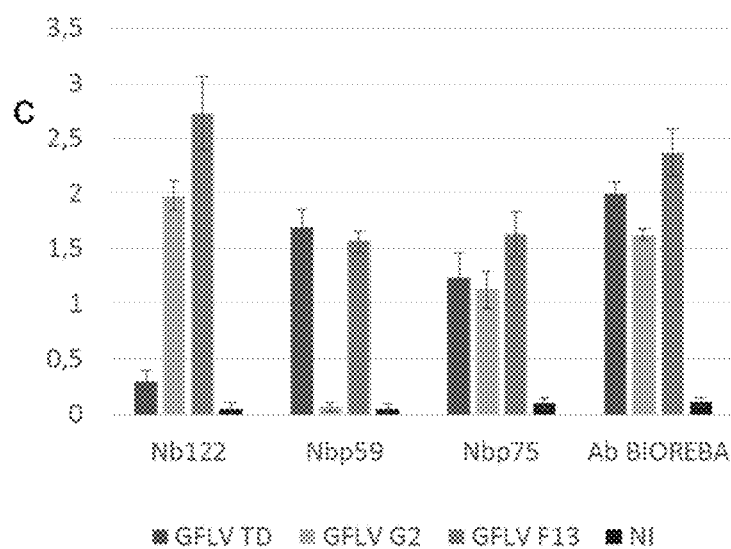

FIG. 23. Structural and biological data validating Nbp59 and Nb122 docking on VLP. (a) Docking model of the Nbp59 to the CPGFLV showing the interaction of CDR3 of nanobody with the amino acid Arg on position 198 in substitution of Lys (Arg198Lys in dark grey) in R2 region of G2 GFLV strain (Schellenberger et al., 2011). (b) Docking model of the Nb122 to the CPGFLV showing a steric clash between nanobody docked on subunit 1 of CPGFLV and the Gly297Asp (in dark grey) of subunit 2 of TD GFLV strain (Schellenberger et al., 2011). (c) DAS-ELISA of infected leaves with different GFLV strains (TD, G2 and F13). Capturing was done by Ab BIOREBA and detection was performed by three Nbs:ALP (Nbp59, Nb122 and Nbp75) respectively. Detection by Ab BIOREBA was used as positive control. Experiment was performed (n=6).

DETAILED DESCRIPTION OF THE INVENTION

The present invention relates to VLPs derived from Grapevine fanleaf virus (GFLV) coat proteins, and the uses thereof. The invention particularly provides GFLV coat proteins VLPs conjugated to compounds, and their use to produce nucleic-acid-free virus-like particles that expose compounds and optionally encage compounds. The invention shows that it is possible to produce particles by assembly of a single GFLV coat protein in such a way that (i) encapsidation of native viral RNA is avoided, (ii) at least one compound (e.g., a foreign protein or peptide) is surface exposed and (iii) optionally another compound (e.g., a foreign protein or peptide), which can be the same or different from the other compounds, is encaged/protected inside the particle. These conjugated proteins and VLPs may be used to expose and optionally encage any compound of interest and have utility in various fields such as the pharmaceutical, agrosciences, or veterinary areas.

An object of the invention thus resides in virus-like particles comprising, or consisting of, or obtainable from GFLV coat proteins and at least two different anti-GFLV coat protein antibodies or antibody derivatives.

A further object of the invention is a virus-like particle comprising or obtainable from GFLV coat proteins and at least two different anti-GFLV coat protein antibodies or antibody derivatives, said GFLV coat protein and/or anti-GFLV coat protein antibodies or antibody derivatives being conjugated to a compound. Conjugation may be covalent (e.g., through genetic or chemical coupling) and/or non-covalent (e.g., through ligand mediated binding).

VLPs

The term "virus-like-particle" or "VLP" more specifically designates a particle which is essentially made by self-assembly of coat proteins. VLPs are typically devoid of nucleic acids and not infectious. Preferred unmodified VLPs of the invention are icosahedral. Also, in unmodified form, they usually are small particles having a diameter below 50 nm, typically between 20-40 nm, more preferably between 25-35 nm, such as about 30 nm. The invention indeed shows that GFLV coat proteins lead to the production of particles that are small in size, preferably in the nanometer range, and simple in structure and likely non-toxic due to their exclusive protein composition (biomaterial). Such characteristics represent a further advantage of the invention. Of course, the size of the VLPs may be modified when compounds are conjugated to the coat protein and/or anti-GFLV coat protein antibodies or antibody derivatives, as disclosed in the present application.

In one embodiment, VLPs of the invention are essentially composed of or obtained from several copies of a same GFLV coat protein (homoVLPs), optionally a GFLV coat protein conjugated to a compound.

In another embodiment, VLPs of the invention are composed of, or comprise, or are obtained from a mixture of distinct GFLV coat proteins (heteroVLPs). Examples of such heteroVLPs include (i) VLPs comprising a mixture of a GFLV coat protein and fragments thereof, or (ii) VLPs comprising a mixture of a conjugated GFLV coat protein and a non-conjugated GFLV coat protein.

Optionally, VLPs of the invention are composed of, or comprise, or are obtained from a mixture of a GFLV coat protein conjugated to a first compound and a GFLV coat protein conjugated to a second compound (hybridVLPs). Optionally, a mixture of the same GFLV coat protein is used fused to a first and second compound, respectively. A particular hybridVLP comprises or is obtained from a mixture of a GFLV coat protein conjugated in C-ter to a first compound and a GFLV coat protein conjugated in N-ter to a second compound.

In a particular embodiment, a hybridVLP comprises the GFLV coat protein and at least one exposed compound at the surface of the particle by conjugation of the at least one compound to anti-GFLV coat protein antibodies or antibody derivatives.

In another particular embodiment, a hybridVLP comprises an encaged compound which is N-terminally conjugated to the GFLV coat protein and at least one exposed compound at the surface of the particle by conjugation of the at least one compound to anti-GFLV coat protein antibodies or antibody derivatives.

In heteroVLPs or hybridVLPs, the ratio between the various coat proteins may be varied and adjusted by the skilled artisan according to the needs and operating conditions, without affecting the assembly and/or integrity of the VLP.

VLPs of the invention may be prepared using a GFLV coat protein. In this regard, the term "GFLV coat protein" designates any coat or capsid protein or polypeptide derived from a GFLV, e.g. obtained from GFLV, or having the sequence of a coat protein of GFLV, or having a sequence designed from a sequence of a coat protein of GFLV. The term coat protein includes recombinant proteins, synthetic proteins, or purified proteins. The coat protein may be a polypeptide having an amino acid sequence identical to that of GFLV or may contain structural modifications such as mutations, deletions and/or insertions of one or several amino acid residues, as long as the protein retains the ability to assemble into a particle.

The amino acid sequence of GFLV coat protein is provided as SEQ ID NO: 1.

In a particular embodiment, the GFLV coat protein is a polypeptide comprising all or part of SEQ ID NO: 1 and able to assemble into a VLP. "Part" of a sequence designates preferably a continuous portion of at least 80% of that sequence, more preferably of at least 85%, even more preferably at least 90%, 95%, or more.

Several strains of GFLV have been described in the art and are available, such as GFLV-F13 (Viry et al. 1993), or GFLV-GHu (Vigne et al., 2004). As a particular example, the invention uses a GFLV coat protein derived from any strain of GFLV such as F13.

In a most preferred embodiment, the GFLV coat protein for use in the invention is a polypeptide comprising all or part of the amino acid sequence of SEQ ID NO: 1, or a sequence having at least 90% identity to SEQ ID NO: 1. The term "identity" in relation to an amino acid sequence as used herein refers to the degree of correspondence between two amino-acid sequences (no gaps between the sequences). In other terms, it is the extent, expressed as a percentage, to which two amino acid sequences have the same amino acid at equivalent positions. The "percentage identity" between two amino acid sequences (A) and (B) is determined by comparing the two sequences aligned in an optimal manner, through a window of comparison. Said alignment of sequences can be carried out by well-known methods, for example, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity can be obtained by dividing the full number of identical amino acid residues aligned by the full number of residues contained in the longest sequence between the sequence (A) and (B). Sequence identity is typically determined using sequence analysis software. The % identity can be determined by known computer programs such as BLAST, FASTA, etc. For comparing two amino acid sequences, one can use also, for example, the tool "Emboss needle" for pairwise sequence alignment of proteins providing by EMBL-EBI and available on Worldwide Web site: ebi.ac.uk/Tools/services/web/toolform.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

A particular example of a GFLV coat protein is a protein comprising or consisting of SEQ ID NO: 1. Another particular example of a GFLV coat protein is a protein comprising or consisting of amino acids 2-505 of SEQ ID NO: 1. Another particular example of a GFLV coat protein is a protein comprising or consisting of amino acids 1-504 or 2-504 of SEQ ID NO: 1. Another particular example of a GFLV coat protein is a protein comprising or consisting of amino acids 1-503 or 2-503 of SEQ ID NO: 1. Another example of a GFLV coat protein is a protein comprising or consisting of SEQ ID NO: 1 with 1 to 10 or 1 to 5 amino acid substitutions, additions or deletions, preferably substitutions. By "substitution" herein is meant the replacement of an amino acid at a particular position with another amino acid. By "addition" is meant the addition of an amino acid at a particular position in a polypeptide sequence. By "deletion" is meant the removal of an amino acid at a particular position in a polypeptide sequence.

The amino acid substitutions may be conservative. A conservative substitution is the replacement of a given amino acid residue by another residue having a side chain ("R-group") with similar chemical properties (e.g., charge, bulk and/or hydrophobicity). In general, a conservative amino acid substitution will not substantially change the functional properties of a protein. Conservative substitutions and the corresponding rules are well-described in the state of the art. For instance, conservative substitutions can be defined by substitutions within the group of the amino acid which are known by the person skilled in the art such as acidic amino acid, basic amino acid, hydrophilic uncharged amino acid, aliphatic uncharged amino acid, non-polar uncharged amino acid and aromatic amino acid.

The proteins may be prepared by recombinant technology (i.e., expression in a cell or in vitro system), by synthesis, purification, or combinations thereof. In this regard, the proteins may be produced by expression in plant cells, in planta, in bacteria (e.g., in E. coli), or in other eukaryotic cells (e.g., in yeast, in insect cells, in CHO cells etc. . . . ). Alternatively, expression may be performed in in vitro systems. Also, the proteins may be modified to improve their stability. In particular, the coat proteins may contain one or more peptidomimetic bonds such as for instance intercalation of a methylene ($-CH_2-$) or phosphate ($-PO_2-$) group, secondary amine ($-NH-$) or oxygen ($-O-$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, esters, phosphinates, phosphinics, phosphonamides and the like.

GFLV coat proteins may be used as such to produce VLPs of the invention. Also, as discussed previously, the invention shows that GFLV coat proteins may be conjugated to large compounds without losing their ability to assemble into VLPs. Moreover, the conjugation strategy allows control of exposure/encaging of a compound. Furthermore, very large compounds can be conjugated (e.g., which can represent at least 50% of the size of the coat protein itself) without affecting the ability of the protein to assemble into VLPs.

Conjugation may be covalent or not, direct or not (i.e., via a linker), and/or chemical, enzymatic or genetic. Furthermore, conjugation may involve terminal and/or lateral coupling. Also, a conjugated GFLV coat protein of the invention may comprise one or several conjugated compounds.

Conjugation can be carried out by any acceptable means of bonding taking into account the chemical nature and obstruction of the GFLV coat protein and compound. In this regards, coupling can thus be performed by one or more covalent, ionic, hydrogen, hydrophobic or Van der Waals bonds, cleavable or non-cleavable in physiological medium or within cells.

Furthermore, while coupling can be performed at any reactive groups of the GFLV coat protein, accessibility of the reactive group in a subsequent VLP should be considered. In this regard, the inventors have found that coupling at the N-term and/or C-term ends of the GFLV coat protein does not affect the ability of the coat protein to form a particle. Such terminal coupling is thus most preferred for the present invention. In addition, the inventors have surprisingly found that the fusion of a compound at the C-terminus of a GFLV coat protein results in the exposure of the compound on the surface of particles prepared with the conjugate, whereas a compound fused to the N-terminal leads to its internalization into the VLPs, making the compound inaccessible to antibodies ("caging"). It is therefore possible to adjust the coupling strategy to the type of compound, and also to produce VLPs having two distinct properties: the surface exposure and the protection by internalization (caging) of compounds of interest.

In a first preferred embodiment, conjugation is obtained by covalent coupling to the GFLV coat protein, typically by genetic fusion (i.e., by expression in a suitable system of a nucleic acid construct encoding the GFLV coat protein and the compound as a genetic fusion), optionally at the N-ter and/or C-ter of the coat protein, preferably at the N-terminal end.

In a particular embodiment, the invention relates to a GFLV coat protein conjugated at its N-terminal end to a compound (i.e., TagRFP). A typical structure of such conjugates is Compound-(Linker)$_n$-Coat protein with n=0 or 1. Conjugation at the N-ter end more preferably comprises conjugation at the first N-ter amino acid of the coat protein. The present invention does indeed show that conjugation at amino acid Met$_1$ of SEQ ID NO: 1 or at amino acid Gly$_1$ of a GFLV coat protein comprising amino acids 2-505 of SEQ ID NO: 1 or a variant thereof can generate molecules that can form VLPs and that encage the conjugated compound inside of the VLP.

In another particular embodiment, the invention relates to a GFLV coat protein conjugated at its C-terminal end to a compound (i.e., Fluorescent proteins). A typical structure of such conjugates is Coat protein-(Linker)$_n$-Compound with n=0 or 1. Conjugation at the C-ter end more preferably comprises conjugation at anyone of the last three C-ter amino acids of the protein. The present invention does indeed show that conjugation at amino acid Phe$_{503}$, Pro$_{504}$ or Val$_{505}$ of SEQ ID NO: 1 or a variant thereof can generate molecules that can form VLPs and that expose the conjugated compound outside of the VLP. More preferably, C-ter conjugation involves conjugation to the last C-ter amino acid residue of the coat protein.

The compound may be coupled directly to the GFLV coat protein, or indirectly by means of a linker. Means of covalent chemical coupling, include e.g., the use of bi- or multifunctional agents containing e.g., alkyl, aryl, peptide or carboxyl groups. Examples of linkers include any neutral amino acid or peptide sequence, such as for instance G$_3$S, G$_3$SG$_3$, or DPAFLYKVVRSFGPA (SEQ ID NO: 6).

In a preferred embodiment, the compound is covalently linked to the GFLV coat protein, directly or via a linker.

In a further preferred embodiment, the compound and coat protein are linked by a peptide bond, either directly or via a linker.

Anti-GFLV Coat Protein Antibodies or Antibody Derivatives

The present invention relates to a VLP comprising a GFLV coat protein and at least two or three different anti-GFLV coat protein antibodies or antibody derivatives.

The present invention shows that VLPs derived from GFLV coat proteins can be simultaneously conjugated to at least two or three different types of anti-GFLV coat protein antibodies or antibody derivatives, said antibodies or antibody derivatives optionally being conjugated to proteins. For instance, the VLPs can be conjugated to up to 60 anti-GFLV coat protein antibodies or antibody derivatives by particle for each type of antibodies or antibody derivatives. According, with three different anti-GFLV coat protein antibodies, the VLP can bear up to 180 antibodies per VLP.

Preferably, the different anti-GFLV coat protein antibodies or antibody derivatives do not compete with each other for the binding to the GFLV coat protein. The present invention shows that a combination of at two or three different anti-GFLV coat protein antibodies or antibody derivatives can be used simultaneously. Accordingly, the VLP may comprise 1-60 copies of a first anti-GFLV coat protein antibodies or antibody derivatives, 1-60 copies of a second anti-GFLV coat protein antibodies or antibody derivatives and optionally 1-60 copies of a third anti-GFLV coat protein antibodies or antibody derivatives. Optionally, a fourth anti-GFLV coat protein antibodies or antibody derivatives can also be used simultaneously.

Preferably, the at least two or three different anti-GFLV coat protein antibodies or antibody derivatives do not compete with each other for the binding to the GFLV coat protein. In other words, the at least two or three different anti-GFLV coat protein antibodies or antibody derivatives bind epitopes of GFLV coat protein which are far enough for allowing the simultaneous binding of said two or three different anti-GFLV coat protein antibodies or antibody derivatives of the GFLV coat protein VLP.

By "compete" is intended to refer to an antibody or a derivative thereof which binds the same epitope or which overlaps the epitope of a first antibody or a derivative thereof, it is able to reduce by at least 20% binding of a first antibody or a derivative thereof to GFLV coat protein, when incubated at approximately similar concentrations. When an antibody or a derivative thereof is said to "compete with" a particular antibody, it means that the antibody or a derivative thereof competes with the particular antibody in a binding assay using either recombinant GFLV coat proteins or a GFLV VLP. It means that for an antibody (A) binding a recombinant GFLV coat proteins or a GFLV VLP the competition exists when an antibody (B) loses binding capacity of at least 20% to the recombinant GFLV coat proteins or the GFLV VLP due to the binding of antibody (A) one the same epitope (E1) or due to the fixation of antibody (A) overlapping the epitope (E2) of antibody (B) on the recombinant GFLV coat proteins or the GFLV VLP. Antibody or a derivative thereof may be tested for their ability to bind GFLV coat protein and a variant thereof or to compete with any particular antibodies or derivatives thereof as described in the examples or in WO2015/110601. In particular, the capacity to compete can be measured by a competitive ELISA.

Examples of anti-GFLV coat protein antibodies, or derivatives thereof retaining antigen specificity include, without limitation, monoclonal antibodies, nanobodies (e.g., derived from the structure of single chain only immunoglobulins found in camelids), single chain antibodies (i.e., ScFv or V$_{NAR}$ fragments), diabodies, etc.

The term nanobody (or VHH, Hamers-Casterman et al., 1993) designates a single chain polypeptide consisting essentially of three CDRs (complementarity-determining regions CDR1, CDR2 and CDR3) separated by four FR domains (for Framework regions) and essentially devoid of a light chain or a constant domain. The terms "nanobodies", "nanobody", "VHH", "VHH antibody fragment" or "single-domain antibody" are used interchangeably. Nanobodies typically have the following structure: FR1-CDR1-FR2-CDR2-FR3-CDR3-FR4. Preferably, the nanobodies of the invention are synthetic molecules produced by recombinant or chemical technologies. The CDRs of a given nanobody can be determined by any method available to those skilled in the art. For example, and in a non-limiting manner, the Chothia or the Kabat method can be used to determine the CDRs (Chothia et al., Nature 342, 877-883; Kabat et al., 1991, Sequences of Proteins of Immunological Interest, 5th Ed., United States Public Health Service, National Institutes of Health, Bethesda). Alternative method of determining CDRs can also be used such as the intermediate method between Chothia and Kabat called AbM (Oxford Molecular AbM antibody modelling software) or the so-called "Contact" method based on an analysis of available complex structures (Saerens et al, Mol Biol. 2005).

Nanobodies present high epitope specificity and affinity, usually in the nanomolar range. They are about ten times smaller than conventional IgG molecules. They are single-chain polypeptides, very stable, resisting extreme pH and temperature conditions. Moreover, they can resist to the action of proteases.

The present invention more particularly discloses particular nanobodies directed against the GFLV coat protein. These specific nanobodies have a very strong affinity for GFLV, in the nanomolar range.

The affinity of an antibody for GFLV may be determined by well-known methods described in the prior art. For instance, the Kd of an antibody can be determined by surface plasmon resonance assay in which the antibody is immobilized on the biosensor chip and the solubilized GFLV particle or GFLV coat protein is passed over the immobilized antibody under flow conditions leading to the measurements of $k_{on}$ and $k_{off}$ and thus Kd. Alternatively, GFLV particles or GFLV coat protein may be immobilized on the biosensor chip and the antibody of interest is passed over said immobilized GFLV VLPs or GFLV coat protein. As another alternative, the Kd of the antibody can be determined by Time Resolved-Fluorescence Energy Transfer analysis. In TR-FRET assays, ligands are usually coupled to conventional fluorescein-like or dy647-like fluorophores (acceptor species), whereas receptors are labelled with lanthanide cryptates (donor species). The FRET signal between the donor and the acceptor (for instance between terbium and d2) can be measured. This signal occurs when the antibody binds to the GFLV particle or GFLV coat protein only. The FRET signal can be plotted against antibody concentrations so as to obtain a dose-response curve from which the binding affinity of antibody for GFLV particle or GFLV coat protein can be determined.

The Kd of the nanobodies can be also determined by microscale thermophoresis. Microscale thermophoresis (MST) is a technology for the interaction analysis of biomolecules. Microscale thermophoresis is based on the detection of the movement of particles in a microscopic temperature gradient. Any change of the hydration shell of biomolecules due to changes in their structure/conformation results in a relative change in the movement along the temperature gradient and can be used to determine binding affinities. MST allows measurement of interactions directly in solution without the need of immobilization to a surface (immobilization-free technology). For determining Kd of a given anti-GFLV nanobody, purified TRCP VLPs in solubilized form are prepared and incubated with decreasing concentrations of nanobodies. After incubation, the samples are loaded in thin capillaries, a microscopic temperature gradient is induced by infrared laser and the directed movement of the solubilized TRCP VLP is detected and quantified. This thermophoresis signal is plotted against the antibody concentration so as to obtain a dose-response curve from which the binding affinity of nanobody for TRCP VLP can be deduced.

Preferably, the Kd of a nanobody for GFLV VLP is determined by microscale thermophoresis. Preferably, the at least two antibodies according to the invention have a Kd of at least 45 nM, preferably at least 40 nM, even more preferably at least 35 nM.

Accordingly, one of the at least two or three different anti-GFLV coat protein antibodies or antibody derivatives can selected from the group consisting of nanobodies Nb23, Nb101, Nb126, Nbp71, Nbp75, Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, Nbp12 and anti-GFLV coat protein antibodies or antibody derivatives comprising the sequences of a set of CDR 1, CDR 2 and CDR 3 from one of these nanobodies. For the sake of clarity, an "anti-GFLV coat protein antibody or antibody derivative comprising the sequences of a set of CDR 1, CDR 2 and CDR 3 from one of these nanobodies" refers to an antibody or antibody derivative with comprises the sequences of CDR1, CDR2 and CDR3 of this particular nanobody.

Optionally, two or three of the at least two or three different anti-GFLV coat protein antibodies or antibody derivatives can selected from the group consisting of nanobodies Nb23, Nb101, Nb126, Nbp71, Nbp75, Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, Nbp12 and anti-GFLV coat protein antibodies or antibody derivatives comprising the sequences of a set of CDR 1, CDR 2 and CDR 3 from one of these nanobodies.

The amino acid sequences of Nb23, Nb101, Nb126, Nbp71, Nbp75, Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139 and Nbp12 are disclosed in SEQ ID NOs: 9 to 29 and their CDRs sequences determined by Kabat method are disclosed in SEQ ID NOs: 34 to 102 and summarized in the following Table. Of course, based on the sequence of the nanobodies, the CDR may also be determined by another method such as IMGT.

| Nanobody (Nb) | SEQ ID NO: | CDR1 SEQ ID NO: | CDR2 SEQ ID NO: | CDR3 SEQ ID NO: |
| --- | --- | --- | --- | --- |
| 23 | 9 | 34 | 35 | 36 |
| p75 | 10 | 37 | 38 | 39 |
| 101 | 8 | 40 | 41 | 42 |
| 126 | 7 | 43 | 44 | 45 |
| p71 | 11 | 46 | 47 | 48 |
| p59 | 12 | 49 | 50 | 51 |
| 125 | 13 | 52 | 53 | 54 |
| 155 | 14 | 55 | 56 | 57 |
| 37 | 15 | 58 | 59 | 60 |
| 77 | 16 | 61 | 62 | 63 |
| 171 | 17 | 64 | 65 | 66 |
| 159 | 18 | 67 | 68 | 69 |
| p25 | 19 | 70 | 71 | 72 |
| 172 | 20 | 73 | 74 | 75 |
| 122 | 21 | 76 | 77 | 78 |
| 15 | 22 | 79 | 80 | 81 |
| p77 | 23 | 82 | 83 | 84 |
| 34 | 24 | 85 | 86 | 87 |
| 80 | 25 | 88 | 89 | 90 |
| 38 | 26 | 91 | 92 | 93 |
| 137 | 27 | 94 | 95 | 96 |
| 139 | 28 | 97 | 98 | 99 |
| p12 | 29 | 100 | 101 | 102 |

Based on the similarity of CDR1, CDR2 and CDR3, but mainly of CDR3, the nanobodies can be arranged by families, the nanobodies of a family being capable to bind the same epitope.

In addition, based on competitive ELISA assay and modelisation studies, the capacity of nanobodies to compete with each other and the epitope can be determined. The nanobodies have been arranged in groups. Nanobodies belonging to two different groups should not compete with each other for the binding to GFLV coat protein or to a GFLV coat protein VLP.

| Nanobody (Nb) | Family | Group | Epitope AA numbering of the CP as shown in SEQ ID NO: 1 |
| --- | --- | --- | --- |
| 23 | 1 | I | loop region 213-217 (ßC") of domain B of the CP in particular Thr213, Lys215, and Tyr217; ß-sheet region 371-392 of the A domain of the CP in particular Asp 372 Asn376, Val380, Ser381, Met382 and also residues Tyr217, Phe371 Ala388, Ala389, Ala392, Phe503 and Val505. |
| p75 | | | |
| 101 | | | |
| 126 | | | |
| p71 | | | |
| p59 | 2 | II | Gln16, Ala17, Asn18, Ser79, Arg80, Thr82, Ala83, |

| Nanobody (Nb) | Family | Group | Epitope AA numbering of the CP as shown in SEQ ID NO: 1 |
| --- | --- | --- | --- |
| 37 | | | Ser84, Asp86, Tyr89, Gly138, |
| 77 | | | ProProIlePhePheAspLeuThrAlaValThrAlaLeuArgSerAla |
| 171 | | | 186 to 201 |
| | | | MetValGlyThrThr 210 To 214 |
| | | | His239, Arg302, |
| | | | ThrAlaGluLeuProIleVal 322 to 328 |
| 125 | 3 | II | |
| 159 | | | |
| p25 | | | |
| 15 | 4 | IV | |
| p77 | | | |
| 34 | 5 | V | |
| 80 | | | |
| 155 | 6 | II | Ala83 |
| 172 | | | |
| 38 | 7 | VI | |
| 122 | 8 | III | Ser225, Leu228, Tyr288, Arg290, |
| | | | Pro292Ala293Arg294, |
| | | | Leu296Ala297Gly298, |
| | | | SerLeuProSerPheGlu 340 to 345 |
| | | | AspTyrPheVal 347 to 350 |
| | | | Glu384Asn385Pro386, Lys404, Arg486, Leu488 |
| 137 | 9 | VII | |
| 139 | 10 | VIII | |
| p12 | 11 | IX | |

In a preferred embodiment, one of the anti-GFLV coat protein antibodies or antibody derivatives is selected in the Group I. The group I comprises the nanobodies Nb23, Nb101, Nb126, Nbp71 and Nbp75; the antibodies or derivatives having a sequence comprising a sequence having at least 90%, 92%, 94%, 95%, 96%, 97%, 98%, 99% or more sequence identity with one nanobody among the nanobodies Nb23, Nb101, Nb126, Nbp71 and Nbp75; the antibodies or derivatives having a sequence comprising the sequences of a set of CDR1, CDR2 and CDR3 of one nanobody among the nanobodies Nb23, Nb101, Nb126, Nbp71 and Nbp75 or sequences having at least 90%, 92%, 94%, 95%, 96%, 97%, 98%, 99% or more sequence identity therewith; the antibodies or derivatives having a sequence of CDR3 of one nanobody among the nanobodies Nb23, Nb101, Nb126, Nbp71 and Nbp75 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nb23, Nb101, Nb126, Nbp71 and Nbp75 for the binding to GFLV coat protein; and the antibodies or antibody derivatives having the same epitope of a nanobody among the nanobodies Nb23, Nb101, Nb126, Nbp71 and Nbp75, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1. In a particular embodiment, the group I comprises the nanobodies Nb23, Nb101, Nb126, Nbp71 and Nbp75; the antibodies or derivatives having a sequence comprising the sequences of a set of CDR1, CDR2 and CDR3 of one nanobody among the nanobodies Nb23, Nb101, Nb126, Nbp71 and Nbp75; the antibodies or derivatives having a sequence of CDR3 of one nanobody among the nanobodies Nb23, Nb101, Nb126, Nbp71 and Nbp75 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nb23, Nb101, Nb126, Nbp71 and Nbp75 for the binding to GFLV coat protein; and the antibodies or antibody derivatives having the same epitope of a nanobody among the nanobodies Nb23, Nb101, Nb126, Nbp71 and Nbp75, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1.

In a preferred embodiment, one of the anti-GFLV coat protein antibodies or antibody derivatives is selected from the group I consisting of the nanobodies Nb23 and Nbp75; the antibodies or derivatives having a sequence comprising a sequence having at least 90%, 92%, 94%, 95%, 96%, 97%, 98%, 99% or more sequence identity with the nanobody Nb23 or Nbp75; the antibodies or derivatives having a sequence comprising the sequences of a set of CDR1, CDR2 and CDR3 of the nanobody Nb23 or Nbp75 or sequences having at least 90%, 92%, 94%, 95%, 96%, 97%, 98%, 99% or more sequence identity therewith; the antibodies or derivatives having a sequence of CDR3 of the nanobody Nb23 or Nbp75 and sequences having at least 90%, 92%, 94%, 95%, 96%, 97%, 98%, 99% or more sequence identity with CDR1 and CDR2 of the same nanobody; the antibodies or antibody derivatives competing with the nanobody Nb23 or Nbp75 for the binding to GFLV coat protein; and the antibodies or antibody derivatives having the same epitope of the nanobody Nb23 or Nbp75, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1. Optionally, one of the anti-GFLV coat protein antibodies or antibody derivatives is selected from the group consisting of the nanobodies Nb23 and Nbp75; the antibodies or derivatives having a sequence comprising the sequences of a set of CDR1, CDR2 and CDR3 of the nanobody Nb23 or Nbp75; the antibodies or derivatives having a sequence of CDR3 of the nanobody Nb23 or Nbp75 and sequences having at least 90%, 92%, 94%, 95%, 96%, 97%, 98%, 99% or more sequence identity with CDR1 and CDR2 of the same nanobody; the antibodies or antibody derivatives competing with the nanobody Nb23 or Nbp75 for the binding to GFLV coat protein; and the antibodies or antibody derivatives having the same epitope of the nanobody Nb23 or Nbp75, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1.

In a very specific embodiment, one of the anti-GFLV coat protein antibodies or antibody derivatives is selected from the group I consisting of the nanobody Nb23; the antibodies or derivatives having a sequence comprising a sequence having at least 90%, 92%, 94%, 95%, 96%, 97%, 98%, 99% or more sequence identity with Nb23; the antibodies or derivatives having a sequence comprising the sequences of a set of CDR1, CDR2 and CDR3 of the nanobody Nb23 or sequences having at least 90%, 92%, 94%, 95%, 96%, 97%, 98%, 99% or more sequence identity therewith; the antibodies or derivatives having a sequence of CDR3 of the nanobody Nb23 and sequences having at least 90%, 92%, 94%, 95%, 96%, 97%, 98%, 99% or more sequence identity with the CDR1 and CDR2; the antibodies or antibody derivatives competing with the nanobody Nb23 for the binding to GFLV coat protein; and the antibodies or antibody derivatives having the same epitope of the nanobody Nb23, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1. Optionally, one of the anti-GFLV coat protein antibodies or antibody derivatives is selected from the group consisting of the nanobody Nb23; the antibodies or derivatives having a sequence comprising the sequences of a set of CDR1, CDR2 and CDR3 of the nanobody Nb23; the antibodies or derivatives having a sequence of CDR3 of the nanobody Nb23 and sequences having at least 90%, 92%, 94%, 95%, 96%, 97%, 98%, 99% or more sequence identity with the CDR1 and CDR2; the antibodies or antibody derivatives competing with the nanobody Nb23 for the binding to GFLV coat protein; and the antibodies or antibody derivatives having the same epitope of the nanobody Nb23, in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1.

In a preferred embodiment, one of the anti-GFLV coat protein antibodies or antibody derivatives is selected in the Group II. The group II comprises the nanobodies Nbp59, Nb125, Nb155, Nb37, Nb77, Nb171, Nb159, Nbp25 and Nb172; the antibodies or derivatives having a sequence comprising a sequence having at least 90%, 92%, 94%, 95%, 96%, 97%, 98%, 99% or more sequence identity with one nanobody among the nanobodies Nbp59, Nb125, Nb155, Nb37, Nb77, Nb171, Nb159, Nbp25 and Nb172; the antibodies or derivatives having a sequence comprising the sequences of a set of CDR1, CDR2 and CDR3 of one nanobody among the nanobodies Nbp59, Nb125, Nb155, Nb37, Nb77, Nb171, Nb159, Nbp25 and Nb172 or sequences having at least 90%, 92%, 94%, 95%, 96%, 97%, 98%, 99% or more sequence identity therewith; the antibodies or derivatives having a sequence of CDR3 of one nanobody among the nanobodies Nbp59, Nb125, Nb155, Nb37, Nb77, Nb171, Nb159, Nbp25 and Nb172 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nbp59, Nb125, Nb155, Nb37, Nb77, Nb171, Nb159, Nbp25 and Nb172 for the binding to GFLV coat protein; and the antibodies or antibody derivatives having the same epitope of a nanobody among the nanobodies Nbp59, Nb125, Nb155, Nb37, Nb77, Nb171, Nb159, Nbp25 and Nb172, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1. In a particular embodiment, the group II comprises the nanobodies Nbp59, Nb125, Nb155, Nb37, Nb77, Nb171, Nb159, Nbp25 and Nb172; the antibodies or derivatives having a sequence comprising the sequences of a set of CDR1, CDR2 and CDR3 of one nanobody among the nanobodies Nbp59, Nb125, Nb155, Nb37, Nb77, Nb171, Nb159, Nbp25 and Nb172; the antibodies or derivatives having a sequence of CDR3 of one nanobody among the nanobodies Nbp59, Nb125, Nb155, Nb37, Nb77, Nb171, Nb159, Nbp25 and Nb172 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nbp59, Nb125, Nb155, Nb37, Nb77, Nb171, Nb159, Nbp25 and Nb172 for the binding to GFLV coat protein; and the antibodies or antibody derivatives having the same epitope of a nanobody among the nanobodies Nbp59, Nb125, Nb155, Nb37, Nb77, Nb171, Nb159, Nbp25 and Nb172, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1.

In a preferred embodiment, one of the anti-GFLV coat protein antibodies or antibody derivatives is selected from the group II consisting of the nanobodies Nbp59, Nb125, and Nb155; the antibodies or derivatives having a sequence comprising a sequence having at least 90%, 92%, 94%, 95%, 96%, 97%, 98%, 99% or more sequence identity with one of the nanobodies Nbp59, Nb125, and Nb155; the antibodies or derivatives having a sequence comprising the sequences of a set of CDR1, CDR2 and CDR3 of one of the nanobodies Nbp59, Nb125, and Nb155 or sequences having at least 90%, 92%, 94%, 95%, 96%, 97%, 98%, 99% or more sequence identity therewith; the antibodies or derivatives having a sequence of CDR3 of one nanobody among the nanobodies Nbp59, Nb125, and Nb155 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nbp59, Nb125, and Nb155 for the binding to GFLV coat protein; and the antibodies or antibody derivatives having the same epitope of one of the nanobodies Nbp59, Nb125, and Nb155, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1. Optionally, one of the anti-GFLV coat protein antibodies or antibody derivatives is selected from the group consisting of the nanobodies the nanobodies Nbp59, Nb125, and Nb155; the antibodies or derivatives having a sequence comprising the sequences of a set of CDR1, CDR2 and CDR3 of one of the nanobodies Nbp59, Nb125, and Nb155; the antibodies or derivatives having a sequence of CDR3 of one nanobody among the nanobodies Nbp59, Nb125, and Nb155 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nbp59, Nb125, and Nb155 for the binding to GFLV coat protein; and the antibodies or antibody derivatives having the same epitope of one of the nanobodies Nbp59, Nb125, and Nb155, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1.

In a very specific embodiment, one of the anti-GFLV coat protein antibodies or antibody derivatives is selected from the group II consisting of the nanobody Nbp59; the antibodies or derivatives having a sequence comprising a sequence having at least 90%, 92%, 94%, 95%, 96%, 97%, 98%, 99% or more sequence identity with Nbp59; the antibodies or derivatives having a sequence comprising the sequences of a set of CDR1, CDR2 and CDR3 of the nanobody Nbp59 or sequences having at least 90%, 92%, 94%, 95%, 96%, 97%, 98%, 99% or more sequence identity therewith; the antibodies or derivatives having a sequence of CDR3 of the nanobody Nbp59 and sequences having at least 90%, 92%, 94%, 95%, 96%, 97%, 98%, 99% or more sequence identity with the CDR1 and CDR2; the antibodies or antibody derivatives competing with the nanobody Nbp59 for the binding to GFLV coat protein; and the antibodies or antibody derivatives having the same epitope of the nanobody Nbp59, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1. Optionally, one of the anti-GFLV coat protein antibodies or antibody derivatives is selected from the group consisting of the nanobody Nbp59; the antibodies or derivatives having a sequence comprising the sequences of a set of CDR1, CDR2 and CDR3 of the nanobody Nbp59; the antibodies or derivatives having a sequence of CDR3 of the nanobody Nbp59 and sequences having at least 90%, 92%, 94%, 95%, 96%, 97%, 98%, 99% or more sequence identity with the CDR1 and CDR2; the antibodies or antibody derivatives competing with the nanobody Nbp59 for the binding to GFLV coat protein; and the antibodies or antibody derivatives having the same epitope of the nanobody Nbp59, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1.

In a preferred embodiment, one of the anti-GFLV coat protein antibodies or antibody derivatives is selected in the Group III. The group III comprises the nanobody Nb122; the antibodies or derivatives having a sequence comprising a sequence having at least 90%, 92%, 94%, 95%, 96%, 97%, 98%, 99% or more sequence identity with Nb122; the antibodies or derivatives having a sequence comprising the sequences of a set of CDR1, CDR2 and CDR3 of the nanobody Nb122 or sequences having at least 90%, 92%, 94%, 95%, 96%, 97%, 98%, 99% or more sequence identity therewith; the antibodies or derivatives having a sequence of CDR3 of the nanobody Nb122 and sequences having at least 90%, 92%, 94%, 95%, 96%, 97%, 98%, 99% or more sequence identity with the CDR1 and CDR2; the antibodies or antibody derivatives competing with the nanobody Nb122 for the binding to GFLV coat protein; and the antibodies or antibody derivatives having the same epitope of the nanobody Nb122, especially an epitope comprising one or several amino acids selected from the group consisting of Ser225, Leu228, Tyr288, Arg290, Pro292, Ala293, Arg294, Leu296, Ala297, Gly298, residues from Ser340 to Glu345, residues from Asp347 to Val350, Glu384, Asn385, Pro386, Lys404, Arg486, and Leu488 as shown in SEQ ID NO: 1. Optionally, one of the anti-GFLV coat protein antibodies or antibody derivatives is selected from the group consisting of the nanobody Nb122; the antibodies or derivatives having a sequence comprising the sequences of a set of CDR1, CDR2 and CDR3 of the nanobody Nb122; the antibodies or derivatives having a sequence of CDR3 of the nanobody Nb122 and sequences having at least 90%, 92%, 94%, 95%, 96%, 97%, 98%, 99% or more sequence identity with the CDR11 and CDR2; the antibodies or antibody derivatives competing with the nanobody Nb122 for the binding to GFLV coat protein; and the antibodies or antibody derivatives having the same epitope of the nanobody Nb122, especially an epitope comprising one or several amino acids selected from the group consisting of Ser225, Leu228, Tyr288, Arg290, Pro292, Ala293, Arg294, Leu296, Ala297, Gly298, residues from Ser340 to Glu345, residues from Asp347 to Val350, Glu384, Asn385, Pro386, Lys404, Arg486, and Leu488 as shown in SEQ ID NO: 1.

In one embodiment, one of the anti-GFLV coat protein antibodies or antibody derivatives is selected from the group IV. The group IV comprises the nanobodies Nb15 and Nbp77; the antibodies or derivatives having a sequence comprising a sequence having at least 90%, 92%, 94%, 95%, 96%, 97%, 98%, 99% or more sequence identity with one of the nanobodies Nb15 and Nbp77; the antibodies or derivatives having a sequence comprising the sequences of a set of CDR1, CDR2 and CDR3 of one of the nanobodies Nb15 and Nbp77 or sequences having at least 90%, 92%, 94%, 95%, 96%, 97%, 98%, 99% or more sequence identity therewith; the antibodies or derivatives having a sequence of CDR3 of one nanobody among the nanobodies Nb15 and Nbp77 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nb15 and Nbp77 for the binding to GFLV coat protein; and the antibodies or antibody derivatives having the same epitope of one of the nanobodies Nb15 and Nbp77. Optionally, one of the anti-GFLV coat protein antibodies or antibody derivatives is selected from the group consisting of the nanobodies the nanobodies Nb15 and Nbp77; the antibodies or derivatives having a sequence comprising the sequences of a set of CDR1, CDR2 and CDR3 of one of the nanobodies Nb15 and Nbp77; the antibodies or derivatives having a sequence of CDR3 of one nanobody among the nanobodies Nb15 and Nbp77 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nb15 and Nbp77 for the binding to GFLV coat protein; and the antibodies or antibody derivatives having the same epitope of one of the nanobodies Nb15 and Nbp77.

In one embodiment, one of the anti-GFLV coat protein antibodies or antibody derivatives is selected from the group V. The group V comprises the nanobodies Nb34 and Nb80; the antibodies or derivatives having a sequence comprising a sequence having at least 90%, 92%, 94%, 95%, 96%, 97%, 98%, 99% or more sequence identity with one of the nanobodies Nb34 and Nb80; the antibodies or derivatives having a sequence comprising the sequences of a set of CDR1, CDR2 and CDR3 of one of the nanobodies Nb34 and Nb80 or sequences having at least 90%, 92%, 94%, 95%, 96%, 97%, 98%, 99% or more sequence identity therewith; the antibodies or derivatives having a sequence of CDR3 of one nanobody among the nanobodies Nb34 and Nb80 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nb34 and Nb80 for the binding to GFLV coat protein; and the antibodies or antibody derivatives having the same epitope of one of the nanobodies Nb34 and Nb80. Optionally, one of the anti-GFLV coat protein antibodies or antibody derivatives is selected from the group consisting of the nanobodies the nanobodies Nb34 and Nb80; the antibodies or derivatives having a sequence comprising the sequences of a set of CDR1, CDR2 and CDR3 of one of the nanobodies Nb34 and Nb80; the antibodies or derivatives having a sequence of CDR3 of one nanobody among the nanobodies Nb34 and Nb80 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nb34 and Nb80 for the binding to GFLV coat protein; and the antibodies or antibody derivatives having the same epitope of one of the nanobodies Nb34 and Nb80.

In one embodiment, one of the anti-GFLV coat protein antibodies or antibody derivatives is selected in the Group VI. The group VI comprises the nanobody Nb38; the antibodies or derivatives having a sequence comprising a sequence having at least 90%, 92%, 94%, 95%, 96%, 97%, 98%, 99% or more sequence identity with Nb38; the antibodies or derivatives having a sequence comprising the sequences of a set of CDR1, CDR2 and CDR3 of the nanobody Nb38 or sequences having at least 90%, 92%, 94%, 95%, 96%, 97%, 98%, 99% or more sequence identity therewith; the antibodies or derivatives having a sequence of CDR3 of the nanobody Nb38 and sequences having at least 90%, 92%, 94%, 95%, 96%, 97%, 98%, 99% or more sequence identity with the CDR1 and CDR2; the antibodies or antibody derivatives competing with the nanobody Nb38 for the binding to GFLV coat protein; and the antibodies or antibody derivatives having the same epitope of the nanobody Nb38. Optionally, one of the anti-GFLV coat protein antibodies or antibody derivatives is selected from the group consisting of the nanobody Nb38; the antibodies or derivatives having a sequence comprising the sequences of a set of CDR1, CDR2 and CDR3 of the nanobody Nb38; the antibodies or derivatives having a sequence of CDR3 of the nanobody Nb38 and sequences having at least 90%, 92%, 94%, 95%, 96%, 97%, 98%, 99% or more sequence identity with the CDR11 and CDR2; the antibodies or antibody derivatives competing with the nanobody Nb38 for the binding to GFLV coat protein; and the antibodies or antibody derivatives having the same epitope of the nanobody Nb38.

In one embodiment, one of the anti-GFLV coat protein antibodies or antibody derivatives is selected in the Group VII. The group VII comprises the nanobody Nb137; the antibodies or derivatives having a sequence comprising a sequence having at least 90%, 92%, 94%, 95%, 96%, 97%, 98%, 99% or more sequence identity with Nb137; the antibodies or derivatives having a sequence comprising the sequences of a set of CDR1, CDR2 and CDR3 of the nanobody Nb137 or sequences having at least 90%, 92%, 94%, 95%, 96%, 97%, 98%, 99% or more sequence identity therewith; the antibodies or derivatives having a sequence of CDR3 of the nanobody Nb137 and sequences having at least 90%, 92%, 94%, 95%, 96%, 97%, 98%, 99% or more sequence identity with the CDR1 and CDR2; the antibodies or antibody derivatives competing with the nanobody Nb137 for the binding to GFLV coat protein; and the antibodies or antibody derivatives having the same epitope of the nanobody Nb137. Optionally, one of the anti-GFLV coat protein antibodies or antibody derivatives is selected from the group consisting of the nanobody Nb137; the antibodies or derivatives having a sequence comprising the sequences of a set of CDR1, CDR2 and CDR3 of the nanobody Nb137; the antibodies or derivatives having a sequence of CDR3 of the nanobody Nb137 and sequences having at least 90%, 92%, 94%, 95%, 96%, 97%, 98%, 99% or more sequence identity with the CDR11 and CDR2; the antibodies or antibody derivatives competing with the nanobody Nb137 for the binding to GFLV coat protein; and the antibodies or antibody derivatives having the same epitope of the nanobody Nb137.

In one embodiment, one of the anti-GFLV coat protein antibodies or antibody derivatives is selected in the Group VIII. The group VIII comprises the nanobody Nb139; the antibodies or derivatives having a sequence comprising a sequence having at least 90%, 92%, 94%, 95%, 96%, 97%, 98%, 99% or more sequence identity with Nb139; the antibodies or derivatives having a sequence comprising the sequences of a set of CDR1, CDR2 and CDR3 of the nanobody Nb139 or sequences having at least 90%, 92%, 94%, 95%, 96%, 97%, 98%, 99% or more sequence identity therewith; the antibodies or derivatives having a sequence of CDR3 of the nanobody Nb139 and sequences having at least 90%, 92%, 94%, 95%, 96%, 97%, 98%, 99% or more sequence identity with the CDR1 and CDR2; the antibodies or antibody derivatives competing with the nanobody Nb139 for the binding to GFLV coat protein; and the antibodies or antibody derivatives having the same epitope of the nanobody Nb139. Optionally, one of the anti-GFLV coat protein antibodies or antibody derivatives is selected from the group consisting of the nanobody Nb139; the antibodies or derivatives having a sequence comprising the sequences of a set of CDR1, CDR2 and CDR3 of the nanobody Nb139; the antibodies or derivatives having a sequence of CDR3 of the nanobody Nb139 and sequences having at least 90%, 92%, 94%, 95%, 96%, 97%, 98%, 99% or more sequence identity with the CDR1 and CDR2; the antibodies or antibody derivatives competing with the nanobody Nb139 for the binding to GFLV coat protein; and the antibodies or antibody derivatives having the same epitope of the nanobody Nb139.

In one embodiment, one of the anti-GFLV coat protein antibodies or antibody derivatives is selected in the Group IX. The group IX comprises the nanobody Nbp12; the antibodies or derivatives having a sequence comprising a sequence having at least 90%, 92%, 94%, 95%, 96%, 97%, 98%, 99% or more sequence identity with Nbp12; the antibodies or derivatives having a sequence comprising the sequences of a set of CDR1, CDR2 and CDR3 of the nanobody Nbp12 or sequences having at least 90%, 92%, 94%, 95%, 96%, 97%, 98%, 99% or more sequence identity therewith; the antibodies or derivatives having a sequence of CDR3 of the nanobody Nbp12 and sequences having at least 90%, 92%, 94%, 95%, 96%, 97%, 98%, 99% or more sequence identity with the CDR1 and CDR2; the antibodies or antibody derivatives competing with the nanobody Nbp12 for the binding to GFLV coat protein; and the antibodies or antibody derivatives having the same epitope of the nanobody Nbp12. Optionally, one of the anti-GFLV coat protein antibodies or antibody derivatives is selected from the group consisting of the nanobody Nbp12; the antibodies or derivatives having a sequence comprising the sequences of a set of CDR1, CDR2 and CDR3 of the nanobody Nbp12; the antibodies or derivatives having a sequence of CDR3 of the nanobody Nbp12 and sequences having at least 90%, 92%, 94%, 95%, 96%, 97%, 98%, 99% or more sequence identity with the CDR1 and CDR2; the antibodies or antibody derivatives competing with the nanobody Nbp12 for the binding to GFLV coat protein; and the antibodies or antibody derivatives having the same epitope of the nanobody Nbp12.

Preferably, the at least two or three different anti-GFLV coat protein antibodies or antibody derivatives are each selected in a different group among groups I to IX, preferably among Groups I, II and III.

In a preferred embodiment, the at least two or three different anti-GFLV coat protein antibodies or antibody derivatives comprises one anti-GFLV coat protein antibody or antibody derivative selected in the group I and one anti-GFLV coat protein antibody or antibody derivative selected in the group II; or one anti-GFLV coat protein antibody or antibody derivative selected in the group I and one anti-GFLV coat protein antibody or antibody derivative selected in the group III; or one anti-GFLV coat protein antibody or antibody derivative selected in the group II and one anti-GFLV coat protein antibody or antibody derivative selected in the group III; or one anti-GFLV coat protein antibody or antibody derivative selected in the group I, one anti-GFLV coat protein antibody or antibody derivative selected in the group II; and one anti-GFLV coat protein antibody or antibody derivative selected in the group III. Of course, the at least two or three different anti-GFLV coat protein antibodies or antibody derivatives may comprise additional anti-GFLV coat protein antibodies or antibody derivatives.

In a preferred embodiment, the at least two or three different anti-GFLV coat protein antibodies or antibody derivatives comprises:
one anti-GFLV coat protein antibody or antibody derivative selected in the group I consisting of the nanobodies Nb23 and Nbp75; the antibodies or derivatives having a sequence comprising a sequence having at least 90%, 92%, 94%, 95%, 96%, 97%, 98%, 99% or more sequence identity with the nanobody Nb23 or Nbp75; the antibodies or derivatives having a sequence comprising the sequences of a set of CDR1, CDR2 and CDR3 of the nanobody Nb23 or Nbp75 or sequences having at least 90%, 92%, 94%, 95%, 96%, 97%, 98%, 99% or more sequence identity therewith; the antibodies or derivatives having a sequence of CDR3 of the nanobody Nb23 or Nbp75 and sequences having at least 90%, 92%, 94%, 95%, 96%, 97%, 98%, 99% or more sequence identity with CDR1 and CDR2 of the same nanobody; the antibodies or antibody derivatives competing with the nanobody Nb23 or Nbp75 for the binding to GFLV coat protein; and the antibodies or antibody derivatives having the same epitope of the nanobody Nb23 or Nbp75 in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1; and one anti-GFLV coat protein antibody or antibody derivative selected in the group II consisting of the nanobodies Nbp59, Nb125, and Nb155; the antibodies or derivatives having a sequence comprising a sequence having at least 90%, 92%, 94%, 95%, 96%, 97%, 98%, 99% or more sequence identity with one of the nanobodies Nbp59, Nb125, and Nb155; the antibodies or derivatives having a sequence comprising the sequences of a set of CDR1, CDR2 and CDR3 of one of the nanobodies Nbp59, Nb125, and Nb155 or sequences having at least 90%, 92%, 94%, 95%, 96%, 97%, 98%, 99% or more sequence identity therewith; the antibodies or derivatives having a sequence of CDR3 of one nanobody among the nanobodies Nbp59, Nb125, and Nb155 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nbp59, Nb125, and Nb155 for the binding to GFLV coat protein; and the antibodies or antibody derivatives having the same epitope of one of the nanobodies Nbp59, Nb125, and Nb155, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1; or
one anti-GFLV coat protein antibody or antibody derivative selected in the group I consisting of the nanobodies Nb23 and Nbp75; the antibodies or derivatives having a sequence comprising a sequence having at least 90%, 92%, 94%, 95%, 96%, 97%, 98%, 99% or more sequence identity with the nanobody Nb23 or Nbp75; the antibodies or derivatives having a sequence comprising the sequences of a set of CDR1, CDR2 and CDR3 of the nanobody Nb23 or Nbp75 or sequences having at least 90%, 92%, 94%, 95%, 96%, 97%, 98%, 99% or more sequence identity therewith; the antibodies or derivatives having a sequence of CDR3 of the nanobody Nb23 or Nbp75 and sequences having at least 90%, 92%, 94%, 95%, 96%, 97%, 98%, 99% or more sequence identity with CDR1 and CDR2 of the same nanobody; the antibodies or antibody derivatives competing with the nanobody Nb23 or Nbp75 for the binding to GFLV coat protein; and the antibodies or antibody derivatives having the same epitope of the nanobody Nb23 or Nbp75 in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1; and one anti-GFLV coat protein antibody or antibody derivative selected in the group III consisting of the nanobody Nb122; the antibodies or derivatives having a sequence comprising a sequence having at least 90%, 92%, 94%, 95%, 96%, 97%, 98%, 99% or more sequence identity with Nb122; the antibodies or derivatives having a sequence comprising the sequences of a set of CDR1, CDR2 and CDR3 of the nanobody Nb122 or sequences having at least 90%, 92%, 94%, 95%, 96%, 97%, 98%, 99% or more sequence identity therewith; the antibodies or derivatives having a sequence of CDR3 of the nanobody Nb122 and sequences having at least 90%, 92%, 94%, 95%, 96%, 97%, 98%, 99% or more sequence identity with the CDR1 and CDR2; the antibodies or antibody derivatives competing with the nanobody Nb122 for the binding to GFLV coat protein; and the antibodies or antibody derivatives having the same epitope of the nanobody Nb122, especially an epitope comprising one or several amino acids selected from the group consisting of Ser225, Leu228, Tyr288, Arg290, Pro292, Ala293, Arg294, Leu296, Ala297, Gly298, residues from Ser340 to Glu345, residues from Asp347 to Val350, Glu384, Asn385, Pro386, Lys404, Arg486, and Leu488 as shown in SEQ ID NO: 1; or one anti-GFLV coat protein antibody or antibody derivative selected in the group II consisting of the nanobodies Nbp59, Nb125, and Nb155; the antibodies or derivatives having a sequence comprising a sequence having at least 90%, 92%, 94%, 95%, 96%, 97%, 98%, 99% or more sequence identity with one of the nanobodies Nbp59, Nb125, and Nb155; the antibodies or derivatives having a sequence comprising the sequences of a set of CDR1, CDR2 and CDR3 of one of the nanobodies Nbp59, Nb125, and Nb155 or sequences having at least 90%, 92%, 94%, 95%, 96%, 97%, 98%, 99% or more sequence identity therewith; the antibodies or derivatives having a sequence of CDR3 of one nanobody among the nanobodies Nbp59, Nb125, and Nb155 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nbp59, Nb125, and Nb155 for the binding to GFLV coat protein; and the antibodies or antibody derivatives having the same epitope of one of the nanobodies Nbp59, Nb125, and Nb155, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1; and one anti-GFLV coat protein antibody or antibody derivative selected in the group III consisting of the nanobody Nb122; the antibodies or derivatives having a sequence comprising a sequence having at least 90%, 92%, 94%, 95%, 96%, 97%, 98%, 99% or more sequence identity with Nb122; the antibodies or derivatives having a sequence comprising the sequences of a set of CDR1, CDR2 and CDR3 of the nanobody Nb122 or sequences having at least 90%, 92%, 94%, 95%, 96%, 97%, 98%, 99% or more sequence identity therewith; the antibodies or derivatives having a sequence of CDR3 of the nanobody Nb122 and sequences having at least 90%, 92%, 94%, 95%, 96%, 97%, 98%, 99% or more sequence identity with the CDR1 and CDR2; the antibodies or antibody derivatives competing with the nanobody Nb122 for the binding to GFLV coat protein; and the antibodies or antibody derivatives having the same epitope of the nanobody Nb12, especially an epitope comprising one or several amino acids selected from the group consisting of Ser225, Leu228, Tyr288, Arg290, Pro292, Ala293, Arg294, Leu296, Ala297, Gly298, residues from Ser340 to Glu345, residues from Asp347 to Val350, Glu384, Asn385, Pro386, Lys404, Arg486, and Leu488 as shown in SEQ ID NO: 1; or one anti-GFLV coat protein antibody or antibody derivative selected in the group I consisting of the nanobodies Nb23 and Nbp75; the antibodies or derivatives having a sequence comprising a sequence having at least 90%, 92%, 94%, 95%, 96%, 97%, 98%, 99% or more sequence identity with the nanobody Nb23 or Nbp75; the antibodies or derivatives having a sequence comprising the sequences of a set of CDR1, CDR2 and CDR3 of the nanobody Nb23 or Nbp75 or sequences having at least 90%, 92%, 94%, 95%, 96%, 97%, 98%, 99% or more sequence identity therewith; the antibodies or derivatives having a sequence of CDR3 of the nanobody Nb23 or Nbp75 and sequences having at least 90%, 92%, 94%, 95%, 96%, 97%, 98%, 99% or more sequence identity with CDR1 and CDR2 of the same nanobody; the antibodies or antibody derivatives competing with the nanobody Nb23 or Nbp75 for the binding to GFLV coat protein; and the antibodies or antibody derivatives having the same epitope of the nanobody Nb23 or Nbp75 in particular an epitope comprising or consisting of an epitope comprising one or several amino acids selected among the group consisting of Thr213, Lys215, Tyr217, Phe371, Asp372 Asn376, Val380, Ser381, Met382, Ala388, Ala389, Ala392, Phe503 and Val505 as shown in SEQ ID NO: 1; one anti-GFLV coat protein antibody or antibody derivative selected in the group II consisting of the nanobodies Nbp59, Nb125, and Nb155; the antibodies or derivatives having a sequence comprising a sequence having at least 90%, 92%, 94%, 95%, 96%, 97%, 98%, 99% or more sequence identity with one of the nanobodies Nbp59, Nb125, and Nb155; the antibodies or derivatives having a sequence comprising the sequences of a set of CDR1, CDR2 and CDR3 of one of the nanobodies Nbp59, Nb125, and Nb155 or sequences having at least 90%, 92%, 94%, 95%, 96%, 97%, 98%, 99% or more sequence identity therewith; the antibodies or derivatives having a sequence of CDR3 of one nanobody among the nanobodies Nbp59, Nb125, and Nb155 and sequences having at least 90%, 92%, 94%, 95%, 96%, 97%, 98%, 99% or more sequence identity with CDR1 and CDR2 of the same nanobody; the antibodies or antibody derivatives competing with one of the nanobodies Nbp59, Nb125, and Nb155 for the binding to GFLV coat protein; and the antibodies or antibody derivatives having the same epitope of one of the nanobodies Nbp59, Nb125, and Nb155, especially an epitope comprising one or several amino acids selected from the group consisting of Gln16, Ala17, Asn18, Ser79, Arg80, Thr82, Ala83, Ser84, Asp86, Tyr89, Gly138, residues from Pro186 to Ala201, residues from Met210 to Thr214, His239, Arg302 and residues from Thr322 to Val328 as shown in SEQ ID NO: 1; and one anti-GFLV coat protein antibody or antibody derivative selected in the group III consisting of the nanobody Nb122; the antibodies or derivatives having a sequence comprising a sequence having at least 90%, 92%, 94%, 95%, 96%, 97%, 98%, 99% or more sequence identity with Nb122; the antibodies or derivatives having a sequence comprising the sequences of a set of CDR1, CDR2 and CDR3 of the nanobody Nb122 or sequences having at least 90%, 92%, 94%, 95%, 96%, 97%, 98%, 99% or more sequence identity therewith; the antibodies or derivatives having a sequence of CDR3 of the nanobody Nb122 and sequences having at least 90%, 92%, 94%, 95%, 96%, 97%, 98%, 99% or more sequence identity with the CDR1 and CDR2; the antibodies or antibody derivatives competing with the nanobody Nb122 for the binding to GFLV coat protein; and the antibodies or antibody derivatives having the same epitope of the nanobody Nb12, especially an epitope comprising one or several amino acids selected from the group consisting of Ser225, Leu228, Tyr288, Arg290, Pro292, Ala293, Arg294, Leu296, Ala297, Gly298, residues from Ser340 to Glu345, residues from Asp347 to Val350, Glu384, Asn385, Pro386, Lys404, Arg486, and Leu488 as shown in SEQ ID NO: 1.

Of course, the at least two or three different anti-GFLV coat protein antibodies or antibody derivatives may comprise additional anti-GFLV coat protein antibodies or antibody derivatives.

In a particular embodiment, when the GFLV coat protein is fused in C-terminal, the at least two or three different anti-GFLV coat protein antibodies or antibody derivatives are each selected in a different group among groups II to IX, preferably among Groups II and III. Preferably, the at least two or three different anti-GFLV coat protein antibodies or antibody derivatives comprises one anti-GFLV coat protein antibody or antibody derivative selected in the group II, in particular as defined above, and one anti-GFLV coat protein antibody or antibody derivative selected in the group III, in particular as defined above.

Nanobodies typically comprise four framework regions FR1, FR2, FR3, and FR4, which may be selected e.g., from conventional FR regions of VHH polypeptides. The FR regions may, more preferably, be selected from FR1-FR4 domains having a sequence as defined below:

FR1:
(SEQ ID NO: 103)
Gln-Val-Gln-Leu-Gln-Glu-Ser-Gly-Gly-Gly-X₁-Val-

Gln-X₂-Gly-Gly-Ser-Leu-X₃-X₄-X₅-Cys-X₆-Ala-Ser-X₇-

X₈-X₉-X₁₀-X₁₁ wherein:
X₁ is a serine or an alanine residue;
X₂ is a valine, a proline or an alanine residue;
X₃ is an arginine or a lysine residue;
X₄ is a valine or a leucine residue;
X₅ is an alanine or a serine residue;
X₆ is an alanine, a glutamate or a valine residue;
X₇ is a glycine, a glutamate or a threonine;
X₈ is an aspartate, a tyrosine, a leucine or an isoleucine;
X₉ is a threonine, a valine, a proline, an arginine or an isoleucine;
X₁₀ is a phenylalanine, a proline, a serine, a tyrosine, a leucine, a histidine, an alanine or a threonine; and
X₁₁ is a serine, a glutamate, an asparagine, or an arginine.

FR2:
(SEQ ID NO: 104)
Trp-Phe-Arg-Gln-Ala-Pro-Gly-Lys-X₁-Arg-Glu-Gly-

Val-Ala wherein:
X₁ is a glycine or a glutamate residue;

FR3:
(SEQ ID NO: 105)
Arg-Phe-Thr-Ile-Ser-Lys-Asp-Asn-Ala-Asp-Asn-X₁-

Met-Tyr-Leu-Glu-Met-Asn-X₂-Leu-Lys-Pro-Glu-Asp-

Thr-Ala-Ile-Tyr-Tyr-Cys-Ala-Ala wherein:
X₁ is a isoleucine or a methionine residue; and
X₂ is a serine or a glycine residue; and/or FR4:
(SEQ ID NO: 106)
Trp-Gly-Gln-Gly-Thr-Gln-Val-Thr-Val-Ser-Ser.

As an alternative, the one skilled in the art may graft the CDRs within a universal scaffold of VHH described in the state in the art (Saerens et al., *J. Mol. Biol.* (2005) 352, 597-607), so as to obtain the desired nanobody against GFLV. The nanobody of the invention may be a VHH comprising a universal framework scaffold, for instance as shown in Saerens et al. and comprising at least one CDR, preferably three CDRs, having a sequence comprising a sequence having at least 90%, 92%, 94%, 95%, 96%, 97%, 98%, 99% or more sequence identity with CDR1, CDR2 and/or CDR3 from a nanobody selected from the group I, II, III, IV, V, VI, VII, VIII and IX.

An object of the invention thus relates to a nanobody selected from the groups II to XI as defined above, in particular from the groups II and III as defined above. In particular, the nanobody is selected from the group consisting of the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12, the antibodies or derivatives having a sequence comprising a sequence having at least 90%, 92%, 94%, 95%, 96%, 97%, 98%, 99% or more sequence identity with one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12; the antibodies or derivatives having a sequence comprising the sequences of a set of CDR1, CDR2 and CDR3 of one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 or sequences having at least 90%, 92%, 94%, 95%, 96%, 97%, 98%, 99% or more sequence identity therewith; the antibodies or derivatives having a sequence of CDR3 of one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 for the binding to GFLV coat protein; and the antibodies or antibody derivatives having the same epitope of a nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12. The present invention also relates to a VLP comprising GFLV coat proteins and a nanobody selected from the groups II to XI as defined above, in particular from the groups II and III as defined above.

An object of the invention thus relates to a combination of at least two nanobodies which are each selected in a different group among groups I to IX as defined above, preferably among Groups I, II and III as defined above.

Nanobodies can be prepared by standard production, isolation and purification methods or by recombinant or synthesis technology. For example, anti-GFLV nanobodies can be generated e.g. by immunization of a camelid animal with purified GFLV particles or from naïve synthetic libraries and selected by methods known by the person skilled in the art, such as phage display. Camelids encompass dromedary, camel llama and alpaca. For instance, in order to generate a library of VHHs displayed on bacteriophages, the skilled artisan can refer to Muydermans et al., *Molecular Biotechnology*, 2001, 74, 277-302, in particular to the section entitled Recombinant VHH, the disclosure of which being incorporated therein by reference. Alternatively, nanobody can derived from a cartilaginous fish such as nurse shark (*Ginglymostoma cirratum*) and wobbegong shark (*Orectolobus maculates*). The skilled artisan may refer to Dooley et al. *Mol Immunol*, 2003, 40:25-30 which describes the selection and characterization of naturally occurring single-domain (IgNAR) antibody fragments from immunized sharks by phage display.

The DNA molecule encoding said nanobodies can be determined or isolated or cloned by methods well-known in the art. Nanobodies having specific sequences as defined above can be produced by artificial synthesis or recombinant DNA technology. Nanobodies may then be tested for their ability to bind GFLV and variant thereof or to compete with any particular nanobodies as described in the examples.

The invention also relates to a nucleic acid molecule comprising a nucleotide sequence encoding a nanobody, antibody or antibody derivative as defined above. The nucleic acid may be DNA or RNA, single- or double-stranded. The nucleic acid may further comprise regulatory domains (e.g., a promoter or terminator sequence). The nucleic acid may be cloned in suitable cloning or expression vectors, such as plasmids, viruses, cosmids, phages, etc. The present invention further relates to a nucleic acid encoding a nanobody as defined above and any expression vector or cell host suitable for producing the nanobody.

The compound may be linked to the anti-GFLV coat protein antibodies or antibody derivatives through known techniques such as genetic fusion, chemical coupling, affinity binding via affinity tags (such as Strep tag or PolyHis Tag), for instance, that cause covalent or non-covalent coupling. A preferred way is by genetic fusion or chemical coupling, most preferably by genetic fusion when the compound is a polypeptide. In a particular embodiment, the compound is coupled to the ligand at an end of the ligand, most preferably covalently, such as by genetic fusion or chemical coupling. Such coupling does not substantially affect or prevent binding of the anti-GFLV coat protein antibodies or antibody derivatives to the virus coat protein or particle.

In a particular embodiment, the compound fused to an antibody is a protein. Noteworthy, the advantage of producing antibodies conjugated or fused to a compound compared GFLV coat protein fused to a compound in C-ter for the expression of the compound at the external surface of the viral capsid is that the production pathway may differ for these two types of constructions. Indeed, the compound fused to GFLV coat protein would be produced and assemble in the cytoplasm of production cells, where post-translational modifications such as N-glycosylation will not occur. On the contrary, compound fused to antibody may go through endoplasmic reticulum and N-glycosylation.

Also, compared to the conjugation of a compound to the GFLV coat protein, the use of antibodies allows to increase the display number of compounds at the outer surface of the VLP. Indeed, compound conjugated to GFLV coat protein enables the display of 60 compounds (as the GFLV capsid is made of 60 coat protein subunits) whereas the use of two non-competitive antibodies enables the display of up to 120 compounds and the use of three non-competitive antibodies enables the display of up to 180 compounds at the outer surface of GFLV VLPs.

Antibodies may recognize epitopes that are present on each coat protein subunit that forms the VLP but also may recognize epitopes formed by the association of coat proteins to form the viral capsid. It is known that icosahedral capsid may present epitopes formed from one coat protein subunit or from the association of two, three or five coat proteins, leading to symmetry axis of order 1, 2, 3 and 5. For a capsid formed by 60 subunits of coat protein such as GFLV which has a pseudo T=3 icosahedral capsid, epitopes defined by symmetry axis of order 1 will be present 60 times on the surface of the viral capsid (i.e. one antibody per coat protein subunit), epitopes defined by symmetry axis of order 2 will be present 30 times (i.e. one antibody at the junction of two coat protein subunits), epitopes defined by symmetry axis of order 3 will be present 20 times (i.e. one antibody at the junction of three coat protein subunits) and epitopes defined by symmetry axis of order 5 will be present 12 times (i.e. one antibody at the junction of five coat protein subunits, e.g. on the top of pentamer forming the vertices of the icosahedra). This characteristic is of great importance for antigen presentation and vaccination purposes, as it is known that the increase of antigen content and presentation increase the probability of an immune response. Accordingly, the at least two antibodies of the invention are non-competitive antibodies that each binds epitopes that are defined by one coat protein subunit, i.e. present 60 times on the GFLV VLP, meaning that the at least two non-competitive antibodies bind at least 120 epitopes on the outer surface of the VLP.

In a preferred embodiment, the invention thus relates to GFLV virus-like particles comprising or obtainable from GFLV coat proteins, wherein said particles comprise at least one compound of interest conjugated to the coat protein by attachment mediated by the at least two or three anti-GFLV coat protein antibodies or antibody derivatives. Such compound is exposed at the surface of the particles. The particle may have several distinct compounds exposed on its surface through conjugation with the same or distinct anti-GFLV coat protein antibodies or antibody derivatives. In a preferred embodiment, conjugation is performed using anti-GFLV coat protein antibodies or antibody derivatives, coupled to the compound, even more preferably using a nanobody.

In another preferred embodiment, the invention relates to GFLV virus-like particles comprising or obtainable from GFLV coat proteins, wherein said particles comprise an encaged compound conjugated to the N-ter of the coat protein, and an exposed compound, conjugated to the surface of the particle by attachment mediated by anti-GFLV coat protein antibodies or antibody derivatives, more preferably by at least two or three different anti-GFLV coat protein antibodies or antibody derivatives, even more preferably by at least two or three different anti-GFLV coat protein nanobodies. Preferably, said least two or three different anti-GFLV coat protein antibodies or antibody derivatives, preferably nanobodies, do not compete with each other for the binding to the GFLV coat protein.

In one embodiment, the invention relates to a VLP comprising a GFLV coat protein and at least two different anti-GFLV coat protein antibodies or antibody derivatives, said antibodies or antibody derivatives being conjugated, preferably covalently conjugated, to compounds, preferably different compounds. In particular, the VLP may comprise a first anti-GFLV coat protein antibody or antibody derivative conjugated to a first compound, a second anti-GFLV coat protein antibody or antibody derivative conjugated to a second compound, and optionally a third anti-GFLV coat protein antibody or antibody derivative conjugated to a third compound. Optionally, the VLP may comprise a GFLV coat protein fused to another compound at the N-terminal end.

An object of the invention thus relates to a compound covalently conjugated to a nanobody selected from the groups II to XI as defined above, in particular from the groups II and III as defined above. In particular, the nanobody is selected from the group consisting of the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12, the antibodies or derivatives having a sequence comprising a sequence having at least 90%, 92%, 94%, 95%, 96%, 97%, 98%, 99% or more sequence identity with one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12; the antibodies or derivatives having a sequence comprising the sequences of a set of CDR1, CDR2 and CDR3 of one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 or sequences having at least 90%, 92%, 94%, 95%, 96%, 97%, 98%, 99% or more sequence identity therewith; the antibodies or derivatives having a sequence of CDR3 of one nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 and sequences having at least 90%, 92%, 94%, 95%, 96%, 97%, 98%, 99% or more sequence identity with CDR1 and CDR2 of the same nanobody; the antibodies or antibody derivatives competing with a nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12 for the binding to GFLV coat protein; and the antibodies or antibody derivatives having the same epitope of a nanobody among the nanobodies Nb37, Nb77, Nb77, Nb171, Nbp59, Nb125, Nb159, Nbp25, Nb15, Nbp77, Nb34, Nb80, Nb155, Nb172, Nb38, Nb122, Nb137, Nb139, and Nbp12.

An object of the invention thus relates to a combination or composition comprising at least two nanobodies covalently conjugated to a compound which can be the same or different for each nanobody and which are each selected in a different group among groups I to IX as defined above, preferably among Groups I, II and III as defined above.

Another object of the invention relates to a combination or composition comprising at least two or at least three nanobodies conjugated, preferably covalently conjugated, to a compound which can be the same or different for each nanobody, each nanobody being selected in a different group among groups I to IX as defined above, preferably among Groups I, II and III.

The inventors surprisingly observed that some antibodies are capable of increasing the stability of the GFLV capsid. In particular, the nanobody Nb23 is capable of dramatically increasing the stability of the GFLV capsid. By stabilization it is meant that the capsid shape and function is more strongly conserved or that the disruption of the viral capsid needs more stringent conditions to occur in the presence of the antibodies bound on the outer surface of the VLP compared to the VLP without antibodies. For example, stability of the GFLV capsid can be assessed by measuring the effect of temperature on GFLV capsid without any antibody compared to GFLV capsid bound to antibodies. Such effect can be measured by Thermal shift assay that quantifies the change in thermal denaturation temperature of a protein under varying conditions, as described in the examples below. By "increase" is meant that the temperature at which 50% of the maximal fluorescent signal is reached is increased by at least 2° C., preferably at least 3° C., more preferably at least 5° C., even more preferably 10° C. The Thermal shift assay is detailed in the example section.

Accordingly, at least one of the at least two or at least three nanobody selected in the group I, II and III stabilizes the GFLV capsid. Even more preferably, one of the at least two or at least three nanobody is a nanobody from the group I that stabilizes the GFLV capsid. Particularly, one of the at least two or at least three nanobody is the nanobody Nb23.

Particularly, the invention relates to a combination or composition comprising at least two or three nanobodies covalently conjugated to a compound which can be the same or different for each nanobody and which are each selected in a different group among groups I to IX as defined above, preferably among Groups I, II and III as defined above, where the nanobodies chosen do not compete which each other and/or each of the at least two or three nanobodies recognized an epitope present 60 times on the outer surface of the viral particle, and/or at least one of the at least two or three nanobody stabilizes the GFLV capsid.

According to a further alternative embodiment, chemical conjugation to VLPs can be contemplated, such as conjugation through an exposed sulfhydryl group (Cys), attachment of an affinity tag (i.e. 6 Histidine, Flag Tag, Strep Tag, SpyCatcher etc.) to the particles for subsequent binding of compounds, or incorporation of unnatural amino acids into the VLP and compound for click chemistry conjugation.

Compounds

The compound for use in a conjugate or VLP of the invention may be any compound of interest, such as a therapeutic, diagnostic, targeting or imaging agent. The compound may also be a tag, allowing subsequent attachment of any agent of interest by exposing the conjugated coat protein or VLP to said agent under suitable conditions.

In a particular embodiment, the compound is a chemical entity of biological interest such as a small chemical molecule (e.g., antibiotic, antiviral, immunomodulator, antineoplastic, etc.), a peptide or polypeptide (such as a cytokine, a hormone, a toxin, an antigen), a protein (such as an enzyme, an antibody (such as a nanobody) or a part of an antibody), a nucleic acid (e.g., a dsRNA, siRNA, miRNA), or a marker (such as a fluorescent or luminescent agent).

In a particular embodiment, the compound is a protein, polypeptide or peptide. With such type of compound, the conjugates of the invention can be produced by genetic fusion.

Other examples of such compounds include, for instance peptide or protein antigens. Such compounds are typically conjugated to the anti-GFLV coat protein antibodies or antibody derivatives, so as to allow their exposure at the surface of a resulting particle. In this manner, the conjugate or resulting VLP can be used as a therapeutic or prophylactic vaccine or immunogenic composition, to induce or stimulate an immune response against the antigen.

Another example of such compounds includes peptides or proteins with affinity to metal or tracer molecules such as gadolinium, silver, gold etc.

Another example are compounds that allows to evade the immune system such as protein A from *Staphylococcus aureus*, protein G from Streptococcal bacteria, or peptides that are markers or Self such as peptides derived from CD47.

Another example of such compounds includes toxins, enzymes or toxic molecules which should preferably not be exposed in the organism before they have reached their target tissue.

Examples of such toxic compounds include, for instance, caspases, the cytosine deaminase and uracil phospho-ribosyltransferase Fcy and Fur, ribosome inactivating proteins, and bacterial and plant toxins, which act by inhibiting protein synthesis in eukaryotic cells. The toxins of the Shiga and ricin family inactivate 60S ribosomal subunits by an N-glycosidic cleavage, which releases a specific adenine base from the sugar-phosphate backbone of 28S rRNA. Members of the family include shiga and shiga-like toxins, and type I (e.g. trichosanthin and luffin) and type II (e.g. ricin, agglutinin and abrin) ribosome inactivating proteins (RIPs). All these toxins are structurally related. RIPs have been of considerable interest because of their potential use, conjugated with monoclonal antibodies, as immunotoxins to treat cancers. Further, trichosanthin has been shown to have potent activity against HIV-1-infected T cells and macrophages.

Another example of such compounds includes cell targeting ligands. Such compounds allow specific or targeted binding to cell receptors or structures, thus allowing targeting of the conjugate or VLP to a preferred target cell or tissue. Examples of such targeting ligands include ligands of cell surface receptors, or receptors of cell surface proteins, or antibodies (such as nanobodies) or fragments thereof.

Another example of such compounds includes cell-penetrating peptides and transduction domains. Such compounds allow internalization of conjugate or VLP in the cell. Examples of such peptides include tat peptide of HIV-1.

In one embodiment, the present invention relates to a VLP comprising a GFLV coat protein conjugated with at least two or three different anti-GFLV coat protein antibodies or antibody derivatives, wherein at least one anti-GFLV coat protein antibody or antibody derivative is conjugated to a protein, polypeptide or peptide. With such type of compound, the conjugates of the invention can be produced by genetic fusion or chemical conjugation to an antibody, preferably to a nanobody.

In a particular embodiment, the compound fused to the anti-GFLV coat protein nanobody is a protein, polypeptide or peptide that has a size of at least 1.5 times the size of the nanobody (i.e. about at least 22 kDa), a size of at least twice the size of the nanobody (i.e. about at least 30 kDa), a size of at least 3 times the size of the nanobody (i.e. about at least 45 kDa) or a size of at least 4 times the size of the nanobody (i.e. about at least 60 kDa).

In a particular embodiment, the compound fused to the anti-GFLV coat protein nanobody is a protein, polypeptide or peptide that has a diameter of at least twice the diameter of the nanobody (i.e. about at least 5 nm), a diameter of at least 3 times the diameter of the nanobody (i.e. about at least 10 nm), a diameter of at least 4 times the diameter of the nanobody (i.e. about at least 15 nm) or a diameter of at least 5 times the diameter of the nanobody (i.e. about at least 20 nm). By diameter it is meant the mean diameter of a protein, polypeptide or peptide when considered as a globular compound.

In a particular embodiment, the present invention relates to a VLP comprising a GFLV coat protein conjugated at least two or three different anti-GFLV coat protein antibodies or antibody derivatives, wherein at least one anti-GFLV coat protein antibody or antibody derivative is conjugated to a targeting ligand. Preferably, the GFLV coat protein can be conjugated at the N-term end to a toxic compound, in particular a cytotoxic compound such as those used in the treatment of cancer. Such conjugate allows formation of a VLP having the targeting ligand exposed at the surface and the toxic compound encaged. Alternatively, the toxic compound may be conjugated to another anti-GFLV coat protein antibodies or antibody derivatives, thereby allowing the targeted delivery of the toxic compound.

In another particular embodiment, the present invention relates to a VLP comprising a GFLV coat protein and at least two or three different anti-GFLV coat protein antibodies or antibody derivatives, said at least two or three different anti-GFLV coat protein antibodies or antibody derivatives being conjugated to antigens, which can be the same or different, more preferably which are different. In the context of three different anti-GFLV coat protein antibodies or antibody derivatives conjugated to three different antigens, the resulting VLP may expose up to 60 copies of each antigen at the surface of the VLP. In the context of three different anti-GFLV coat protein antibodies or antibody derivatives conjugated to the same antigen, the resulting VLP may expose up to 180 copies of the antigen at the surface of the VLP.

The antigen may be chosen a viral, bacterial, fungal, parasite or cancer antigen.

As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In exemplary embodiments the bacterial antigen is derived from a bacterium selected from the group consisting of *Lysteria* species, in particular *Lysteria monocytogenese; Helicobacter* species, in particular *Helicobacter pyloris; Borelia* species, in particular *Borelia burgdorferi; Legionella* species, in particular *Legionella pneumophilia; Mycobacteria* s species, in particular *M. tuberculosis, M. avium, M. intracellulare, M. kansasii, M. gordonae; Staphylococcus* species, in particular *Staphylococcus aureus; Neisseria* species, in particular *N. gonorrhoeae, N. meningitidis; Listeria* species, in particular *Listeria monocytogenes; Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue; Bacillus* species, in particular *Bacillus anthracis; Corynebacterium* species, in particular *Corynebacterium diphtheriae; Erysipelothrix* species, in particular *Erysipelothrix rhusiopathiae; Clostridium* species, in particular *C. perfringens, C. tetani; Enterobacter* species, in particular *Enterobacter aerogenes, Klebsiella* species, in particular *Klebsiella* 1*S pneumoniae, Pasteurella* species, in particular *Pasteurella multocida, Bacteroides* species; *Fusobacterium* species, in particular *Fusobacterium nucleatum; Streptobacillus* species, in particular *Streptobacillus moniliformis; Treponema* species, in particular *Treponema pertenue*; *Leptospira*; pathogenic *Escherichia* species; and *Actinomyces* species, in particular *Actinomyces israelii*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses, Zika virus, West Nile virus); Coronaviridae (e.g., coronaviruses such as SARS (Severe acute respiratory syndrome) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus (RSV), especially human respiratory syncytial virus, metapneumovirus, especially human metapneumovirus (hMPV)); Orthomyxoviridae (e.g., influenza viruses such as H5N1, H7N9, H9N2); Bunyaviridae (e.g., Hantaan viruses, bunya viruses, phleboviruses and Nairo viruses, Crimean-Congo hemorrhagic fever (CCHF)); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses), alphavirus (chikungunya virus). Alternatively, a viral antigen may be produced recombinantly.

As used herein, the terms "cancer antigen" and "tumour antigen" are used interchangeably and refer to antigens that are differentially expressed by cancer cells and can thereby be exploited in order to target cancer cells. Cancer antigens are antigens which can potentially stimulate apparently tumour-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumour viruses. The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumour antigens, GAGE-family of tumour antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvß3 integrins, α5ß1 integrins, αIIbß3-integrins, PDGF beta receptor, SVE-cadherin, IL-8, hCG, IL-6, IL-6 receptor, IL-15, α-fetoprotein, E-cadherin, α-catenin, ß-catenin and γ-catenin, p120ctn, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

As used herein, the term "parasite antigen" includes, but is not limited to, antigen from parasites such as P. falciform proteins such as CSP (circumsporozoite protein), AMA-1 (apical membrane antigen-1), TRAP/SSP2 (sporozoite surface protein 2, LSA (liver stage antigen), Pf Exp 1 (Pf exported protein 1), SALSA (Pf antigen 2 sporozoite and liver stage antigen), STARP (sporozoite threonine and aspar-agins-rich protein).

Methods for Preparing VLPs

The invention also relates to a method of producing a conjugated molecule as defined above, comprising providing a GFLV coat protein or anti-GFLV coat protein antibody or antibody derivative, and conjugating said protein or antibody to a compound. In a particular embodiment, providing a GFLV coat protein or anti-GFLV coat protein antibody or antibody derivative comprises expressing a nucleic acid construct encoding said protein or antibody in a host cell or an in vitro expression system, and collecting the expressed protein or antibody. Subsequently, the protein or antibody may be conjugated to a compound. In an alternative route, the conjugated protein or antibody is expressed directly using a recombinant fusion nucleic acid. In this regard, in a particular embodiment, the invention relates to a method of producing a conjugated molecule as defined above comprising providing a nucleic acid construct encoding said molecule and expressing said nucleic acid in a host cell or an in vitro expression system. Recombinant production may be performed in any suitable host such as plant cells, in planta, in bacteria, yeasts, insects, CHO or other eukaryotic cells or in an in vitro transcription system. The expressed conjugate may be collected and stored as free molecules in any suitable medium or state. It may also be allowed to assemble into VLPs, which can then be collected and stored under suitable conditions.

Further objects of the invention also reside in a nucleic acid molecule (e.g., DNA, RNA) encoding a molecule as defined above; a vector comprising such a nucleic acid; and a host cell containing such a nucleic acid or vector.

The invention also provides a method of producing virus-like particles according to the present invention. The method comprises (i) providing a GFLV coat protein, optionally conjugated to a compound, (ii) allowing said GFLV coat protein, alone or in mixture with other proteins, to assemble into virus-like particles, and (iii) coupling the particles of (ii) to at least two different anti-GFLV coat protein antibodies or antibody derivatives as disclosed in the present document.

In a typical embodiment, the GFLV coat proteins are maintained under conditions allowing self-assembly into particles. Such conditions include in solution at a pH comprised typically between 5 and 9, more typically between 6 and 8, and at a temperature comprised between 4° C. and 50° C., more preferably around room temperature.

The GFLV coat protein may be provided by artificial synthesis, enzymatic production/assembly, purification, and/or recombinant technology. In this respect, in a preferred embodiment, the method comprises:

providing a nucleic acid construct encoding a GFLV coat protein, optionally conjugated to a compound, expressing said nucleic acid in a host cell or an in vitro expression system, optionally purifying the GFLV coat protein, forming VLPs from the expressed and optionally purified GFLV coat proteins, and collecting or purifying the VLPs.

In a particular embodiment, the method comprises a further step of adding to the VLPs the at least two or three different anti-GFLV coat protein antibodies or antibody derivatives, optionally conjugated to a compound. Particularly, the method comprises a further step of adding to the VLPs at least two or three different anti-GFLV coat protein antibodies.

Preferably, the antibodies chosen do not compete which each other and/or each of the at least two or three antibodies recognized an epitope present 60 times on the outer surface of the GFLV capsid, and/or at least one of the at least two or three antibody stabilizes the GFLV capsid.

In another particular embodiment, the step of forming the VLP is performed in the presence the at least two or three different anti-GFLV coat protein antibodies or antibody derivatives.

In the above methods, recombinant production may be performed in any suitable host such as plant cells, in planta, in bacteria, yeasts, CHO or other eukaryotic system or in an in vitro transcription system.

The VLPs may be collected and purified by conventional techniques such as, for instance, chromatography, centrifugation, and the like. Because VLPs are stable under physiological conditions, they may be stored in solution or frozen or lyophilized, according to conventional techniques.

Pharmaceutical Compositions and Methods

The invention also relates to a pharmaceutical composition comprising at least one VLP as defined above and, preferably, one or more pharmaceutically acceptable excipients. The invention also relates to a pharmaceutical composition comprising a VLP comprising a GFLV coat protein and at least two different anti-GFLV coat protein antibodies or antibody derivatives as defined above and, preferably, one or more pharmaceutically acceptable excipients. Preferably, the antibody derivatives are antibodies chosen to not compete which each other and/or each of the at least two or three antibodies recognized an epitope present 60 times on the outer surface of the GFLV capsid, and/or at least one of the at least two or three antibodies stabilizes the GFLV capsid. Even more preferably, the antibody derivatives are nanobodies genetically fused to a compound as described above.

Depending on the presence or absence, and on the nature of a compound or active group bound to the GFLV coat protein or the anti-GFLV coat protein antibodies or antibody derivatives, the compositions of the invention may have various utilities such as therapeutic compositions, vaccines, adjuvants, diagnostic compositions, immunogenic compositions, research samples, etc.

The compositions of the invention advantageously comprise a pharmaceutically acceptable vector or excipient. The pharmaceutically acceptable excipient can be selected from any suitable and conventional excipient, depending on the form of the composition. In particular, for solid compositions such as tablets, pills, powders, or granules, the composition may comprise e.g., lactose, dextrose, sucrose, mannitol, or sorbitol. A lubricant, such as talc or stearic acid, a binder, such as starch or gelatin, a disintegrant such as agar, and/or a sweetener may be further added to the composition as well. For semi-solid compositions, the excipient can, for example, be an emulsion or oily suspension. Liquid compositions, in particular injectable or those included in a soft capsule, can include a diluent or solvent such as, for example, water, physiological saline solution, aqueous dextrose, an alcohol, an oil and analogues thereof.

The compositions or conjugates of the invention can be administered by any suitable route such as, without limitation, by parenteral (e.g., subcutaneous, intravenous or intramuscular route), oral, rectal, ocular or intranasal routes. The pharmaceutical compositions typically comprise an effective dose of a VP or conjugate or compound, e.g., any dose that gives a therapeutic effect for a given condition and administration schedule.

Depending on the nature of the compound conjugated to the coat protein, the VLPs and compositions of the invention can be used for treating, preventing, diagnosing or imaging various pathologies.

In this respect, the invention relates to VLPs as defined above for use as a medicament. It also related to the use of VLPs as defined above for the manufacture of a medicament. It also relates to a method for treating a disease in a subject comprising administering a therapeutic effective amount of VLPs as defined above to said subject.

The invention relates to VLPs as defined above for use as a vaccine. It also related to the use of VLPs as defined above for the manufacture of a vaccine. It also relates to a vaccine composition comprising VLPs as defined above.

The invention relates to VLPs as defined above for use as an adjuvant or immunomodulator.

The invention relates to VLPs as defined above for use as a diagnostic agent. The invention relates to VLPs as defined above for use as a tracer.

Further aspects and advantages of the invention will be disclosed in the following experimental section, which shall be considered as illustrative.

EXAMPLES

A. Experimental Procedures

Construction of Binary Plasmids

Coding sequences for GFLV-$CP_{F13}$, TagRFP and EGFP were amplified by PCR using Phusion high fidelity DNA polymerase according to the manufacturer's instructions (New England Biolabs, Thermo Fisher Scientific, Massachusetts) using pVec2ABC (Viry et al., 1993; Schellenberger et al., 2010; Vigne et al., 2013), pTagRFP-C (Evrogen, Russia) and pEGFP-N1 (Clontech, Calif.) as templates, respectively. The translational fusions TRCP and CPTR, corresponding respectively to N- or C-terminal fusions of GFLV-$CP_{F13}$ with TagRFP, were obtained by overlapping PCRs (Ho et al., 1989) using above described PCR products as templates and overlapping primers encoding the $Gly_3$-

Ser-Gly$_3$ peptide linker sequence. The attB-flancked CP, TR, CPTR and TRCP PCR products were cloned by Gateway recombination into the pDONR/Zeo entry vector (Invitrogen, Thermo Fisher Scientific, Massachusetts) and further recombined into the pEAQ-HT-DEST1 binary plasmid (Sainsbury et al., 2009). For CPEG, in which the C-terminus of GFLV-CP$_{F13}$ is fused to EGFP, a pDONR$^T$M/Zeo vector containing the CP coding sequence devoid of stop codon was used for cloning by recombination in a homemade Gateway expression vector deriving from the pEAQ-HT-DEST1 (Sainsbury et al., 2009) vector by the introduction of the EGFP encoding sequence (Clontech, Calif.) downstream of the attR2 recombination site. Recombination resulted in the introduction of the DPAFLYKVVRSFGPA linker peptide between GFLV-CP$_{F13}$ C-terminal residue and EGFP (FIG. 1 and List of sequences). Sequences of Nanobodies derived constructs can be found in WO2015/110601.

Immunization, Nanobodies Library Construction and Screening

GFLV-specific single domain antibodies Nanobodies (Nbs) were generated according to Ghassabeh, Saerens and Muyldermans. Briefly, a camel (*Camelus dromedarius*) was injected 6 times subcutaneously at weekly intervals with 100 µg of purified GFLV according to standard immunization protocols. After immunization, total RNA was extracted from isolated peripheral blood lymphocytes and mRNAs reverse transcribed to cDNA. The region encoding variable fragments of heavy chain antibodies were then amplified with two subsequent PCR, cloned into the pHEN4 phagemid vector (10) and transformed into *E. coli* TG1 cells. The resulting Nbs library was screened by phage display for GFLV-specific binders in three consecutive biopanning rounds against 10 µg of purified GFLV each. Sequences of GFLV-specific Nbs were obtained following the isolation of individual clones from the enriched library by a phage-ELISA approach performed against 100 ng of purified GFLV.

Plant Material, Virus Infection and Virus-Like Particles Production

*C. quinoa* and *N. benthamiana* plants were grown in greenhouses at 22/18° C. (day/night) temperatures. GFLV-CP$_{F13}$ infectious crude sap derived from pMV13+ pVec$_{Acc65I}$2ABC-infected material (Schellenberger et al., 2010) was used to mechanically inoculate a large number of three weeks old *C. quinoa* plants. Plant were harvested 14 days post-inoculation and used for virus purification. For mechanical inoculations of *N. benthamiana*, three weeks old plants were inoculated with purified GFLV-CP$_{F13}$. VLPs were produced by transient expression after agro-infiltration of *N. benthamiana* leaves. Binary plasmids were introduced by electroporation and maintained in *Agrobacterium tumefaciens* strain GV3101:pMP90. Cultures were grown to stable phase in Luria-Bertani media with appropriated antibiotics, pelleted and then resuspended in sterile water, alone or in a 1:1 ratio for coexpression, to a final optical density of 0.5 at 600 nm. Suspensions were infiltrated into four weeks old *N. benthamiana* leaves with 2 ml plastic syringes. Healthy, infected and agro-infiltrated *N. benthamiana* plants were maintained in a growth chamber set at 14/10 photoperiod (4800 1x) with a temperature setting of 21/18° C. (day/night) for 7 days before leaf harvesting.

Agro-Infiltrated-Leaves Observation

Fluorescent proteins visualisation was realised 5 days post-agro-infiltration. Leaves were imaged with an Axio-Zoom V16 macroscope (Zeiss, Germany) using excitation and emission wavelength filters of 450-490 nm and 500-550 nm for EGFP imaging and of 625-655 nm and 665-715 nm for TagRFP visualization. Images were processed using ImageJ (Schneider et al., 2012) and GNU Image Manipulation Program (GIMP, see Worldwide Website: gimp.org) softwares.

DAS-ELISA

Healthy, infected and agro-infiltrated leaves were grinded at 1:5 w/v ratio in HEPES 100 mM pH8 and clarified for 5 min at 3000 g. GFLV or VLPs detection was performed using commercial DAS-ELISA kit (Bioreba, Switzerland) according the manufacturer's instructions. Briefly, plates were coated with polyclonal anti-GFLV antibodies diluted in coating buffer at 1:1000 dilution, incubated with clarified extracts before the addition of anti-GFLV monoclonal antibodies coupled to alkaline phosphatase at 1:1000 dilution in conjugate buffer. Three washings were done between each step of the DAS-ELISA procedure. Detection was realised using para-nitrophenylphosphate as substrate that produces a yellow water-soluble reaction product in alkaline media. Absorbance at 405 nm was measured with the Titertek Multiscan MCC/340 reader (Labsystems, France). Samples were considered to be positive when the absorbance values exceed the control samples by at least a factor of three after substrate incubation period.

Competitive ELISA Assessment of Nanobodies Against GFLV Particles

GFLV or VLP detection was performed using a homemade DAS-ELISA kit using different strep-tagged nanobodies (Nb-ST) or fused to Alkaline Phosphatase protein (Nb-AP). Briefly, plates were coated directly with purified GFLV particles diluted at a 1:1000 in coating buffer, incubated with strep-tagged nanobodies (Nb23:ST, Nb75:ST, Nbp59:ST, Nb125:ST or Nb122:ST) at a 1:100 dilution in conjugate buffer before addition of anti-GFLV nanobodies fused to AP (Nb75:AP, Nbp59:AP or Nb155:AP) at a 1:500 dilution in conjugate buffer. Competition assessment of tested nanobodies on viral epitopes was performed by challenging two Nb:STs versus same Nbs fused to AP in each ELISA test. Detection was realized using para-nitrophenylphosphate (PNPP) and absorbance at 405 nm measured with a Titertek Multiskan MCC/340 reader (Labsystems).

Negative Staining, Immunocapture and Immunosorbent Electron Microscopy (ISEM)

Healthy, infected and agro-infiltrated leaves were grinded in 100 mM pH 8 HEPES buffer, clarified by centrifugation at 3000 g for 5 min and either processed for simple negative staining, for immunocapture or for ISEM. For all the grids, negative staining was performed on 300 mesh nickel grids covered with carbon-coated Formvar (Electron Microscopy Science, Pennsylvania) by incubation with 1% ammonium molybdate solution for 90 sec. For immunocaptures performed on clarified saps, grids were coated with polyclonal antibodies (Bioreba, Switzerland) at 1:100 dilution, incubated with plant extracts for 2 h at 4° C., washed in HEPES 25 mM pH 8 buffer and finally processed for negative staining. For ISEM on purified CP, CPTR and TRCP VLPs, grids were coated with homemade monoclonal antibodies against GFLV at a 0.05 mg/mL concentration and incubated with VLPs for 1 h at room temperature. After blocking with 2% w/v BSA, 10% v/v normal goat serum, 0.05% Triton-X100 in 22.5 mM HEPES pH 8, grids were further incubated with either anti-GFLV (Bioreba, Switzerland) at 1:100 dilution or anti-TR polyclonal antibodies at 0.01 mg/mL concentration (Evrogen, Russia) for 1 h at room temperature. Immunogold labelling was performed using anti-rabbit antibodies conjugated to 10 nm colloidal gold particles at 1:50 dilution (British Biocell International, Wales). Washes with 25 mM pH 8 HEPES buffer were done between all steps.

ISEM on purified CPEG and CPEG+TRCP VLPs were performed in a similar manner except that polyclonal antibodies against GFLV (Bioreba, Switzerland) were used for capture and either home-made monoclonal antibodies mix against GFLV or monoclonal anti-EG antibodies (Roche, Germany) employed for detection. Finally, immunogold labelling was performed using anti-mouse antibodies conjugated with 10 nm colloidal gold particles (British Biocell International, Wales). Observations were realised using a Philips EM208 transmission electron microscope. Film-based photographs were acquired onto Kodak Electron Image Films SO-163 (Electron Microscopy Science, Pennsylvania) and revealed with the adapted chemicals (Electron Microscopy Science, Pennsylvania). Finally, photographs were scanned to obtain digital electron microscope images and processed using GNU Image Manipulation Program (GIMP, see Worldwide Website: gimp.org).

GFLV-CP Structure Representation and Analysis

CP subunit and capsid representations were made using the previously 3 Å resolved GFLV-F13 atomic structure (PDB ID: 4V5T, Schellenberger, Sauter, et al., 2011) with the UCSF Chimera package (Pettersen et al., 2004). The CP subunit ends accessibility data were obtained using VIPERdb (Carrillo-Tripp et al., 2009).

Virus and Virus-Like Particles Purification

GFLV was purified from *N. benthamiana* infected-plants according to Schellenberger et al., (2011a). VLPs were purified from agro-infiltrated *N. benthamiana* leaves following the same experimental procedure. Briefly, a minimum of 1000 g of leaves were ground in extraction buffer, the resulting extract was filtered, incubated with bentonite and finally clarified by centrifugation for 15 min at 1,900 g. VLPs were precipitated from clarified sap by adding PEG-20,000 and sodium chloride and further processed by centrifugation on a sucrose cushion pH 9 followed by a sucrose density gradient fractionation. Two mL fractions were collected from which aliquots at 1:500, 1:5,000 and 1:10,000 dilutions were processed for a semi-quantitative DAS-ELISA to identify GFLV- or VLP-enriched fractions that were further pooled before final ultracentrifugation at 290,000 g for 2 hours. After resuspension in HEPES 25 mM pH 9, VLPs were quantified by DAS-ELISA (Vigne et al., 2013) using purified GFLV as a standard.

Expression and Purification of NbsST from *E. coli*

GFLV-specific Nbs coding sequences were sub-cloned into the pHEN6 (Conrath et al., 2001) expression vector as a BstEII/PstI fragment adding a N-terminal pelB signal sequence for periplasmic targeting and a C-terminal 6-His-tag for purification. Production of 6-His-tagged Nbs constructs was performed by expression in freshly transformed *E. coli* WK6 cells grown in Terrific Broth (TB) medium and induced overnight with 1 mM isopropyl-BD-thiogalactopyranoside (IPTG) at 28° C. (Thys et al., 2010).

An additional C-terminal Strep-tag II (Trp-Ser-His-Pro-Gln-Phe-Glu-Lys) was added for Nbs use in ELISA. To do so, Nbs coding sequences were amplified by PCR and amplicons introduced by Gateway cloning into the pDONR/Zeo vector (Invitrogen) which was further recombined into the pOGWA expression vector (Busso et al., 2005). Large-scale production of Strep II tagged Nbs constructs was performed by expression in freshly transformed *E. coli* BL21 (DE3) cells grown overnight at 23° C. in auto-inducing ZYP 50502 medium (Studier, 2005).

Nbs were extracted from periplasm by osmotic shock (Habib et al., 2013) and purified at 4° C. by immobilized metal ion chromatography (IMAC) on a 1 ml Protino Ni-NTA column [Macherey-Nagel] using 500 mM imidazole in running buffer (50 mM Tris, 300 mM NaCl, 5% glycerol, pH 8.0) for elution, followed by size exclusion chromatography (SEC) on a Hiload 16/60 Superdex75 prep grade column (GE Healthcare Life Science) in 1× phosphate buffer saline (PBS) (Conrath et al., 2001; Thys et al., 2010). Purity of eluted proteins was assessed by Coomassie blue staining of denatured Nbs that migrate as single bands of ca. 15 kDa in Tris-tricine polyacrylamide gel. Purification yields were estimated from absorbance at 280 nm based on extinction coefficients computed from Nbs amino acid composition.

Expression and Nbs:EGFP Chromobodies Purification from *E. coli*

EGFP:6his and Nbs sequences were amplified by PCR using Phusion high fidelity DNA polymerase according to the manufacturer's instructions (New England Biolabs). EGFP:6his was amplified from pEAQ:GFP vector with BamHI/XhoI flanking restriction sites and Nbs sequences were amplified with NdeI/BamHI flanking restriction sites. PCR fragment were digested with restriction enzymes according to the manufacturer's instructions, and cloned into the pET-22b (+) expression vector (Novagen). Expression was performed in freshly transformed *E. coli* SHuffle T7 Express cells (New England Biolabs) grown in TB medium at 30° C. until the culture reach an O.D=0.8-1 then protein production is induced overnight with 0.1 mM IPTG at 20° C. 41. Pelleted cells resuspended in running buffer (50 mM Tris, 300 mM NaCl, 5% glycerol, pH 7.4) were lysed by sonication (100% amplitude for 2 min with 13 mm diameter probe, Vibra-Cell VCX 500 (Sonics)) and purification of cytoplasmic extract by IMAC follow by SEC was carried out as indicated above. The purity of the eluted protein was assessed by Coomassie blue staining of denatured Nbs:EGFP that migrate as a band of 43 kDa in Tris-tricine polyacrylamide gel upon electrophoresis.

Expression and Purification of Nbs:ALP from *E. coli*

Alkaline phosphatase:6his (AP:6his) and Nbs sequences were amplified by PCR using Phusion high fidelity DNA polymerase according to the manufacturer's instructions (New England Biolabs). AP:6his was amplified from pLIP6 vector with BamHI/XhoI flanking restriction sites and Nbs sequences were amplified with NdeI/BamHI flanking restriction sites. PCR fragment were digested with restriction enzymes according to the manufacturer's instructions, and cloned into the pET-22b (+) expression vector (Novagen). Expression was performed in freshly transformed *E. coli* BL21 expression strain (New England Biolabs) grown in TB medium at 37° C. until the culture reach an O.D=0.8-1 then protein production is induced overnight with 0.1 mM IPTG at 20° C. 41. Nbs were extracted from periplasm by osmotic shock 41 and purified at 4° C. by immobilized metal ion chromatography (IMAC) on a 1 ml Histrap HP Ni-NTA column (GE Healthcare) using 500 mM imidazole in running buffer (50 mM Tris, 300 mM NaCl, 5% glycerol, pH 8.0) for elution. The purity of the eluted protein was assessed by Coomassie blue staining of denatured Nbs:AP:6his that migrate as a band of 60 kDa in Tris-tricine polyacrylamide gel upon electrophoresis. ALP or AP or PAL refers to alkaline phosphatase.

SDS-Page Electrophoresis, Western-Blot and Mass Spectrometry

For SDS-Page analysis, 6 µg of GFLV-particles equivalent from each purified sample were separated on an 8% acrylamide gel and stained with Coomassie blue using Instant Blue (Expedeon, England). For mass spectrometry, SDS-Page bands of interest were excised and proteins destained, reduced, alkylated, trypsin-digested overnight, chemotrypsin-digested and finally processed for nanoLC-MSMS analysis on a nanoU3000 (Dionex, Thermo Fisher Scientific, Massachusetts)-ESI-MicroTOFQII (Bruker, Mass.). Mass spectrometry data were analysed with the help of Mascot (Matrix Science Limited, England) and Proteinscape (Bruker, Mass.). For Western-Blot analyses, 0.05 μg of each sample were resolved on an 8% acrylamide gel and denatured proteins electrotransferred onto Immobilon PVDF membranes. Membranes were incubated either with rabbit polyclonal anti-GFLV antibodies at a 1:1000 dilution or with commercial polyclonal anti-TR antibodies (Evrogen, Russia) at a 1:5000 dilution. Proteins were revealed by chemiluminescence after incubation with goat anti-rabbit conjugated to horseradish peroxidase at a 1:12500 dilution (Thermo Fisher Scientific, Massachusetts) and Lumi-Light solution (Roche, Germany). Images were taken with a G:Box imaging system (Syngene, England), analysed with GeneTools (Syngene, England) and finally processed with GIMP (see Worldwide Website: gimp.org).

Single-Particle Epifluorescence Microscopy

Purified particles from TRCP, CPEG or CPEG+TRCP samples were diluted in HEPES 25 mM pH8 in order to obtain individual spots upon imaging on an inverted epifluorescence microscope Axio Abserver Z1 (Zeiss, Germany) equipped with an Orca Flash4.0 camera (Hamamatsu, Japan) and Spectra X light engine (Lumencor, Oreg.). Excitation and emission wavelength filters were 455-495 nm and 505-555 nm for EGFP and of 532.5-557.5 nm and 570-640 nm for TagRFP. Images were finally processed using ImageJ (Schneider et al., 2012) and GIMP softwares (see Worldwide Website: gimp.org).

Native Agarose Gel Electrophoresis

Native gel electrophoresis of purified virions and VLPs was performed in 1% w/v agarose gels in 1.0×TA buffer (20 mM TrisBase, 0.06% v/v acetic acid) pH 9. For nucleic-acids detection, 5 μg of virus particles or VLPs were diluted in loading buffer (10% v/v glycerol, HEPES 25 mM pH 9) supplemented with ethidium bromide (EtBr) at 0.1 μg/mL. After electrophoretic separation, the EtBr-prestained gel was first processed for nucleic-acid content using the Gel Doc system (Bio-Rad) equipped with a 302 nm excitation source and a 520-640 nm band-pass emission filter before processing for Coomassie blue staining as mentioned previously. For fluorescence imaging, 3 μg of purified VLPs were diluted in loading buffer and native gel electrophoresis performed in the absence of EtBr. Imaging was done with Ettan™ DIGE Imager imaging system (GE healthcare) equipped with bandpass excitation (380-650 nm) and emission (465-695 nm) filters for EG visualization. TR visualization was realized upon 480-540 nm excitation and 590-660 nm band-pass emission filtering.

Modeling

The crystal structures of GFLV (PDBid 4V5T), EG (PDBid 1GFL) and TR (PDBid 3M22) were used to model the CPEG, TRCP or TRCPEG VLPs. Chimeric CPs were created with Modeller (Eswar et al., 2006) by appending the linker and corresponding FP sequences to the free C- and N-terminal ends of the CP pointing outside and inside the VLP, respectively. Full capsids were reconstituted using the icosahedral symmetry in PyMOL (The PyMOL Molecular Graphics System, Version 1.7.4 Schrödinger, LLC). The position of the FP in the TRCP capsid was adjusted to avoid steric clashes using Coot (Emsley et al., 2010). Chimeric CPs were created with Modeller (Webb et al., 2014) by appending the linker and corresponding FP sequences to the free C- and N-terminal ends of the CP pointing outside and inside the VLP.

Accession Code

Cryo-EM map and coordinates of the atomic model can be found in the Protein Data Bank (PDB) and the Electron Microscopy Data Bank (EMD) under the following accession numbers, respectively: PDB (5foj), EMD-3246.

Docking by pyATTRACT

The ATTRACT docking program was used to dock Nbp59 and Nb122 to GFLV coat protein. pyATTRACT is implemented as a Python script using the pTools library. The docking protocol was applied as described in Zacharias (2005) Proteins: Structure, Function, and Bioinformatics 60, 252-256) and Saladin et al., (2009). PTools: an opensource molecular docking library. BMC structural biology 9, 27.

Briefly, pyATrRACT performs systematic docking without using any experimental data concerning the native complex. This algorithm relies on minimization of the interaction energy, the ligand (mobile partner) being placed at regular positions/orientations around the receptor surface (fixed partner) at a distance slightly larger than its biggest dimension. For each starting position, about 250 initial ligand orientations are generated. For each starting geometry, energy minimization (quasi-Newton minimizer) is performed using transitional and rotational degrees of freedom of the ligand. The top-ranking solution is very close to the X-ray structure. Different Python scripts are provided with the ATTRACT program to set up the input files needed by the pyATTRACT docking script. The procedure of script analysis was followed as described in Saladin et al., (2009). PTools: an opensource molecular docking library. BMC structural biology 9, 27.

Dynamic Light Scattering (DLS).

Mean particle diameters and polydispersity of TRCP VLP alone or complexed to Nb23 to Nb23:EGFP or to Nb23:ALP was estimated by DLS using a Zetasizer NanoZS (Malvern) and Nanostar (Wyatt). Five successive measurements were performed using three independent virus and protein preparations with virus at 0.1 mg/ml in Tris buffer (50 mM Tris, 100 mM NaCl, pH 8.3), Nb23 at 0.2 mg/ml, Nb23:EGFP at 0.5 mg/ml and Nb23:ALP at 1 mg/ml. Scattered intensities were recorded at 20° C. and data processed with DTS software (version 6.01) or DYMAMICS (version 7.1.8.93), respectively. All particles were monodisperse. ALP or AP PAL refers to alkaline phosphatase.

Thermal Shift Assay

In a ThermoFluor thermal shift assay, the capsid-stabilizing properties of the VHHs were investigated. GFLV (final concentration, 100 μg/ml) was exposed to increasing temperatures in the presence or absence of Nb23 at a final concentration of 10 μM. All of the samples were prepared in PBS buffer and SYBR green II RNA gel stain (Life Technologies). SYBR green II is a fluorescent dye that emits green light only when bound to nucleic acids. During heating of GFLV particles, the capsid is destabilized and RNA is released. The samples were gradually heated from 30 to 84° C. (steps of 0.4° C., one step per second). Because of the temperature sensitivity of the SYBR green II fluorescence, the temperature was changed to 30° C. after each step to measure the fluorescent signal. For each sample and control, the temperature at which 50% of the maximal fluorescent signal was reached was determined, using Graph Pad Prism.

Microscale Thermophoresis (MST)

Microscale thermophoresis (MST) measurements were performed using a Monolith NT115 (NanoTemper Technologies GmbH, Germany). The concentration of the fluorescent VLP was kept constant at a concentration of 100 nM, while the concentration of Nb23 was varied from 0.07 nM-1.0 µM. Samples were diluted in MST optimized buffer (20 mM TRIS-HCL buffer, pH=9.5). Each experiment consisted of 15-point titration series in which the Nb concentrations were generated as a 1:1 dilution of VLP. For the measurement, 10 µL of the different dilutions of samples were filled into hydrophilic treated capillaries (premium coated capillaries, NanoTemper technologies, Germany) and measured after a 10 min equilibration at room temperature. The measurements were performed (n=3) at 40% LED, and 20%, 40%, and 80% MST power. Laser-On time was 30 sec, Laser-Off time 5 sec. MST Analysis data of each VLP vs Nb experiment was loaded into PALMIST (biophysics.swmed.edu/MBR/software.html) and evaluated using the appropriate model (1:1) according to Scheuermann et al. (2016) *Analytical biochemistry* 496, 79-93.

B—Results

1. GFLV Coat Protein Self-Assembles into Virus-Like Particles

To address the ability of GFLV coat protein (CP) to produce VLPs in planta, the sequence encoding the CP of GFLV isolate F13 (SEQ ID NO: 1 with no N-ter methionine) was introduced in the pEAQ-HT-DEST1 binary vector (Sainsbury et al., 2009) (FIG. 1) and used for transient expression in *Nicotiana benthamiana* leaves upon agroinfiltration. Samples were analysed by direct double-antibody sandwich ELISA (DAS-ELISA) at 7 days post agroinfiltration (dpi) using as positive control *N. benthamiana* leaves from GFLV-F13 infected plants at 14 days post-inoculation (dpi), and as negative controls pEAQ-HT-DEST1-driven TagRFP (TR, Merzlyak et al., 2007) agroinfiltrated leaves at 7 dpi and healthy leaves. A strong positive signal was detected in both CP-expressing and GFLV-infected samples but not in extracts from TR-infiltrated or healthy leaf material (FIG. 2a). To test the ability of transiently expressed CP to self-assemble into VLPs, the same leaf extracts were further analysed by transmission electron microscopy (TEM) after immunocapture on grids using as capture antibodies, the same polyclonal antibodies than used for coating in DAS-ELISA. Observation of negatively stained material (FIG. 2b) revealed the presence of icosahedral particles of about 30 nm in diameter in CP expressing samples but not in TR-infiltrated or healthy negative controls (FIG. 2b). Although not very abundant on grids, icosahedral particles seen in CP-expressing crude samples were very similar to GFLV-F13 particles observed under identical conditions (FIG. 2b). This indicates that GFLV CP is able to self-assemble into VLPs upon transient expression in *N. benthamiana*.

2. GFLV CP Maintains its Capacity to Assemble into VLPs Upon Fusion of its N- or C-Terminal Ends to Foreign Proteins Analysis of the GFLV atomic structure (Schellenberger et al. 2011b) reveals that the GFLV CP amino-terminal residue $Gly_1$ and the three carboxy-terminal residues $Phe502$, $Pro_{503}$ and $Val504$ do not contribute to the final quaternary structure of the virus capsid and are exposed at the inner and outer surfaces of the GFLV particle, respectively (FIGS. 3a and 3b). In this respect, both extremities were tested for the addition of extra residues and their impact of the capacity of the CP to form a capsid. To test this hypothesis, N- or C-terminal CP fusions to TR were produced and, respectively, named TRCP (SEQ ID NO: 3) and CPTR (SEQ ID NO: 2) hereafter (FIG. 1). Both fusions included a Gly3-Ser-Gly3 linker peptide (FIG. 1) to maintain flexibility between the CP and TR domains (Zilian and Maiss, 2011) and were transiently expressed in *N. benthamiana* leaves. Samples were analysed by epifluorescence macroscopy for TR expression at 5 dpa (FIG. 4), and 2 days later by DAS-ELISA for CP expression (FIG. 3c) and TEM for VLPs (FIG. 3d). While TR fluorescence was observed in all samples (FIG. 4) suggesting proper expression of the different proteins, CP was detected only in CPTR and TRCP crude extracts by DAS-ELISA (FIG. 3c), which correlated with the presence of VLPs as seen upon TEM (FIG. 3d). These results suggest that GFLV CP retains its capacity to form VLPs upon fusion of its N- or C-terminal end to TR.

To confirm our results and to gain insights into the biochemical properties of such VLPs, large-scale production in *N. benthamiana* leaves was carried out followed by purification using standard GFLV purification procedure that includes clarification and ultracentrifugation steps in the absence of protease inhibitors (see methods). In parallel, GFLV-$CP_{F13}$ virions were purified from infected *C. quinoa* leaves at 14 dpi. After linear sucrose gradient, a sharp pink band was observed in the TRCP gradient (FIG. 5a) as well as a faint pink band in the CPTR gradient (not shown), but not in infected samples (not shown). 2 mL sucrose gradient fractions were collected and those enriched in VLPs identified by semi-quantitative DAS-ELISA. While bona fide GFLV particles sedimented towards the bottom of the gradient in fractions 8-10, other particles (CP, CPTR and TRCP) located to the lighter fractions 3-5, 4-6 and 6-8, respectively (FIG. 5b). This is in agreement with previous report indicating that empty GFLV particles purified from infected plants display lower density than native RNA-containing virions (Quacquarelli et al., 1976). DAS-ELISA positive fractions were further pooled and processed for final concentration by ultracentrifugation. Remarkably, pink pellets were observed in both TRCP and CPTR samples (FIG. 6a). The final concentration of purified material (FIG. 6b) was determined by quantitative DAS-ELISA using purified GFLV-$CP_{F13}$ virions as a standard. Yields ranged from 386 to 445 µg GFLV-particles equivalent per kg of fresh leaves for the three purifications which is in the same order of magnitude than GFLV purification yields from infected *N. benthamiana* (Schellenberger, Demangeat, et al., 2011).

To assess their quality and purity, purified samples were analysed by Coomassie blue staining after SDS-PAGE (FIG. 6c), immunoblotting using anti-GFLV or anti-TR antibodies (FIGS. 6d and 6e) and mass spectrometry (data not shown). For Coomassie blue staining, 6 µg of particles equivalent of each sample were loaded on SDS-denaturing gel. In agreement with the purification of VLPs, one major protein with an observed mass of 57 kDa and co-migrating with the CP of GFLV (calculated mass 56 kDa) was present in purified samples from CP-expressing leaves (FIG. 6c, bands 1 and 2). For CPTR and TRCP samples, profiles were more complex with three major proteins of observed molecular mass of approximately 87, 73 and 57 kDa being detected (FIG. 6c, bands 3-5 for CPTR and 6-8 for TRCP) but in inverse proportions: the larger product being the most abundant and the shorter being the least abundant for TRCP (respectively approximately 69%, 24% and 7% respective abundance), the opposite for CPTR (respectively approximately 2%, 35% and 63%). Upon immunoblotting with anti-GFLV antibodies, the shorter product present in CPTR sample (FIG. 6c, band 5) was clearly revealed (FIG. 6d), strongly suggesting that band 5 corresponds to the CP of GFLV and probably represents a cleavage product of CPTR. In the TRCP sample, the larger product (FIG. 6c, band 6) immunoreacted clearly with anti-GFLV antibodies (FIG. 6d). Considering this band is about the expected size of TRCP (calculated mass: 82.8 kDa), our results suggest that the full-length TRCP is the principal protein present in the purified TRCP sample. Accordingly, band 6 gave also a strong signal upon immunodetection with anti-TR antibodies (FIG. 6e). Anti-TR antibodies immunoreacted also but weakly with the larger product present in the CPTR sample (band 3) and with the 73 kDa truncated products observed in CPTR and TRCP samples (FIG. 6e). Altogether our results suggest that the principal proteins present in purified TRCP and CPTR samples are derived from GFLV CP and thus likely represent VLPs.

To gain insights into the composition of the purified products, Coomassie-stained bands were subjected to mass spectrometry analysis leading to the identification of peptides covering nearly the entire CP for all bands analysed (FIG. 6c, data not shown). Peptides corresponding to TR were only observed for bands 3, 4, 6 and 7 and nearly full-coverage of the CPTR or TRCP proteins strictly restricted to bands 3 and 6. The 73 kDa products corresponding to band 4 and 7 displayed only partial coverage of the TR and thus represent truncated version of CPTR or TRCP, possibly due to proteolytic degradation during the purification process carried out in the absence of protease inhibitors. Altogether our results demonstrate that the full-length chimeric protein CPTR or TRCP can be purified following standard virus purification procedures and are therefore fully compatible with VLPs production. They also reveal that the CPTR fusion is more labile than TRCP, possibly as a consequence of a different orientation of TR towards the internal or external surface of VLPs upon N- or C-terminal fusion, respectively.

3. N- and C-Terminal CP Fusions are Oriented Towards the Interior or Exterior of VLPs, Respectively.

To gain insights into the orientation of N- and C-terminal CP fusions, VLPs were further subjected to negative staining and immuno-sorbent electron microscopy analyses. As expected, direct coating of purified material onto nickel grids followed by negative staining revealed the presence of numerous VLPs in all samples (FIGS. 7d, 7g and 7j) that clearly resembled GFLV particles (FIG. 7a). Under such conditions, CP and CPTR particles appeared electron-dense (FIGS. 7d and 7g) similarly to GFLV-virions (FIG. 7a). In contrast, TRCP particles were electron-lucent (FIG. 7j), possibly reflecting the orientation of TR toward the interior of the TRCP VLPs that is likely to increase the inner density of particles and decrease the penetrability to heavy metals (FIGS. 7a and 7b). To verify these hypotheses, decoration assays were performed with anti-GFLV (FIGS. 7b, 7e, 7h and 7k) or anti-TR antibodies (FIGS. 7c, 7f, 7i and 7l). While all purified particles were labelled with anti-GFLV antibodies as expected (FIGS. 7b, 7e, 7h and 7k), only CPTR particles were decorated with anti-TR antibodies (FIG. 7i), in spite of the significantly greater proportion of full-length chimeric protein present in TRCP versus CPTR particles (FIG. 6). This clearly demonstrates that CPTR and TRCP are both compatible with VLP formation that differ however in architecture. In CPTR VLPs, TR is accessible to anti-TR antibodies, highlighting the exposure of the protein towards the outer surface of particles. In contrast, in TRCP VLPs, TR is totally inaccessible to anti-TR antibodies, most likely as a consequence of the encaging of TR inside the particles. Perhaps most importantly, our results also clearly show that GFLV CP can accommodate the fusion of foreign proteins as large as fluorescent proteins that represent 50% of its own length without altering the capacity of the protein to self-assemble into VLPs.

4. Hybrid VLPs can be Produced

In view of our results, the capacity of GFLV CP to form hybrid VLPs upon co-expression of N- and C-terminal CP fusions was tested. To do so, EGFP was selected as reporter protein and fused to the CP N-terminus as indicated in FIG. 1 (construct CPEG, SEQ ID NO: 4). As before, agro-infiltrated N. benthamiana leaves were used for expression assays and purification of VLPs carried out in the absence of protease inhibitors. CPEG expressing leaves were used as negative control and compared to leaves coexpressing CPEG and TRCP (CPEG+TRCP). In compliance with our previous results, CPEG VLPs could be purified and located to the same linear sucrose gradient fractions than CPTR VLPs (FIG. 5b). Coexpressed CPEG and TRCP also enabled the purification of DAS-ELISA immunoreactive material cosedimenting with CPEG VLPs in linear sucrose gradient (FIG. 5b). ISEM analysis confirmed the presence of VLPs in both CPEG and CPEG+TRCP samples that clearly immunoreacted with both anti-GFLV and anti-EGFP antibodies (FIG. 8), well in agreement with the predicted exposure of EGFP towards the external surface of VLPs. Considering TR is inaccessible to antibodies in ISEM upon fusion to the CP N-terminus, the inventors further assessed the presence of EGFP and TagRFP by fluorescence imaging of VLPs separated by electrophoresis on a native agarose gel (FIG. 9). Under such conditions, distinct bands with specific migration profiles were detected in TRCP, CPEG and CPEG+TRCP samples, TRCP VLPs being visible only in the red channel ($\lambda_{excitation}$ 480-540/$\lambda_{emission}$ 590-660 nm, FIG. 9a), CPEG VLPs only in the green channel ($\lambda_{excitation}$ 450-485/$\lambda_{emission}$ 510-540 nm, FIG. 9b) and CPEG+TRCP VLPs emitting in both channels as expected for hybrid particles (FIGS. 9a and 9b, empty arrowheads).

To confirm the production of bonafide hybrid VLPs and hence the presence of particles that emit simultaneously in green and red, purified samples were further processed for single particle imaging by epifluorescence microscopy. In this manner, numerous TRCP VLPs were observed that appeared as individual spots emitting only in the red channel (FIG. 9c). Similarly, individual spots emitting only in the green channel and corresponding to CPEG VLPs were also detected but in lower density (FIG. 9d), likely reflecting the low abundance of full-length protein in purified CPEG VLPs samples (FIG. 6c). Importantly, a mix of separately purified CPEG and TRCP VLPs led to the observation of individual VLPs that were always exclusively either red or green (FIG. 9e). In contrast, yellow particles were clearly detected in CPEG+TRCP VLPs (FIG. 9f, filled arrowheads). Altogether, our results demonstrate that GFLV CP is fully compatible with the production of hybrid VLPs in which exogenous proteins as large as fluorescent proteins can be simultaneously exposed to the outer surface and encaged in the inner lumen of individual VLPs pending their fusion to either the N- or C-terminus of the CP.

5. The GFLV VLPs are Free from Nucleic Acids

To examine the content of the VLPs, native agarose gel electrophoresis was performed and gel stained either with Coomassie blue for protein content (FIG. 10a) or with ethidium bromide (EtBr) for nucleic acids (FIG. 10b). As already noticed upon fluorescence imaging of VLPs in native agarose gels (FIGS. 9a and 9b), the migration profiles of CP, CPTR and TRCP VLPs as well as purified GFLV differed significantly (FIG. 10a), probably as a consequence of difference in net charges, density and mass of the various particles. Possibly due to the rather labile nature of TagRFP when exposed at the outer surface of particles, CPTR VLPs formed a smear on the gel rather than a clear band as seen with other samples (FIG. 10a). Under UV-illumination after EtBr staining, nucleic acids were clearly detected in GFLV virions and below detectable level in CP VLPs, suggesting that such particles are, within the limits of detection of this assay, nucleic acid-free (FIG. 10b). In contrast, under identical conditions, both CPTR and the TRCP VLPs generated a weak signal likely as a consequence of the slight TR protein excitation under UV illumination (Merzlyak et al., 2007) and the use of filters incompatible with the full discrimination of TR and nucleic acid spectra rather than to the presence of nucleic acids (FIG. 10b, arrowheads). In this respect, only purified virus led to high $O.D._{260}/O.D._{280}$ values compatible with the presence of nucleic acids, whereas those measured for the different VLPs (CP, CPTR, TRCP, CPEG and CPEG+TRCP) ranged from 0.89 to 1.07 indicative of their very low or nucleic acid-free content (FIG. 10c).

6. GFLV CP-Derived VLPs are Compatible with the Simultaneous Encapsidation and Exposure of Up to 120 FPs To estimate the maximum number of FPs that could be incorporated in VLPs upon genetic fusion to the CP, CPEG- and TRCP-derived particles were modelled (see experimental procedures). Both fusions turned out to be fully compatible with the formation of VLPs (FIG. 11). According to our models, CPEG that includes the gateway-derived linker peptide leads to the formation of VLPs with an apparent diameter of 48.5 Å in which the FP is evenly distributed and floating at the particle outer surface (FIG. 11a). In contrast, TRCP results in the formation of VLPs with an outer diameter of 29.0 Å identical to the one of virions, but in which the FP forms a tightly packed layer inside particles (FIG. 11b). The inventors also modelled TRCPEG (SEQ ID NO: 30), a theoretical CP (1000 residues) in which both termini are fused to FPs (FIG. 11c) revealing that, at least in silico, GFLV CP is compatible with the simultaneous encapsidation and exposure of FPs, representing altogether 120 FP per VLP. The calculated mass of such a TRCPEG VLP (6.69 MDa) is nearly twice that of a CP-only VLP (3.37 MDa).

7. Nanobodies are Versatile Tools for the Display of Foreign Proteins at the Surface of GFLV CP-Derived VLPs Nb23 which has been described in WO2015/110601 can efficiently bind to purified GFLV particles allowing the structure of the GFLV-Nb23 complex to be determined by single particle cryo-electron microscopy at 2.8 Å resolution (FIG. 12; Cryo-EM map and coordinates of the atomic model have been deposited under pdb accession code 5FOJ). The structure reveals that Nb23 binds at the surface of GFLV in the vicinity of the 5-fold axis (FIGS. 12a and 12b). The outer isocontour surface of the GFLV-Nb23 reconstruction (FIGS. 12a and 12b) shows that the Nb23 molecules are positioned far enough from each other allowing 60 of them to attach per virion and reach full 1:1 stoichiometric binding with the CP without bridging neighboring CPs.

The interaction region essentially involves residues of the complementarity determining regions (CDR) 3 and CDR2 of Nb23, as well as the two neighboring CP domains A and B (2 out of the 3 jellyroll ß-sandwiches of the CP) that jointly form a composite binding site with two core interacting regions denoted 1 and 2, adding up to a large total interaction surface of ~1100 Å$^2$ indicative of a stable complex. Within these regions, a high level of specific interactions between the capsid and the antibody is provided through a series of hydrogen bonds. Region 1 comprises loop region 212-216 (ßC") of domain B of the CP in which Thr212 interacts with Asp100$_{Nb23}$, Lys214 forms hydrogen bonds with the carbonyl backbone of Ile 102$_{Nb23}$, and Tyr216 interacts with the backbone of Leu104Nb2$_3$ and forms hydrophobic contacts with Leu104$_{Nb23}$. Region 2 comprises the two strands of the capsid ß-sheet region 370-391 (domain A of the CP) in which Asp371 forms a salt bridge with Arg55Nb23 and Asn375 interacts with Thr58$_{Nb23}$. An additional anchor point of the antibody is provided through Lys65$_{Nb23}$). In the second ß-strand of the 370-391 region, the backbone of Val379 interacts with Thr110$_{Nb23}$, and the Ser380 backbone and Met381 form hydrophobic contacts with Ser109$_{Nb23}$ and Trp108$_{Nb23}$, respectively. The CDR3 forms a long loop with a short α-helical turn carrying Leu104$_{Nb23}$ which is accommodated within a hydrophobic pocket formed by Phe502, Val504, Tyr216, Phe370 and an alanine cluster formed by residues 387, 388 and 391. Phe370 provides π-stacking interactions with the side-chain of Trp108$_{Nb23}$, which deeply inserts into the binding site within a cavity formed at the junction of the A and B domains of the CP. Finally, the C-terminal Phe502 and Val504 residues form hydrophobic contacts with Tyr107$_{Nb23}$, Trp108$_{Nb23}$ and Leu104$_{Nb23}$. Taken together, the cryo-EM structure provides a precise mapping of the Nb23 epitope on the GFLV capsid and identifies the key residues of GFLV and Nb23 (residues 55-65 of CDR2 and 100-110 of CDR3) involved in the specific molecular recognition events occurring upon complex formation.

To test whether GFLV CP-derived VLPs are compatible with the binding of Nb23 similarly to viral particles, dynamic light scattering (DLS) and native agarose gel electrophoresis analyses were performed. DLS revealed that TRCP VLPs alone are monodisperse with a particle diameter of 32.0 nm±2 nm (mean±SD) whereas in the presence of saturating concentration of Nb23, the diameter of TRCP VLPs increased to 37.8±2 nm (FIG. 13). Native gel electrophoresis revealed that addition of Nb23 to TRCP VLP induced a significant shift in mobility of the VLP (FIG. 14 lanes 1 to 3), the inventors assume as a consequence in changes of the net electric charge density and mass of the various particles upon Nb23 binding to the VLPs. Altogether our results demonstrate that TRCP VLPs can be efficiently decorated with Nb23. They also reveal that Nb23 epitope is conserved suggesting that the TRCP VLP outer surface is structurally identical to that of GFLV particles.

To assess whether VLP can be decorated with larger molecules, TRCP VLP where incubated in the presence of purified Nb23 fused to EGFP (27 kDa) (SEQ ID NO: 31) or to bacterial alkaline phosphatase (ALP) (SEQ ID NO: 32), a homo-dimeric protein of approximately 58 kDa for each monomer (Muller et al., 2001), and tested by DLS and native agarose gel electrophoresis. Similarly to our previous results with Nb23, a significant increase of the apparent diameter of the VLPs was observed in the presence of either Nb23:GFP (43.8+/−2 nm (mean+/−SD, n=3)) or Nb23ALP (40.0+/−2 nm (mean+/−SD, n=3)) (FIG. 13).

In agreement with the efficient binding of Nb23:GFP and Nb23ALP to TRCP VLPs as suggested by our DLS results, a significant shift in mobility of the VLPs was also observed upon decoration of the VLPs by Nb23:GFP (FIG. 14 lanes 3 to 5) or Nb23ALP (FIG. 15). Under these conditions, ALP was still enzymatically active as seen by the specific FastRed-staining of decorated VLP (FIG. 15).

The inventors could demonstrate that Nb23:GFP binding to VLPs is saturable since shift in VLP mobility progressively increased upon addition of increasing amount of Nb23:GFP (FIG. 16). Maximum mobility shift was observed at approximately one to one molecular ratio between GFLV CP and Nb23:GFP suggesting that up to 60 molecules of Nb23:GFP can be bound per individual VLP. Observation of the gel by fluorescence imaging further revealed that both encaged TagRFP and exposed EGFP remained fluorescent demonstrating that Nb23-mediated binding activity does not affect the activity and integrity of the latter proteins.

Similar results were shown for several other nanobodies. VLPs can be decorated with Nbp59 and Nb122. Interestingly the ability of these nanobodies to bind CP is similar to that of Nb23 suggesting a similar stoichiometry of 1:1 for Nbp59 and Nb122 (FIGS. 17 and 18).

In order to determine potential differences in epitope recognition between the different nanobodies (Nb), competitive ELISA tests were carried out. During this test, purified GFLV viral particles were adsorbed on ELISA plates, and the presence of viral particles was revealed through Nb-PAL (p59-PAL, p75-PAL, 155-PAL) diluted at 1:500. During the detection phase of the test, conjugated buffer containing the Nb-PAL was complemented with or without the different Nb-STs diluted at 1:100 (23, 75, p59, 125, and 122) which is a large excess as compare to Nb-PAL. Binding of a given Nb-ST to the surface of the viral particle do not allow ELISA signalling as opposed to the binding of Nb-PAL. Thus, a decrease in signalling of Nb-PAL in the presence of a given Nb-ST compared to the signalling of Nb-PAL without said Nb-ST demonstrates a competition. As a control the inventors observe a very significant decrease in signalling when the p59-PAL competes with p59-ST, p75-PAL with p75-ST, and 155-PAL with 155-ST. Similar results are observed for 122-ST and 122-PAL. In agreement with their belongings to the same family, Nb23 competes with Nbp75 and no other nanobodies among Nbp59, Nb125, Nb155 and Nb122. Nb-59, Nb125 and Nb155 partially compete with each other but not with Nb23, Nb75 or Nb122. Nb122 does not compete with the other nanobodies (FIG. 19 *a*). Altogether these result suggest that epitopes recognized by Nb23/Nbp75/Nb126/Nbp71/Nb101; Nbp59/Nb37/Nb77/Nb171 and Nb122 are distinct whereas the epitopes recognized by Nb-59, Nb125 and Nb155 partially overlap.

The inventors then investigated whether VLP could be decorated with different nanobodies at the time. To address this question, DLS analysis were carried out. Results show that all particles are monodisperse with diameters of 32.0+/−2 nm for VLP, 34.0+/−2 nm for VLP saturated with Nbp59, 43.8+/−2 nm for VLP saturated with Nbp59 and Nb122:ALP and 50.7+/−2 nm for VLP saturated with Nbp59 and Nb122:ALP and Nb23:GFP. The increase in apparent diameter of the VLP confirms the successful displaying of two and even three different nanobodies on its surface (FIG. 20). These results were confirmed by native agarose gel electrophoresis where the different combinations of nanobody decorated VLPs, whether in single, double or triple combination, shows different migration patterns (FIG. 20). Interestingly the activity of proteins used as tags on these nanobodies is preserved as shown by green fluorescence for the Nb23-GFP (FIG. 20) and by the alkaline phosphatase activity of the Nb122:ALP (FIG. 21, right).

8. Identification of Non-Competing Nbs Recognizing Different Viral Epitopes

The viral epitope recognition by non-competing Nbs is crucial to realize a multiple decoration on VLP particles. Hence, the interaction of different Nbs with the viral capsid protein epitopes was inspected using competitive ELISA (FIG. 19*b*) and microscale thermophoresis (MST, FIG. 22 and Table 1).

To determine the affinity of interaction between non-competitor to Nb23 and the viral epitopes, Nb23, Nbp59 and Nb122 were selected to measure the affinity of interaction in solution using MST. A titration series of Nbp59 or Nb122 a range of 0.07 nM to 2.5 µM was performed while fluorescently labelled VLP was kept constant at 1.0 µM throughout the series. Upon binding of Nbs, a change in thermophoretic signal was observed.

Subsequent fitting of the data to a 1:1 binding model yielded a dissociation constant Kd of (12.56±3.37) nM for Nb59 and (34.51±13.63) nM for Nb122 (FIG. 22 and table 1). These values are also comparable to the ones found in literature for Nbs interactions with different binding partners (Cabanas-Danes, 2014).

TABLE 1

|  | Kd (nM) | Standard deviation |
| --- | --- | --- |
| Nb23 | 9.13 | ±2.91 |
| Nbp59 | 12.56 | ±3.37 |
| Nb122 | 34.51 | ±13.63 |

9. Epitope Mapping and Modelling of Nbp59 and Nb122 Epitopes

As shown in FIG. 19, Nbs 23, 59 and 122 do not compete for binding. As a consequence, they recognize mutually exclusive epitopes and each of them may be displayed 60 times at the surface of the capsid (FIGS. 16 and 17). ELISA performed on specific GFLV isolates (GFLV-TD, GFLV-G2 and GFLV-F13) were used to identified the epitopes recognized by Nb59 and Nb122 (FIG. 23C). While the polyclonal antibodies present in the Bioreba ELISA recognized all isolates similarly to Nb75, Nb122 failed to recognize GFLV-TD that possess a G297D mutation (Schellenberger et al 2011) and Nbp59 failed to recognize GFLV-G2 in which a stretch of 11 residues in position 188 to 198 of the CP are mutated (Schellenberger et al. 2010). This indicates that residues in position 297 and 188-198 of the GFLV CP are essential for Nb122 and Nbp59 binding, respectively. These epitope data were used in combination with molecular docking to build a model of the Nb122 and Nbp59 binding sites. Each Nb was individually docked on an isolated CP and results were filtered using four criteria: the best candidates had to select a binding site i) on the outer surface of the CP, ii) without steric clash with neighboring CPs, iii) in a zone containing critical residues (residue 297 for Nb122 and 188-198 for Nbp59), iv) and not overlapping with of other Nbs.

Nb23 was docked first as a control to test the capacity of the docking ATTRACT software to reproduce the position revealed by our EM structure and resulted in a model differing with a RMSD of only 3.4 Å compared to the resolved EM structure of Nb23-GFLV complex. Within the top 10 predictions proposed for Nb59, only one mapped to residue 198 (whose mutation affect Nb59 binding) in the region R2 (Schellenberger, 2011) and did not overlap with the Nb23 epitope (FIG. 23). The solution for Nb122 was less obvious and occurred in rank 30. It involves two neighboring CPs, with the CDR3 of Nb122 mainly engaged with the first subunit and a weaker interaction with residue 297 of the second subunit (FIG. 23). Altogether these results show that Nb23, Nbp59 and Nb122 recognize respectively epitopes that are present 60 times at the outer surface of the viral capsid and that these three nanobodies recognize sufficiently distinct epitopes to allow their binding on one capsid protein, meaning that they can be displayed up to 180 times at the outer surface of the viral capsid, each of these three Nbs being present 60 times.

10. Heat Stabilization of the GFLV Capsid by Nb23.

The inventors were interested in finding out whether the Nb23 exerts a stabilizing activity against heat on the GFLV capsid. When a GFLV particle is heated, the capsid is destabilized and viral RNA becomes accessible. The thermostability of the capsid alone or complexed to Nb23 was assessed using a ThermoFluor assay, in which the compounds are gradually heated in the presence of SYBR green II to detect the release of viral RNA. The fluorescent signals are continuously measured and result in a sigmoidal curve when plotted as a function of the temperature. From these curves, the temperature at which 50% of the RNA was released from the capsid (50% effective temperature [ET50]) could be calculated. These ET50 values are given in Table 2 and show that Nb23 was able to increase the stability of the GFLV capsid by approximately 10° C., which represents a nearly 20% increase in thermal stability of the particle. This is significantly better than the stability exerted by neutralizing Nanobodies recognizing poliovirus type 1 (Schotte, L., et al. (2014) J Virol 88, 4403-4413).

TABLE 2

|  | Temperature mean (° C.) | Standard deviation |
|---|---|---|
| GFLV | 49.833 | ±0.453 |
| GFLV + Nb23 | 59.745 | ±0.064 |

Altogether our results demonstrate that nanobodies allow efficient and rapid display of foreign proteins at the surface of GFLV CP-derived VLPs. They also show that native molecules as large as Nb23:GFP (≅42 Kda) and Nb23:ALP (≅73 kDa) in its monomeric form) can be bound to VLP without loss of activity. In addition, a combination of three nanobodies allows the display of up to 180 nanobodies at the surface of the VLPs.

```
Sequences

SEQ ID NO: 1: GFLV Coat Protein amino acid sequence
MGLAGRGVIYIPKDCQANRYLGTLNIRDMISDFKGVQYEKWITAGLVMPTFKIVIRLPANAFTGLTWVMSFDAYNRITSRI
TASADPVYTLSVPHWLIHHKLGTFSCEIDYGELCGHAMWFKSTTFESPRLHFTCLTGNNKELAADWQAVVELYAELEEATS
FLGKPTLVFDPGVFNGKFQFLTCPPIFFDLTAVTALRSAGLTLGQVPMVGTTKVYNLNSTLVSCVLGMGGTVRGRVHICAP
IFYSIVLWVVSEWNGTTMDWNELFKYPGVYVEEDGSFEVKIRSPYHRTPARLLAGQSQRDMSSLNFYAIAGPIAPSGETAQ
LPIVVQIDEIVRPDLSLPSFEDDYFVWVDFSEFTLDKEEIEIGSRFFDFTSNTCRVSMGENPFAAMIACHGLHSGVLDLKL
QWSLNTEFGKSSGSVTITKLVGDKAMGLDGPSHVFAIQKLEGTTELLVGNFAGANPNTRFSLYSRWMAIKLDQAKSIKVLR
VLCKPRPGFSFYGRTSFPV SEQ ID NO: 2: CPTR
MGLAGRGVIYIPKDCQANRYLGTLNIRDMISDFKGVQYEKWITAGLVMPTFKIVIRLPANAFTGLTWVMSFDAYNRITSRI
TASADPVYTLSVPHWLIHHKLGTFSCEIDYGELCGHAMWFKSTTFESPRLHFTCLTGNNKELAADWQAVVELYAELEEATS
FLGKPTLVFDPGVFNGKFQFLTCPPIFFDLTAVTALRSAGLTLGQVPMVGTTKVYNLNSTLVSCVLGMGGTVRGRVHICAP
IFYSIVLWVVSEWNGTTMDWNELFKYPGVYVEEDGSFEVKIRSPYHRTPARLLAGQSQRDMSSLNFYAIAGPIAPSGETAQ
LPIVVQIDEIVRPDLSLPSFEDDYFVWVDFSEFTLDKEEIEIGSRFFDFTSNTCRVSMGENPFAAMIACHGLHSGVLDLKL
QWSLNTEFGKSSGSVTITKLVGDKAMGLDGPSHVFAIQKLEGTTELLVGNFAGANPNTRFSLYSRWMAIKLDQAKSIKVLR
VLCKPRPGFSFYGRTSFPVGGGSGGGMSELIKENMHMKLYMEGTVNNHHFKCTSEGEGKPYEGTQTMRIKVVEGGPLPFAF
DILATSFMYGSRTFINHTQGIPDFFKQSFPEGFTWERVTTYEDGGVLTATQDTSLQDGCLIYNVKIRGVNFPSNGPVMQKK
TLGWEANTEMLYPADGGLEGRSDMALKLVGGGHLICNFKTTYRSKKPAKNLKMPGVYYVDHRLERIKEADKETYVEQHEVA
VARYCDLPSKLGHKLN
Bold: linker
underlined: coat protein SEQ ID NO: 3: TRCP
MSELIKENMHMKLYMEGTVNNHHFKCTSEGEGKPYEGTQTMRIKVVEGGPLPFAFDILATSFMYGSRTFINHTQGIPDFFK
QSFPEGFTWERVTTYEDGGVLTATQDTSLQDGCLIYNVKIRGVNFPSNGPVMQKKTLGWEANTEMLYPADGGLEGRSDMAL
KLVGGGHLICNFKTTYRSKKPAKNLKMPGVYYVDHRLERIKEADKETYVEQHEVAVARYCDLPSKLGHKLNGGGSGGGGLA
GRGVIYIPKDCQANRYLGTLNIRDMISDFKGVQYEKWITAGLVMPTFKIVIRLPANAFTGLTWVMSFDAYNRITSRITASA
DPVYTLSVPHWLIHHKLGTFSCEIDYGELCGHAMWFKSTTFESPRLHFTCLTGNNKELAADWQAVVELYAELEEATSFLGK
PTLVFDPGVFNGKFQFLTCPPIFFDLTAVTALRSAGLTLGQVPMVGTTKVYNLNSTLVSCVLGMGGTVRGRVHICAPIFYS
IVLWVVSEWNGTTMDWNELFKYPGVYVEEDGSFEVKIRSPYHRTPARLLAGQSQRDMSSLNFYAIAGPIAPSGETAQLPIV
VQIDEIVRPDLSLPSFEDDYFVWVDFSEFTLDKEEIEIGSRFFDFTSNTCRVSMGENPFAAMIACHGLHSGVLDLKLQWSL
NTEFGKSSGSVTITKLVGDKAMGLDGPSHVFAIQKLEGTTELLVGNFAGANPNTRFSLYSRWMAIKLDQAKSIKVLRVLCK
PRPGFSFYGRTSFPV
Bold: linker
underlined: coat protein SEQ ID NO: 4: CPEG
MGLAGRGVIYIPKDCQANRYLGTLNIRDMISDFKGVQYEKWITAGLVMPTFKIVIRLPANAFTGLTWVMSFDAYNRITSRI
TASADPVYTLSVPHWLIHHKLGTFSCEIDYGELCGHAMWFKSTTFESPRLHFTCLTGNNKELAADWQAVVELYAELEEATS
FLGKPTLVFDPGVFNGKFQFLTCPPIFFDLTAVTALRSAGLTLGQVPMVGTTKVYNLNSTLVSCVLGMGGTVRGRVHICAP
IFYSIVLWVVSEWNGTTMDWNELFKYPGVYVEEDGSFEVKIRSPYHRTPARLLAGQSQRDMSSLNFYAIAGPIAPSGETAQ
LPIVVQIDEIVRPDLSLPSFEDDYFVWVDFSEFTLDKEEIEIGSRFFDFTSNTCRVSMGENPFAAMIACHGLHSGVLDLKL
QWSLNTEFGKSSGSVTITKLVGDKAMGLDGPSHVFAIQKLEGTTELLVGNFAGANPNTRFSLYSRWMAIKLDQAKSIKVLR
VLCKPRPGFSFYGRTSFPVDPAFLYKVVRSFGPAMVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYKTRAEVKFEGDTLVNRIELKG
IDFKEDGNILGHKLEYNYNSHNVYIMADKQKNGIKVNFKIRHNIEDGSVQLADHYQQNTPIGDGPVLLPDNHYLSTQSALS
KDPNEKRDHMVLLEFVTAAGITLGMDELYKTS
Bold: linker
underlined: coat protein SEQ ID NO: 5: TR
MSELIKENMHMKLYMEGTVNNHHFKCTSEGEGKPYEGTQTMRIKVVEGGPLPFAFDILATSFMYGSRTFINHTQGIPDFFK
QSFPEGFTWERVTTYEDGGVLTATQDTSLQDGCLIYNVKIRGVNFPSNGPVMQKKTLGWEANTEMLYPADGGLEGRSDMAL
KLVGGGHLICNFKTTYRSKKPAKNLKMPGVYYVDHRLERIKEADKETYVEQHEVAVARYCDLPSKLGHN
```

| Sequences |
|---|

SEQ ID NO: 6: LINKER
DPAFLYKVVRSFGPA

SEQ ID NO: 7: Nb126
QVQLQESGGG SVQVGGSLRL ACAASGDTFS GYLAAWFRQA PGKEREGVAA INSVRHTTSY        60
ANSVKGRFTI SKDNADNMMY LEMNSLKPED TAIYYCAAAD AIGLAEYWST PTLSAARYKY       120
WGQGTQVTVS S

SEQ ID NO: 8: Nb101
QVQLQESGGG SVQVGGSLRL ACAASGDTFS GYLAAWFRQA PGKEREGVAA INSVRHTTSY        60
ADSVKGRFTI SKDNADNMMY LEMNGLKPED TAIYYCAAAD AIGLAEYWST PTLSAARYKY       120
WGQGTQVTVS S                                                           131

SEQ ID NO: 9: Nb23
QVQLQESGGG SVQVGGSLRV ACAASGDTFS GYLAAWFRQA PGKGREGVAA INSKRHTTSY        60
ADSVKGRFTI SKDNADNIMY LEMNSLKPED TAIYYCAAAD AIGLAEYWST PTLSAARYKY       120
WGQGTQVTVS S                                                           131

SEQ ID NO: 10: Nbp75
QVQLQESGGG SVQAGGSLRL SCVASEYPSS STAMAWFRQA PGKEREGVAA INSVRHTTSY        60
ADSVKGRFTI SKDNADNMMY LEMNSLKPED TAIYYCAAAD AIGLAEYWST PTLSAARYKY       120
WGQGTQVTVS S                                                           131

SEQ ID NO: 11: Nbp71
QVQLQESGGG AVQPGGSLKL SCEASGDVPE NGYMAWFRQA PGKEREGVAA INSVRHTTSY        60
ADSVKGRFTI SKDNADNMMY LEMNSLKPED TAIYYCAAAD AIGLAEYWST PTLSAARYKY       120
WGQGTQVTVS S                                                           131

SEQ ID NO: 12: Nbp59
QVQLQESGGG TVQAGGSLRL SCSISGDTSN SYCMGWFRQA PGKEREVVAH ISTGVISPGY        60
NKFSEGRFTI SPDNAKNSVY LQMNNLKPDD TAMYYCAART GYCSGSWGVA DSFNGWGQGT       120
QVTVSS                                                                 126

SEQ ID NO: 13: Nb125
QVQLQESGGG SVQAGGSLRL SCAASGYTYS MYCMAWFRQA PGKEREGVAA INSGNRSTYY        60
ADSVKGRFTI SQDNAKNTVY LIMNSLKPED TAIYYCAADP QRCGSWTWAN MYEYNYWGQG       120
TQVTVSS                                                                127

SEQ ID NO: 14: Nb155
QVQLQESGGG SVQAGESLRL SCTASELTFS DYIMNWFRQA QGKECERVSM IIQNGGDTHY        60
ADSVKGRFTI SRDNTKSTLH LQMNNLRPDD TAVYYCAAGA LLPTFNHCPP PGAYFGQGTQ       120
VTVSS                                                                  125

SEQ ID NO: 15: Nb37
QVQLQESGGG TVQAGGSLRL SCSISGDTSN SYCMGWFRQA PGKEREVVAH ISTNNISPAY        60
NKFREGRFTI SPDNAKNSVY LQMNNLKPED TAMYYCAART GYCSGSWGVA DSFNGWGQGT       120
QVTVSS                                                                 126

SEQ ID NO: 16: Nb77
QVQLQESGGG TVQAGGSLRL SCSISGDTSN SYCMGWFRQA PGKEREVVAH ISTGVISPGY        60
NKFAEGRFTI SPDNAKNSVY LQMNNLKPED TAMYFCAART GSCSGSWGVA DSFNGWGQGT       120
QVTVSS                                                                 126

SEQ ID NO: 17: Nb171
QVQLQESGGG TVQAGGSLRL SCSISGDTSN SYCMGWFRQA PGKEREVVAR ISTGVISPGY        60
NKFAEGRFTI SPDNAKNSVY LQMNNLKPED TAMYFCAART GSCSGSWGVA DSFNGWGQGT       120
QVTVSS                                                                 126

SEQ ID NO: 18: Nb159
QVQLQESGGG SVQAGGSLRL SCAASGYTYS MYCMAWFRQA PGKEREGVAA INSGGPSTYY        60
ADSVKGRFTI SQDNAKNTVY LIMNSLKPED TAIYYCAADP QRCGSWSWAN MYEYNYWGQG       120
TQVTVSS                                                                127

SEQ ID NO: 19: Nbp25
QVQLQESGGG SVQAGGSLRL SCAASGYTYS MYCMGWFRQA PGKEREGVAA INSGNGNTYY        60
ADSVKGRFTI SQDNAKNTMY LLMNSLKPED TAIYYCAADP QRCGSWTWAG VFEYNYWGQG       120
TQVTVSS                                                                127

SEQ ID NO: 20: Nb172
QVQLQESGGG SVQAGESLRL SCTASGITFS DYFMNWFRQA QGKECERVSM ISMNGADTHY        60
ADSVKGRFTI SRDNTKSTLH LQMNNLRPDD TAVYYCAAGA LLPSYNHCPP PGAYFGQGTQ       120
VTVSS                                                                  125

Sequences

SEQ ID NO: 21: Nb122
QVQLQESGGG SVQGGGSLRL SCAVSGYRFS SYAMAWFRQA PGKEREAVAA YYRGFGGAQH       60
STHYAASVTG RFTITQNDAL NTGYLQMNNL KPEDTAMYYC ALSTADDDDW HSLRRYNYWG      120
QGTQVTVSS                                                             129

SEQ ID NO: 22: Nb15
QVQLQESGGG SVQAGGSLRL SCATSGYTLR PYCMGWFRQA PGKEREGVAT ITRSGDRTYY      60
ADAVKGRFTI SQDTAKNTVY LQMNNLKSED AANYYCAASF NYLPTYLTCG SRTAEYNFWG      120
QGTQVTVSS                                                             129

SEQ ID NO: 23: Nbp77
QVQLQESGGG SVQAGGSLRL SCTTSGYTLR PYCMGWFRQA PGKEREGVAT ITRSGDRTSY      60
ADAVKGRFTI SQDTAKNTVY LQMNNLKSED AANYYCAASF NYRPTYVTCN SRTAEYNFWG      120
QGTQVTVSS                                                             129

SEQ ID NO: 24: Nb34
QVQLQESGGG SVQAGGSLRL SCAASGYTYS SYCMGWFRQA PGKEREGVAT IDSGSGRTYY      60
ADSVKGRFTI SRDNAKDTVY LLMNNLKPED TAIYYCAAVG ANSGGLWSSC GYCYGGLCGD      120
DFGYWGQGTQ VTVSS                                                      135

SEQ ID NO: 25: Nb80
QVQLQESGGG SVQAGGSLRL SCAASGYTYS SYCMGWFRQA PGKEREGVAT IDSGSGRTYY      60
ADSVKGRFTI SQDNAKNTVY LLMNNLKPED TAIYYCAAVG ANSGGLWSSC GYCYGGLCED      120
DFGYWGQGTQ VTVSS                                                      135

SEQ ID NO: 26: Nb38
QVQLQESGGG SVQAGGSLRL SCAASGYTHS INLMGWFRQA PGKEREGVAT IYTVGSSSTY      60
YADSVKGRFT ISLDNAKNTV YLRMNSLKPE DTAMYYCAAG VGWLSNSEYN YWGQGTQVTV      120
SS                                                                    122

SEQ ID NO: 27: Nb137
QVQLQESGGG SVQAGGSLKL SCRVYGYIAS QCGMGWYRQA PGKGRELVTT ISSDGSTTYA      60
DSIKGRFTIS RDNVENTLYL QMNNLKPEDT AVYYCAADPL GNSCPGLSYS AQGTQVTVSS      120

SEQ ID NO: 28: Nb139
QVQLQESGGG SVQAGGSLRL SCAASEYIYS RNCMGWFRQA PGKEREGVAA IYTGSGNTNY      60
ADSVKGRFTI AQDNAKNAVY LQMNSLKPED TAVYYCAARN SGSWWRPSCN FDSDFGYWGQ      120
GTQVTVSS                                                              128

SEQ ID NO: 29: Nbp12
QVQLQESGGG SVQAGGSLRL SCKASTYTTN SFCMGWFRQA PGKEREGVAV IQPGRNSKDY      60
ADSVKGRFTI SQDNALNTVY LQMNSLKPED TAMYYCASTG LWISSGSCQT IPDQYSYWGQ      120
GTQVTVSS                                                              128

SEQ ID NO: 30: TRCPEG
MSELIKENMHMKLYMEGTVNNHHFKCTSEGEGKPYEGTQTMRIKVVEGGPLPFAFDILATSFMYGSRTFINHTQGIPDFFK
QSFPEGFTWERVTTYEDGGVLTATQDTSLQDGCLIYNVKIRGVNFPSNGPVMQKKTLGWEANTEMLYPADGGLEGRSDMAL
KLVGGGHLICNFKTTYRSKKPAKNLKMPGVYYVDHRLERIKEADKETYVEQHEVAVARYCDLPSKLGHKLNGGGSGGG**GLA
GRGVIYIPKDCQANRYLGTLNIRDMISDFKGVQYEKWITAGLVMPTFKIVIRLPANAFTGLTWVMSPDAYNRITSRITASA
DPVYTLSVPHWLIHHKLGTFSCEIDYGELCGHAMWFKSTTFESPRLHFTCLTGNNKELAADWQAVVELYAELEEATSFLGK
PTLVFDPGVFNGKFQFLTCPPIFFDLTAVTALRSAGLTLGQVPMVGTTKVYNLNSTLVSCVLGMGGTVRGRVHICAPIFYS
IVLWVVSEWNGTTMDWNELFKYPGVYVEEDGSFEVKIRSPYHRTPARLLAGQSQRDMSSLNFYAIAGPIAPSGETAQLPIV
VQIDEIVRPDLSLPSFEDDYFVWVDFSEFTLDKEEIEIGSRFFDFTSNTCRVSMGENPFAAMIACHGLHSGVLDLKLQWSL
NTEFGKSSGSVTITKLVGDKAMGLDGPSHVFAIQKLEGTTELLVGNFAGANPNTRFSLYSRWMAIKLDQAKSIKVLRVLCK
PRPGFSFYGRTSFPVDPAFLYKVVRSFGPAMVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFKDDGNYKTRAEVKFEGDTLVNRIELKGIDFK
EDGNILGHKLEYNYNSHNVYIMADKQKNGIKVNFKIRHNIEDGSVQLADHYQQNTPIGDGPVLLPDNHYLSTQSALSKDPN
EKRDHMVLLEFVTAAGITLGMDELYKTS**
The protein weighs 111.52 kilodaltons. In bold the CP of GFLV.

SEQ ID NO: 31: Nb23EGFP
<u>QVQLQESGGGSVQVGGSLRVACAASGDTFSGYLAAWFRQAPGKGREGVAAINSKRHTTSYADSVKGRFTISKDNADNIMYL
EMNSLKPEDTAIYYCAAADAIGLAEYWSTPTLSAARYKYWGQGTQVTVSS</u>GGGSGGG**MVSKGEELFTGVVPILVELDGDVN
GHKFSVSGEGEGDATYGKLTLKFICTTGKLPVPWPTLVTTLTYGVQCFSRYPDHMKQHDFFKSAMPEGYVQERTIFFKDDG
NYKTRAEVKFEGDTLVNRIELKGIDFKEDGNILGHKLEYNYNSHNVYIMADKQKNGIKVNFKIRHNIEDGSVQLADHYQQN
TPIGDGPVLLPDNHYLSTQSALSKDPNEKRDHMVLLEFVTAAGITLGMDELYKTS**HHHHHH
In bold the sequence of EGFP. Underlined: Nb23

SEQ ID NO: 32: Nb23ALP
<u>QVQLQESGGGSVQVGGSLRVACAASGDTFSGYLAAWFRQAPGKGREGVAAINSKRHTTSYADSVKGRFTISKDNADNIMYL
EMNSLKPEDTAIYYCAAADAIGLAEYWSTPTLSAARYKYWGQGTQVTVSS</u>GGGSGGG**VKQSTIALALLPLLFTPVTKARTP
EMPLQTQATSREEPPRLPSKHRPGVKTQATSREEPPRLPSKHRPGVKTQATSREEPPRLPSKHRPGVKTQATSREEPPRLP
SKHRPGVKTQATSLEVLENRAAQGDITAPGGARRLTGDQTAALRDSLSDKPAKNIILLIGDGMGDSEITAARNYAEGAGGF**

Sequences

FKGIDALPLTGQYTHYALNKKTGKPDYVTDSAASATAWSTGVKTYNGALGVDIHEKDHPTILEMAKAAGLATGNVSTAELQ
DATPAALVAHVTSRKCYGPSATSEKCPGNALEKGGKGSITEQLLNARADVTLGGGAKTFAETATAGEWQGKTLREQAQARG
YQLVSDAASLNSVTEANQQKPLLGLFADGNMPVRWLGPKATYHGNIDKPAVTCTPNPQRNDSVPTLAQMTDKAIELLSKNE
KGFFLQVEGASIDKQDHAANPCGQIGETVDLDEAVQRALEFAKKEGNTLVIVTADHAHASQIVAPDTKAPGLTQALNTKDG
AVMVMSYGNSEEDSQEHTGSQLRIAAYGPHAAHHHHHH
In bold the sequence of ALP. Underlined: Nb23

SEQ ID NO: 33: Nb122: ALP
MAQVQLQESGGGSVQGGGSLRLSCAVSGYRFSSYAMAWFRQAPGKEREAVAAYYRGFGGAQHSTHYAASVTGRFTITQNDA
LNTGYLQMNNLKPEDTAMYYCALSTADDDDWHSLRRYNYWGQGTQVTVSSGGGSGGGVKQSTIALALLPLLFTPVTKARTP
EMPLQTQATSREEPPRLPSKHRPGVKTQATSREEPPRLPSKHRPGVKTQATSREEPPRLPSKHRPGVKTQATSREEPPRLP
SKHRPGVKTQATSLEVLENRAAQGDITAPGGARRLTGDQTAALRDSLSDKPAKNIILLIGDGMGDSEITAARNYAEGAGGF
FKGIDALPLTGQYTHYALNKKTGKPDYVTDSAASATAWSTGVKTYNGALGVDTHEKDHPTILEMAKAAGLATGNVSTAELQ
DATPAALVAHVTSRKCYGPSATSEKCPGNALEKGGKGSITEQLLNARADVTLGGGAKTFAETATAGEWQGKTLREQAQARG
YQLVSDAASLNSVTEANQQKPLLGLFADGNMPVRWLGPKATYHGNIDKPAVTCTPNPQRNDSVPTLAQMTDKAIELLSKNE
KGFFLQVEGASIDKQDHAANPCGQIGETVDLDEAVQRALEFAKKEGNTLVIVTADHAHASQIVAPDTKAPGLTQALNTKDG
AVMVMSYGNSEEDSQEHTGSQLRIApAYGPHAAHHHHHH
In bold the sequence of ALP. Underlined: Nb122

REFERENCES

Busso, D., Delagoutte-Busso, B. and Moras, D. (2005) Construction of a set Gateway-based destination vectors for high-throughput cloning and expression screening in *Escherichia coli*. *Analytical biochemistry* 343, 313-321.

Carrillo-Tripp, M., Shepherd, C. M., Borelli, I. a., Venkataraman, S., Lander, G., Natarajan, P., Johnson, J. E., Brooks, C. I. and Reddy, V. S. (2009) VIPERdb2: An enhanced and web API enabled relational database for structural virology. *Nucleic Acids Res.*, 37, 436-442.

Conrath, K. E., Lauwereys, M., Galleni, M., Matagne, A., Frbre, J.-M., Kinne, J., Wyns, L and Muyldermans, S. (2001) O-Lactamase inhibitors derived from single-domain antibody fragments elicited in the camelidae. *Antimicrobial agents and chemotherapy* 45, 2807-2812.

Habib, I., Smolarek, D., Hattab, C., Grodecka, M., Hassanzadeh-Ghassabeh, G., Muyldermans, S., Sagan, S., Gutidrrez, C., Laperche, S. and Le-Van-Kim, C. (2013) V H H (nanobody) directed against human glycophorin A: A tool for autologous red cell agglutination assays. *Analytical biochemistry* 438, 82-89.

Ho, S. N., Hunt, H. D., Horton, R. M., Pullen, J. K. and Pease, L R. (1989) Site-directed mutagenesis by overlap extension using the polymerase chain reaction. Gene, 77, 51-59.

Merzlyak, E. M., Goedhart, J., Shcherbo, D., et al. (2007) Bright monomeric red fluorescent protein with an extended fluorescence lifetime. *Nat. Methods*, 4, 555-557.

Muller, B. H., Lamoure, C., Le Du, M. H., Cattolico, L, Lajeunesse, E., Lemaltre, F., Pearson, A., Ducancel, F., Mdnez, A. and Boulain, J. C. (2001) Improving *Escherichia coli* alkaline phosphatase efficacy by additional mutations inside and outside the catalytic pocket. *Chembiochem* 2, 517-523.

Pettersen, E. F., Goddard, T. D., Huang, C. C., Couch, G. S., Greenblatt, D. M., Meng, E. C. and Ferrin, T. E. (2004) UCSF Chimera—A visualization system for exploratory research and analysis. *J. Comput. Chem.*, 25, 1605-1612.

Quacquarelli, a., Gallitelli, D., Savino, V. and Martelli, G. P. (1976) Properties of grapevine fanleaf virus. *J. Gen. Virol.*, 32, 349-360.

Reddy Chichili, V. P., Kumar, V. and Sivaraman, J. (2013) Linkers in the structural biology of protein-protein interactions. *Protein Sci.*, 22, 153-167.

Sainsbury, F., Thuenemann, E. C. and Lomonossoff, G. P. (2009) pEAQ: versatile expression vectors for easy and quick transient expression of heterologous proteins in plants. *Plant Biotechnol. J.*, 7, 682-93. Available at: Worldwide Website: ncbi.nlm.nih.gov/pubmed/19627561 [Accessed Mar. 15, 2012].

Schellenberger, P., Andret-Unk, P., Schmitt-Keichinger, C., et al. (2010) A stretch of 11 amino acids in the betaB-betaC loop of the coat protein of grapevine fanleaf virus is essential for transmission by the nematode *Xiphinema index*. *J. Virol.*

Schellenberger, P., Demangeat, G., Lemaire, O., Ritzenthaler, C., Bergdoll, M., Olieric, V., Sauter, C. and Lorber, B. (2011) Strategies for the crystallization of viruses: Using phase diagrams and gels to produce 3D crystals of Grapevine fanleaf virus. *J. Struct. Biol.*, 174, 344-351.

Schneider, C. a, Rasband, W. S. and Eliceiri, K. W. (2012) NIH Image to ImageJ: 25 years of image analysis. *Nat. Methods*, 9, 671-675. Available at: dx.doi.org/10.1038/nmeth.2089.

Schneider, C. a, Rasband, W. S. and Eliceiri, K. W. (2012) NIH Image to ImageJ: 25 years of image analysis. *Nat. Methods*, 9, 671-675. Available at: http://dx.doi.org/10.1038/nmeth.2089.

Studier, F. W. (2005) Protein production by auto-induction in high-density shaking cultures. *Protein expression and purification* 41, 207-234.

Thys, B., Schotte, L, Muyldermans, S., Wernery, U., Hassanzadeh-Ghassabeh, G. and Rombaut, B. (2010) In vitro antiviral activity of single domain antibody fragments against poliovirus. *Antiviral Research* 87, 257-264.

Vigne, E., Gottula, J., Schmitt-Keichinger, C., et al. (2013) A strain-specific segment of the RNA-dependent RNA polymerase of grapevine fanleaf virus determines symptoms in *Nicotiana* species. *J. Gen. Virol.*, 94, 2803-2813.

Viry, M., Serghini, M. A., Hans, F., et al. (1993) Biologically active transcripts from cloned eDNA of genomic grapevine fanleaf nepovirus RNAs. *In Vitro*, 4207, 169-174.

Zilian, E. and Maiss, E. (2011) An optimized mRFP-based bimolecular fluorescence complementation system for the detection of protein-protein interactions in planta. *J. Virol. Methods*, 174, 158-165. Available at: dx.doi.org/10.1016/j.jviromet.2011.03.032.

The invention claimed is:

1. A virus-like particle (VLP) comprising both a Grapevine fanleaf virus (GFLV) coat protein and at least two or three different anti-GFLV coat protein antibodies or antibody derivatives, wherein the different anti-GFLV coat protein antibodies or antibody derivatives do not compete with each other for binding to the GFLV coat protein of said VLP.

2. The particle of claim 1, wherein the antibody derivative is a nanobody or a ScFv.

3. The particle of claim 1, wherein at least one of the anti-GFLV coat protein antibodies or antibody derivatives comprises the sequences of a set of CDR 1, CDR 2 and CDR 3 from one of the following groups:

| Group | CDR1 SEQ ID NO: | CDR2 SEQ ID NO: | CDR3 SEQ ID NO: | Nanobody |
|---|---|---|---|---|
| I | 34 | 35 | 36 | 23 |
|  | 37 | 38 | 39 | p75 |
|  | 40 | 41 | 42 | 101 |
|  | 43 | 44 | 45 | 126 |
|  | 46 | 47 | 48 | p71 |
| II | 49 | 50 | 51 | p59 |
|  | 52 | 53 | 54 | 125 |
|  | 55 | 56 | 57 | 155 |
|  | 58 | 59 | 60 | 37 |
|  | 61 | 62 | 63 | 77 |
|  | 64 | 65 | 66 | 171 |
|  | 67 | 68 | 69 | 159 |
|  | 70 | 71 | 72 | p25 |
|  | 73 | 74 | 75 | 172 |
| III | 76 | 77 | 78 | 122 |
| IV | 79 | 80 | 81 | 15 |
|  | 82 | 83 | 84 | p77 |
| V | 85 | 86 | 87 | 34 |
|  | 88 | 89 | 90 | 80 |
| VI | 91 | 92 | 93 | 38 |
| VII | 94 | 95 | 96 | 137 |
| VIII | 97 | 98 | 99 | 139 |
| IX | 100 | 101 | 102 | p12. |

4. The particle of claim 1, wherein at least one of the anti-GFLV coat protein antibodies or antibody derivatives comprises a sequence from one of the following groups:

| Group | SEQ ID NO: | Nanobody (Nb) |
|---|---|---|
| I | 9 | 23 |
|  | 10 | p75 |
|  | 8 | 101 |
|  | 7 | 126 |
|  | 11 | p71 |
| II | 12 | p59 |
|  | 13 | 125 |
|  | 14 | 155 |
|  | 15 | 37 |
|  | 16 | 77 |
|  | 17 | 171 |
|  | 18 | 159 |
|  | 19 | p25 |
|  | 20 | 172 |
| III | 21 | 122 |
| IV | 22 | 15 |
|  | 23 | p77 |
| V | 24 | 34 |
|  | 25 | 80 |
| VI | 26 | 38 |
| VII | 27 | 137 |
| VIII | 28 | 139 |
| IX | 29 | p12. |

5. The particle of claim 3, wherein the different anti-GFLV coat protein antibodies or antibody derivatives are selected from groups I to IX.

6. The particle of claim 5, wherein:
a first anti-GFLV coat protein antibody or antibody derivative is selected from Group I, a second anti-GFLV coat protein antibody or antibody derivative is selected from Group II and optionally a third anti-GFLV coat protein antibody or antibody derivative is selected from Group III; or
a first anti-GFLV coat protein antibody or antibody derivative is selected from Group I, a second anti-GFLV coat protein antibody or antibody derivative is selected from Group III and optionally a third anti-GFLV coat protein antibody or antibody derivative is selected from Group II; or
a first anti-GFLV coat protein antibody or antibody derivative is selected from Group II, a second anti-GFLV coat protein antibody or antibody derivative is selected from Group III and optionally a third anti-GFLV coat protein antibody or antibody derivative is selected from Group I.

7. The particle of claim 5, wherein:
a first anti-GFLV coat protein antibody or antibody derivative is selected from the group consisting of Nb23 and Nbp75, a second anti-GFLV coat protein antibody or antibody derivative is selected from the group consisting of Nbp59, Nb125 and Nb155, and optionally a third anti-GFLV coat protein antibody or antibody derivative is Nb122; or
a first anti-GFLV coat protein antibody or antibody derivative is selected from the group consisting of Nb23 and Nbp75, a second anti-GFLV coat protein antibody or antibody derivative is Nb122 and optionally a third anti-GFLV coat protein antibody or antibody derivative is selected from the group consisting of Nbp59, Nb125 and Nb155; or
a first anti-GFLV coat protein antibody or antibody derivative is selected from the group consisting of Nbp59, Nb125 and Nb155, a second anti-GFLV coat protein antibody or antibody derivative is Nb122, and optionally a third anti-GFLV coat protein antibody or antibody derivative is selected from the group consisting of Nb23 and Nbp75.

8. The particle of claim 1, wherein:
a) the different anti-GFLV coat protein antibodies or antibody derivatives are conjugated to a compound; or
b) the different anti-GFLV coat protein antibodies or antibody derivatives are conjugated to a different compound for each anti-GFLV coat protein antibody or antibody derivative.

9. The particle of claim 8, wherein the GFLV coat protein of said VLP is conjugated to a compound by covalent coupling at the N-terminus of the GFLV coat protein.

10. The particle of claim 1, wherein the GFLV coat protein of said VLP comprises SEQ ID NO: 1, or a sequence having at least 80% identity to SEQ ID NO: 1.

11. The particle of claim 8, wherein the compound is a therapeutic, diagnostic or imaging agent or a tag.

12. A pharmaceutical composition comprising one or more virus-like particles of claim 1.

* * * * *

SEQUENCE LISTING

<160> NUMBER OF SEQ ID NOS: 106

<210> SEQ ID NO 1
<211> LENGTH: 505
<212> TYPE: PRT
<213> ORGANISM: Artificial
<220> FEATURE:
<223> OTHER INFORMATION: GFLV Coat Protein

<400> SEQUENCE: 1

Met Gly Leu Ala Gly Arg Gly Val Ile Tyr Ile Pro Lys Asp Cys Gln
1               5                   10                  15

Ala Asn Arg Tyr Leu Gly Thr Leu Asn Ile Arg Asp Met Ile Ser Asp
            20                  25                  30

Phe Lys Gly Val Gln Tyr Glu Lys Trp Ile Thr Ala Gly Leu Val Met
        35                  40                  45

Pro Thr Phe Lys Ile Val Ile Arg Leu Pro Ala Asn Ala Phe Thr Gly
50                  55                  60

Leu Thr Trp Val Met Ser Phe Asp Ala Tyr Asn Arg Ile Thr Ser Arg
65                  70                  75                  80

Ile Thr Ala Ser Ala Asp Pro Val Tyr Thr Leu Ser Val Pro His Trp
                85                  90                  95

Leu Ile His His Lys Leu Gly Thr Phe Ser Cys Glu Ile Asp Tyr Gly
            100                 105                 110

Glu Leu Cys Gly His Ala Met Trp Phe Lys Ser Thr Thr Phe Glu Ser
        115                 120                 125

Pro Arg Leu His Phe Thr Cys Leu Thr Gly Asn Asn Lys Glu Leu Ala
130                 135                 140

Ala Asp Trp Gln Ala Val Val Glu Leu Tyr Ala Glu Leu Glu Glu Ala
145                 150                 155                 160

Thr Ser Phe Leu Gly Lys Pro Thr Leu Val Phe Asp Pro Gly Val Phe
                165                 170                 175

Asn Gly Lys Phe Gln Phe Leu Thr Cys Pro Pro Ile Phe Phe Asp Leu
            180                 185                 190

Thr Ala Val Thr Ala Leu Arg Ser Ala Gly Leu Thr Leu Gly Gln Val
        195                 200                 205

Pro Met Val Gly Thr Thr Lys Val Tyr Asn Leu Asn Ser Thr Leu Val
210                 215                 220

Ser Cys Val Leu Gly Met Gly Gly Thr Val Arg Gly Arg Val His Ile
225                 230                 235                 240

Cys Ala Pro Ile Phe Tyr Ser Ile Val Leu Trp Val Val Ser Glu Trp
                245                 250                 255

Asn Gly Thr Thr Met Asp Trp Asn Glu Leu Phe Lys Tyr Pro Gly Val
            260                 265                 270

Tyr Val Glu Glu Asp Gly Ser Phe Glu Val Lys Ile Arg Ser Pro Tyr
        275                 280                 285

His Arg Thr Pro Ala Arg Leu Leu Ala Gly Gln Ser Gln Arg Asp Met
290                 295                 300

Ser Ser Leu Asn Phe Tyr Ala Ile Ala Gly Pro Ile Ala Pro Ser Gly
305                 310                 315                 320

Glu Thr Ala Gln Leu Pro Ile Val Val Gln Ile Asp Glu Ile Val Arg
                325                 330                 335

Pro Asp Leu Ser Leu Pro Ser Phe Glu Asp Asp Tyr Phe Val Trp Val
            340                 345                 350

```
Asp Phe Ser Glu Phe Thr Leu Asp Lys Glu Ile Glu Ile Gly Ser
            355                 360                 365

Arg Phe Phe Asp Phe Thr Ser Asn Thr Cys Arg Val Ser Met Gly Glu
370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
            405                 410                 415

Ser Gly Ser Val Thr Ile Thr Lys Leu Val Gly Asp Lys Ala Met Gly
            420                 425                 430

Leu Asp Gly Pro Ser His Val Phe Ala Ile Gln Lys Leu Glu Gly Thr
            435                 440                 445

Thr Glu Leu Leu Val Gly Asn Phe Ala Gly Ala Asn Pro Asn Thr Arg
450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
            485                 490                 495

Phe Tyr Gly Arg Thr Ser Phe Pro Val
            500                 505

<210> SEQ ID NO 2
<211> LENGTH: 745
<212> TYPE: PRT
<213> ORGANISM: Artificial
<220> FEATURE:
<223> OTHER INFORMATION: CPTR

<400> SEQUENCE: 2

Met Gly Leu Ala Gly Arg Gly Val Ile Tyr Ile Pro Lys Asp Cys Gln
1               5                   10                  15

Ala Asn Arg Tyr Leu Gly Thr Leu Asn Ile Arg Asp Met Ile Ser Asp
            20                  25                  30

Phe Lys Gly Val Gln Tyr Glu Lys Trp Ile Thr Ala Gly Leu Val Met
            35                  40                  45

Pro Thr Phe Lys Ile Val Ile Arg Leu Pro Ala Asn Ala Phe Thr Gly
50                  55                  60

Leu Thr Trp Val Met Ser Phe Asp Ala Tyr Asn Arg Ile Thr Ser Arg
65                  70                  75                  80

Ile Thr Ala Ser Ala Asp Pro Val Tyr Thr Leu Ser Val Pro His Trp
            85                  90                  95

Leu Ile His His Lys Leu Gly Thr Phe Ser Cys Glu Ile Asp Tyr Gly
            100                 105                 110

Glu Leu Cys Gly His Ala Met Trp Phe Lys Ser Thr Thr Phe Glu Ser
            115                 120                 125

Pro Arg Leu His Phe Thr Cys Leu Thr Gly Asn Asn Lys Glu Leu Ala
130                 135                 140

Ala Asp Trp Gln Ala Val Val Glu Leu Tyr Ala Glu Leu Glu Glu Ala
145                 150                 155                 160

Thr Ser Phe Leu Gly Lys Pro Thr Leu Val Phe Asp Pro Gly Val Phe
            165                 170                 175

Asn Gly Lys Phe Gln Phe Leu Thr Cys Pro Pro Ile Phe Phe Asp Leu
            180                 185                 190

Thr Ala Val Thr Ala Leu Arg Ser Ala Gly Leu Thr Leu Gly Gln Val
            195                 200                 205
```

```
Pro Met Val Gly Thr Thr Lys Val Tyr Asn Leu Asn Ser Thr Leu Val
    210                 215                 220

Ser Cys Val Leu Gly Met Gly Gly Thr Val Arg Gly Arg Val His Ile
225                 230                 235                 240

Cys Ala Pro Ile Phe Tyr Ser Ile Val Leu Trp Val Val Ser Glu Trp
                245                 250                 255

Asn Gly Thr Thr Met Asp Trp Asn Glu Leu Phe Lys Tyr Pro Gly Val
                260                 265                 270

Tyr Val Glu Glu Asp Gly Ser Phe Glu Val Lys Ile Arg Ser Pro Tyr
                275                 280                 285

His Arg Thr Pro Ala Arg Leu Leu Ala Gly Gln Ser Gln Arg Asp Met
    290                 295                 300

Ser Ser Leu Asn Phe Tyr Ala Ile Ala Gly Pro Ile Ala Pro Ser Gly
305                 310                 315                 320

Glu Thr Ala Gln Leu Pro Ile Val Val Gln Ile Asp Glu Ile Val Arg
                325                 330                 335

Pro Asp Leu Ser Leu Pro Ser Phe Glu Asp Asp Tyr Phe Val Trp Val
                340                 345                 350

Asp Phe Ser Glu Phe Thr Leu Asp Lys Glu Glu Ile Glu Ile Gly Ser
                355                 360                 365

Arg Phe Phe Asp Phe Thr Ser Asn Thr Cys Arg Val Ser Met Gly Glu
    370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
                405                 410                 415

Ser Gly Ser Val Thr Ile Thr Lys Leu Val Gly Asp Lys Ala Met Gly
                420                 425                 430

Leu Asp Gly Pro Ser His Val Phe Ala Ile Gln Lys Leu Glu Gly Thr
    435                 440                 445

Thr Glu Leu Leu Val Gly Asn Phe Ala Gly Ala Asn Pro Asn Thr Arg
450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
                485                 490                 495

Phe Tyr Gly Arg Thr Ser Phe Pro Val Gly Gly Ser Gly Gly Gly
                500                 505                 510

Met Ser Glu Leu Ile Lys Glu Asn Met His Met Lys Leu Tyr Met Glu
    515                 520                 525

Gly Thr Val Asn Asn His His Phe Lys Cys Thr Ser Glu Gly Glu Gly
530                 535                 540

Lys Pro Tyr Glu Gly Thr Gln Thr Met Arg Ile Lys Val Val Glu Gly
545                 550                 555                 560

Gly Pro Leu Pro Phe Ala Phe Asp Ile Leu Ala Thr Ser Phe Met Tyr
                565                 570                 575

Gly Ser Arg Thr Phe Ile Asn His Thr Gln Gly Ile Pro Asp Phe Phe
                580                 585                 590

Lys Gln Ser Phe Pro Glu Gly Phe Thr Trp Glu Arg Val Thr Thr Tyr
                595                 600                 605

Glu Asp Gly Gly Val Leu Thr Ala Thr Gln Asp Thr Ser Leu Gln Asp
    610                 615                 620
```

```
Gly Cys Leu Ile Tyr Asn Val Lys Ile Arg Gly Val Asn Phe Pro Ser
625                 630                 635                 640

Asn Gly Pro Val Met Gln Lys Lys Thr Leu Gly Trp Glu Ala Asn Thr
            645                 650                 655

Glu Met Leu Tyr Pro Ala Asp Gly Gly Leu Glu Gly Arg Ser Asp Met
            660                 665                 670

Ala Leu Lys Leu Val Gly Gly Gly His Leu Ile Cys Asn Phe Lys Thr
            675                 680                 685

Thr Tyr Arg Ser Lys Lys Pro Ala Lys Asn Leu Lys Met Pro Gly Val
            690                 695                 700

Tyr Tyr Val Asp His Arg Leu Glu Arg Ile Lys Glu Ala Asp Lys Glu
705                 710                 715                 720

Thr Tyr Val Glu Gln His Glu Val Ala Val Ala Arg Tyr Cys Asp Leu
            725                 730                 735

Pro Ser Lys Leu Gly His Lys Leu Asn
            740                 745

<210> SEQ ID NO 3
<211> LENGTH: 744
<212> TYPE: PRT
<213> ORGANISM: Artificial
<220> FEATURE:
<223> OTHER INFORMATION: TRCP

<400> SEQUENCE: 3

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Met Tyr
50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
            115                 120                 125

Asn Gly Pro Val Met Gln Lys Lys Thr Leu Gly Trp Glu Ala Asn Thr
130                 135                 140

Glu Met Leu Tyr Pro Ala Asp Gly Gly Leu Glu Gly Arg Ser Asp Met
145                 150                 155                 160

Ala Leu Lys Leu Val Gly Gly Gly His Leu Ile Cys Asn Phe Lys Thr
                165                 170                 175

Thr Tyr Arg Ser Lys Lys Pro Ala Lys Asn Leu Lys Met Pro Gly Val
            180                 185                 190

Tyr Tyr Val Asp His Arg Leu Glu Arg Ile Lys Glu Ala Asp Lys Glu
            195                 200                 205

Thr Tyr Val Glu Gln His Glu Val Ala Val Ala Arg Tyr Cys Asp Leu
        210                 215                 220

Pro Ser Lys Leu Gly His Lys Leu Asn Gly Gly Ser Gly Gly Gly
225                 230                 235                 240
```

```
Gly Leu Ala Gly Arg Gly Val Ile Tyr Ile Pro Lys Asp Cys Gln Ala
                245                 250                 255

Asn Arg Tyr Leu Gly Thr Leu Asn Ile Arg Asp Met Ile Ser Asp Phe
            260                 265                 270

Lys Gly Val Gln Tyr Glu Lys Trp Ile Thr Ala Gly Leu Val Met Pro
        275                 280                 285

Thr Phe Lys Ile Val Ile Arg Leu Pro Ala Asn Ala Phe Thr Gly Leu
    290                 295                 300

Thr Trp Val Met Ser Phe Asp Ala Tyr Asn Arg Ile Thr Ser Arg Ile
305                 310                 315                 320

Thr Ala Ser Ala Asp Pro Val Tyr Thr Leu Ser Val Pro His Trp Leu
                325                 330                 335

Ile His His Lys Leu Gly Thr Phe Ser Cys Glu Ile Asp Tyr Gly Glu
            340                 345                 350

Leu Cys Gly His Ala Met Trp Phe Lys Ser Thr Thr Phe Glu Ser Pro
        355                 360                 365

Arg Leu His Phe Thr Cys Leu Thr Gly Asn Asn Lys Glu Leu Ala Ala
    370                 375                 380

Asp Trp Gln Ala Val Val Glu Leu Tyr Ala Glu Leu Glu Glu Ala Thr
385                 390                 395                 400

Ser Phe Leu Gly Lys Pro Thr Leu Val Phe Asp Pro Gly Val Phe Asn
                405                 410                 415

Gly Lys Phe Gln Phe Leu Thr Cys Pro Pro Ile Phe Phe Asp Leu Thr
            420                 425                 430

Ala Val Thr Ala Leu Arg Ser Ala Gly Leu Thr Leu Gly Gln Val Pro
        435                 440                 445

Met Val Gly Thr Thr Lys Val Tyr Asn Leu Asn Ser Thr Leu Val Ser
    450                 455                 460

Cys Val Leu Gly Met Gly Gly Thr Val Arg Gly Arg Val His Ile Cys
465                 470                 475                 480

Ala Pro Ile Phe Tyr Ser Ile Val Leu Trp Val Val Ser Glu Trp Asn
                485                 490                 495

Gly Thr Thr Met Asp Trp Asn Glu Leu Phe Lys Tyr Pro Gly Val Tyr
            500                 505                 510

Val Glu Glu Asp Gly Ser Phe Glu Val Lys Ile Arg Ser Pro Tyr His
        515                 520                 525

Arg Thr Pro Ala Arg Leu Leu Ala Gly Gln Ser Gln Arg Asp Met Ser
    530                 535                 540

Ser Leu Asn Phe Tyr Ala Ile Ala Gly Pro Ile Ala Pro Ser Gly Glu
545                 550                 555                 560

Thr Ala Gln Leu Pro Ile Val Val Gln Ile Asp Glu Ile Val Arg Pro
                565                 570                 575

Asp Leu Ser Leu Pro Ser Phe Glu Asp Asp Tyr Phe Val Trp Val Asp
            580                 585                 590

Phe Ser Glu Phe Thr Leu Asp Lys Glu Glu Ile Glu Ile Gly Ser Arg
        595                 600                 605

Phe Phe Asp Phe Thr Ser Asn Thr Cys Arg Val Ser Met Gly Glu Asn
    610                 615                 620

Pro Phe Ala Ala Met Ile Ala Cys His Gly Leu His Ser Gly Val Leu
625                 630                 635                 640

Asp Leu Lys Leu Gln Trp Ser Leu Asn Thr Glu Phe Gly Lys Ser Ser
                645                 650                 655
```

-continued

Gly Ser Val Thr Ile Thr Lys Leu Val Gly Asp Lys Ala Met Gly Leu
            660                 665                 670

Asp Gly Pro Ser His Val Phe Ala Ile Gln Lys Leu Glu Gly Thr Thr
        675                 680                 685

Glu Leu Leu Val Gly Asn Phe Ala Gly Ala Asn Pro Asn Thr Arg Phe
    690                 695                 700

Ser Leu Tyr Ser Arg Trp Met Ala Ile Lys Leu Asp Gln Ala Lys Ser
705                 710                 715                 720

Ile Lys Val Leu Arg Val Leu Cys Lys Pro Arg Pro Gly Phe Ser Phe
                725                 730                 735

Tyr Gly Arg Thr Ser Phe Pro Val
            740

<210> SEQ ID NO 4
<211> LENGTH: 761
<212> TYPE: PRT
<213> ORGANISM: Artificial
<220> FEATURE:
<223> OTHER INFORMATION: CPEG

<400> SEQUENCE: 4

Met Gly Leu Ala Gly Arg Gly Val Ile Tyr Ile Pro Lys Asp Cys Gln
1               5                   10                  15

Ala Asn Arg Tyr Leu Gly Thr Leu Asn Ile Arg Asp Met Ile Ser Asp
            20                  25                  30

Phe Lys Gly Val Gln Tyr Glu Lys Trp Ile Thr Ala Gly Leu Val Met
        35                  40                  45

Pro Thr Phe Lys Ile Val Ile Arg Leu Pro Ala Asn Ala Phe Thr Gly
    50                  55                  60

Leu Thr Trp Val Met Ser Phe Asp Ala Tyr Asn Arg Ile Thr Ser Arg
65                  70                  75                  80

Ile Thr Ala Ser Ala Asp Pro Val Tyr Thr Leu Ser Val Pro His Trp
                85                  90                  95

Leu Ile His His Lys Leu Gly Thr Phe Ser Cys Glu Ile Asp Tyr Gly
            100                 105                 110

Glu Leu Cys Gly His Ala Met Trp Phe Lys Ser Thr Thr Phe Glu Ser
        115                 120                 125

Pro Arg Leu His Phe Thr Cys Leu Thr Gly Asn Asn Lys Glu Leu Ala
    130                 135                 140

Ala Asp Trp Gln Ala Val Val Glu Leu Tyr Ala Glu Leu Glu Glu Ala
145                 150                 155                 160

Thr Ser Phe Leu Gly Lys Pro Thr Leu Val Phe Asp Pro Gly Val Phe
                165                 170                 175

Asn Gly Lys Phe Gln Phe Leu Thr Cys Pro Pro Ile Phe Phe Asp Leu
            180                 185                 190

Thr Ala Val Thr Ala Leu Arg Ser Ala Gly Leu Thr Leu Gly Gln Val
        195                 200                 205

Pro Met Val Gly Thr Thr Lys Val Tyr Asn Leu Asn Ser Thr Leu Val
    210                 215                 220

Ser Cys Val Leu Gly Met Gly Gly Thr Val Arg Gly Arg Val His Ile
225                 230                 235                 240

Cys Ala Pro Ile Phe Tyr Ser Ile Val Leu Trp Val Val Ser Glu Trp
                245                 250                 255

Asn Gly Thr Thr Met Asp Trp Asn Glu Leu Phe Lys Tyr Pro Gly Val
            260                 265                 270

```
Tyr Val Glu Glu Asp Gly Ser Phe Glu Val Lys Ile Arg Ser Pro Tyr
            275                 280                 285

His Arg Thr Pro Ala Arg Leu Leu Ala Gly Gln Ser Gln Arg Asp Met
    290                 295                 300

Ser Ser Leu Asn Phe Tyr Ala Ile Ala Gly Pro Ile Ala Pro Ser Gly
305                 310                 315                 320

Glu Thr Ala Gln Leu Pro Ile Val Gln Ile Asp Glu Ile Val Arg
                325                 330                 335

Pro Asp Leu Ser Leu Pro Ser Phe Glu Asp Tyr Phe Val Trp Val
                340                 345                 350

Asp Phe Ser Glu Phe Thr Leu Asp Lys Glu Glu Ile Glu Ile Gly Ser
            355                 360                 365

Arg Phe Phe Asp Phe Thr Ser Asn Thr Cys Arg Val Ser Met Gly Glu
    370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
                405                 410                 415

Ser Gly Ser Val Thr Ile Thr Lys Leu Val Gly Asp Lys Ala Met Gly
            420                 425                 430

Leu Asp Gly Pro Ser His Val Phe Ala Ile Gln Lys Leu Glu Gly Thr
                435                 440                 445

Thr Glu Leu Leu Val Gly Asn Phe Ala Gly Ala Asn Pro Asn Thr Arg
    450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
                485                 490                 495

Phe Tyr Gly Arg Thr Ser Phe Pro Val Asp Pro Ala Phe Leu Tyr Lys
            500                 505                 510

Val Val Arg Ser Phe Gly Pro Ala Met Val Ser Lys Gly Glu Glu Leu
    515                 520                 525

Phe Thr Gly Val Val Pro Ile Leu Val Glu Leu Asp Gly Asp Val Asn
530                 535                 540

Gly His Lys Phe Ser Val Ser Gly Glu Gly Glu Gly Asp Ala Thr Tyr
545                 550                 555                 560

Gly Lys Leu Thr Leu Lys Phe Ile Cys Thr Thr Gly Lys Leu Pro Val
                565                 570                 575

Pro Trp Pro Thr Leu Val Thr Thr Leu Thr Tyr Gly Val Gln Cys Phe
            580                 585                 590

Ser Arg Tyr Pro Asp His Met Lys Gln His Asp Phe Phe Lys Ser Ala
    595                 600                 605

Met Pro Glu Gly Tyr Val Gln Glu Arg Thr Ile Phe Phe Lys Asp Asp
    610                 615                 620

Gly Asn Tyr Lys Thr Arg Ala Glu Val Lys Phe Glu Gly Asp Thr Leu
625                 630                 635                 640

Val Asn Arg Ile Glu Leu Lys Gly Ile Asp Phe Lys Glu Asp Gly Asn
                645                 650                 655

Ile Leu Gly His Lys Leu Glu Tyr Asn Tyr Asn Ser His Asn Val Tyr
            660                 665                 670

Ile Met Ala Asp Lys Gln Lys Asn Gly Ile Lys Val Asn Phe Lys Ile
                675                 680                 685
```

```
Arg His Asn Ile Glu Asp Gly Ser Val Gln Leu Ala Asp His Tyr Gln
            690                 695                 700
Gln Asn Thr Pro Ile Gly Asp Gly Pro Val Leu Leu Pro Asp Asn His
705                 710                 715                 720
Tyr Leu Ser Thr Gln Ser Ala Leu Ser Lys Asp Pro Asn Glu Lys Arg
                725                 730                 735
Asp His Met Val Leu Leu Glu Phe Val Thr Ala Ala Gly Ile Thr Leu
            740                 745                 750
Gly Met Asp Glu Leu Tyr Lys Thr Ser
            755                 760

<210> SEQ ID NO 5
<211> LENGTH: 231
<212> TYPE: PRT
<213> ORGANISM: Artificial
<220> FEATURE:
<223> OTHER INFORMATION: TR

<400> SEQUENCE: 5

Met Ser Glu Leu Ile Lys Glu Asn Met His Met Lys Leu Tyr Met Glu
1               5                   10                  15
Gly Thr Val Asn Asn His His Phe Lys Cys Thr Ser Glu Gly Glu Gly
            20                  25                  30
Lys Pro Tyr Glu Gly Thr Gln Thr Met Arg Ile Lys Val Val Glu Gly
        35                  40                  45
Gly Pro Leu Pro Phe Ala Phe Asp Ile Leu Ala Thr Ser Phe Met Tyr
    50                  55                  60
Gly Ser Arg Thr Phe Ile Asn His Thr Gln Gly Ile Pro Asp Phe Phe
65                  70                  75                  80
Lys Gln Ser Phe Pro Glu Gly Phe Thr Trp Glu Arg Val Thr Thr Tyr
                85                  90                  95
Glu Asp Gly Gly Val Leu Thr Ala Thr Gln Asp Thr Ser Leu Gln Asp
            100                 105                 110
Gly Cys Leu Ile Tyr Asn Val Lys Ile Arg Gly Val Asn Phe Pro Ser
        115                 120                 125
Asn Gly Pro Val Met Gln Lys Lys Thr Leu Gly Trp Glu Ala Asn Thr
    130                 135                 140
Glu Met Leu Tyr Pro Ala Asp Gly Gly Leu Glu Gly Arg Ser Asp Met
145                 150                 155                 160
Ala Leu Lys Leu Val Gly Gly Gly His Leu Ile Cys Asn Phe Lys Thr
                165                 170                 175
Thr Tyr Arg Ser Lys Lys Pro Ala Lys Asn Leu Lys Met Pro Gly Val
            180                 185                 190
Tyr Tyr Val Asp His Arg Leu Glu Arg Ile Lys Glu Ala Asp Lys Glu
        195                 200                 205
Thr Tyr Val Glu Gln His Glu Val Ala Val Ala Arg Tyr Cys Asp Leu
    210                 215                 220
Pro Ser Lys Leu Gly His Asn
225                 230

<210> SEQ ID NO 6
<211> LENGTH: 15
<212> TYPE: PRT
<213> ORGANISM: Artificial
<220> FEATURE:
<223> OTHER INFORMATION: Linker
```

```
<400> SEQUENCE: 6

Asp Pro Ala Phe Leu Tyr Lys Val Val Arg Ser Phe Gly Pro Ala
1               5                   10                  15

<210> SEQ ID NO 7
<211> LENGTH: 131
<212> TYPE: PRT
<213> ORGANISM: Artificial
<220> FEATURE:
<223> OTHER INFORMATION: Nb126

<400> SEQUENCE: 7

Gln Val Gln Leu Gln Glu Ser Gly Gly Gly Ser Val Gln Val Gly Gly
1               5                   10                  15

Ser Leu Arg Leu Ala Cys Ala Ala Ser Gly Asp Thr Phe Ser Gly Tyr
            20                  25                  30

Leu Ala Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asn Ser Val
    50                  55                  60

Lys Gly Arg Phe Thr Ile Ser Lys Asp Asn Ala Asp Asn Met Met Tyr
65                  70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

<210> SEQ ID NO 8
<211> LENGTH: 131
<212> TYPE: PRT
<213> ORGANISM: Artificial
<220> FEATURE:
<223> OTHER INFORMATION: Nb101

<400> SEQUENCE: 8

Gln Val Gln Leu Gln Glu Ser Gly Gly Gly Ser Val Gln Val Gly Gly
1               5                   10                  15

Ser Leu Arg Leu Ala Cys Ala Ala Ser Gly Asp Thr Phe Ser Gly Tyr
            20                  25                  30

Leu Ala Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asp Ser Val
    50                  55                  60

Lys Gly Arg Phe Thr Ile Ser Lys Asp Asn Ala Asp Asn Met Met Tyr
65                  70                  75                  80

Leu Glu Met Asn Gly Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130
```

```
<210> SEQ ID NO 9
<211> LENGTH: 131
<212> TYPE: PRT
<213> ORGANISM: Artificial
<220> FEATURE:
<223> OTHER INFORMATION: Nb23

<400> SEQUENCE: 9
```

Gln Val Gln Leu Gln Glu Ser Gly Gly Gly Ser Val Gln Val Gly Gly
1               5                   10                  15

Ser Leu Arg Val Ala Cys Ala Ala Ser Gly Asp Thr Phe Ser Gly Tyr
            20                  25                  30

Leu Ala Ala Trp Phe Arg Gln Ala Pro Gly Lys Gly Arg Glu Gly Val
        35                  40                  45

Ala Ala Ile Asn Ser Lys Arg His Thr Thr Ser Tyr Ala Asp Ser Val
    50                  55                  60

Lys Gly Arg Phe Thr Ile Ser Lys Asp Asn Ala Asp Asn Ile Met Tyr
65                  70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

```
<210> SEQ ID NO 10
<211> LENGTH: 131
<212> TYPE: PRT
<213> ORGANISM: Artificial
<220> FEATURE:
<223> OTHER INFORMATION: Nbp75

<400> SEQUENCE: 10
```

Gln Val Gln Leu Gln Glu Ser Gly Gly Gly Ser Val Gln Ala Gly Gly
1               5                   10                  15

Ser Leu Arg Leu Ser Cys Val Ala Ser Glu Tyr Pro Ser Ser Ser Thr
            20                  25                  30

Ala Met Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asp Ser Val
    50                  55                  60

Lys Gly Arg Phe Thr Ile Ser Lys Asp Asn Ala Asp Asn Met Met Tyr
65                  70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

```
<210> SEQ ID NO 11
<211> LENGTH: 131
<212> TYPE: PRT
```

```
<213> ORGANISM: Artificial
<220> FEATURE:
<223> OTHER INFORMATION: Nbp71

<400> SEQUENCE: 11

Gln Val Gln Leu Gln Glu Ser Gly Gly Gly Ala Val Gln Pro Gly Gly
1               5                   10                  15

Ser Leu Lys Leu Ser Cys Glu Ala Ser Gly Asp Val Pro Glu Asn Gly
            20                  25                  30

Tyr Met Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asp Ser Val
    50                  55                  60

Lys Gly Arg Phe Thr Ile Ser Lys Asp Asn Ala Asp Asn Met Met Tyr
65                  70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
        130

<210> SEQ ID NO 12
<211> LENGTH: 126
<212> TYPE: PRT
<213> ORGANISM: artificial sequence
<220> FEATURE:
<223> OTHER INFORMATION: Nbp59

<400> SEQUENCE: 12

Gln Val Gln Leu Gln Glu Ser Gly Gly Gly Thr Val Gln Ala Gly Gly
1               5                   10                  15

Ser Leu Arg Leu Ser Cys Ser Ile Ser Gly Asp Thr Ser Asn Ser Tyr
            20                  25                  30

Cys Met Gly Trp Phe Arg Gln Ala Pro Gly Lys Glu Arg Glu Val Val
        35                  40                  45

Ala His Ile Ser Thr Gly Val Ile Ser Pro Gly Tyr Asn Lys Phe Ser
    50                  55                  60

Glu Gly Arg Phe Thr Ile Ser Pro Asp Asn Ala Lys Asn Ser Val Tyr
65                  70                  75                  80

Leu Gln Met Asn Asn Leu Lys Pro Asp Asp Thr Ala Met Tyr Tyr Cys
                85                  90                  95

Ala Ala Arg Thr Gly Tyr Cys Ser Gly Ser Trp Gly Val Ala Asp Ser
            100                 105                 110

Phe Asn Gly Trp Gly Gln Gly Thr Gln Val Thr Val Ser Ser
        115                 120                 125

<210> SEQ ID NO 13
<211> LENGTH: 127
<212> TYPE: PRT
<213> ORGANISM: artificial sequence
<220> FEATURE:
<223> OTHER INFORMATION: Nb125

<400> SEQUENCE: 13

Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Tyr Thr Tyr Ser Met Tyr
         20                  25                  30

Cys Met Ala Trp Phe Arg Gln Ala Pro Gly Lys Glu Arg Glu Gly Val
             35                  40                  45

Ala Ala Ile Asn Ser Gly Asn Arg Ser Thr Tyr Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Ile Met Asn Ser Leu Lys Pro Glu Asp Thr Ala Ile Tyr Tyr Cys
                 85                  90                  95

Ala Ala Asp Pro Gln Arg Cys Gly Ser Trp Thr Trp Ala Asn Met Tyr
                100                 105                 110

Glu Tyr Asn Tyr Trp Gly Gln Gly Thr Gln Val Thr Val Ser Ser
            115                 120                 125

<210> SEQ ID NO 14
<211> LENGTH: 125
<212> TYPE: PRT
<213> ORGANISM: artificial sequence
<220> FEATURE:
<223> OTHER INFORMATION: Nb155

<400> SEQUENCE: 14

Gln Val Gln Leu Gln Glu Ser Gly Gly Gly Ser Val Gln Ala Gly Glu
1               5                   10                  15

Ser Leu Arg Leu Ser Cys Thr Ala Ser Glu Leu Thr Phe Ser Asp Tyr
             20                  25                  30

Ile Met Asn Trp Phe Arg Gln Ala Gln Gly Lys Glu Cys Glu Arg Val
             35                  40                  45

Ser Met Ile Ile Gln Asn Gly Gly Asp Thr His Tyr Ala Asp Ser Val
 50                  55                  60

Lys Gly Arg Phe Thr Ile Ser Arg Asp Asn Thr Lys Ser Thr Leu His
 65                  70                  75                  80

Leu Gln Met Asn Asn Leu Arg Pro Asp Asp Thr Ala Val Tyr Tyr Cys
                 85                  90                  95

Ala Ala Gly Ala Leu Leu Pro Thr Phe Asn His Cys Pro Pro Pro Gly
                100                 105                 110

Ala Tyr Phe Gly Gln Gly Thr Gln Val Thr Val Ser Ser
            115                 120                 125

<210> SEQ ID NO 15
<211> LENGTH: 126
<212> TYPE: PRT
<213> ORGANISM: artificial sequence
<220> FEATURE:
<223> OTHER INFORMATION: Nb37

<400> SEQUENCE: 15

Gln Val Gln Leu Gln Glu Ser Gly Gly Gly Thr Val Gln Ala Gly Gly
1               5                   10                  15

Ser Leu Arg Leu Ser Cys Ser Ile Ser Gly Asp Thr Asn Ser Tyr
             20                  25                  30

Cys Met Gly Trp Phe Arg Gln Ala Pro Gly Lys Glu Arg Glu Val Val
             35                  40                  45

Ala His Ile Ser Thr Asn Asn Ile Ser Pro Ala Tyr Asn Lys Phe Arg
 50                  55                  60
```

```
Glu Gly Arg Phe Thr Ile Ser Pro Asp Asn Ala Lys Asn Ser Val Tyr
65                  70                  75                  80

Leu Gln Met Asn Asn Leu Lys Pro Glu Asp Thr Ala Met Tyr Tyr Cys
                85                  90                  95

Ala Ala Arg Thr Gly Tyr Cys Ser Gly Ser Trp Gly Val Ala Asp Ser
            100                 105                 110

Phe Asn Gly Trp Gly Gln Gly Thr Gln Val Thr Val Ser Ser
        115                 120                 125

<210> SEQ ID NO 16
<211> LENGTH: 126
<212> TYPE: PRT
<213> ORGANISM: artificial sequence
<220> FEATURE:
<223> OTHER INFORMATION: Nb77

<400> SEQUENCE: 16

Gln Val Gln Leu Gln Glu Ser Gly Gly Gly Thr Val Gln Ala Gly Gly
1               5                   10                  15

Ser Leu Arg Leu Ser Cys Ser Ile Ser Gly Asp Thr Ser Asn Ser Tyr
            20                  25                  30

Cys Met Gly Trp Phe Arg Gln Ala Pro Gly Lys Glu Arg Glu Val Val
            35                  40                  45

Ala His Ile Ser Thr Gly Val Ile Ser Pro Gly Tyr Asn Lys Phe Ala
        50                  55                  60

Glu Gly Arg Phe Thr Ile Ser Pro Asp Asn Ala Lys Asn Ser Val Tyr
65                  70                  75                  80

Leu Gln Met Asn Asn Leu Lys Pro Glu Asp Thr Ala Met Tyr Phe Cys
                85                  90                  95

Ala Ala Arg Thr Gly Ser Cys Ser Gly Ser Trp Gly Val Ala Asp Ser
            100                 105                 110

Phe Asn Gly Trp Gly Gln Gly Thr Gln Val Thr Val Ser Ser
        115                 120                 125

<210> SEQ ID NO 17
<211> LENGTH: 126
<212> TYPE: PRT
<213> ORGANISM: artificial sequence
<220> FEATURE:
<223> OTHER INFORMATION: Nb171

<400> SEQUENCE: 17

Gln Val Gln Leu Gln Glu Ser Gly Gly Gly Thr Val Gln Ala Gly Gly
1               5                   10                  15

Ser Leu Arg Leu Ser Cys Ser Ile Ser Gly Asp Thr Ser Asn Ser Tyr
            20                  25                  30

Cys Met Gly Trp Phe Arg Gln Ala Pro Gly Lys Glu Arg Glu Val Val
            35                  40                  45

Ala Arg Ile Ser Thr Gly Val Ile Ser Pro Gly Tyr Asn Lys Phe Ala
        50                  55                  60

Glu Gly Arg Phe Thr Ile Ser Pro Asp Asn Ala Lys Asn Ser Val Tyr
65                  70                  75                  80

Leu Gln Met Asn Asn Leu Lys Pro Glu Asp Thr Ala Met Tyr Phe Cys
                85                  90                  95

Ala Ala Arg Thr Gly Ser Cys Ser Gly Ser Trp Gly Val Ala Asp Ser
            100                 105                 110
```

```
Phe Asn Gly Trp Gly Gln Gly Thr Gln Val Thr Val Ser Ser
        115                 120                 125

<210> SEQ ID NO 18
<211> LENGTH: 127
<212> TYPE: PRT
<213> ORGANISM: artificial sequence
<220> FEATURE:
<223> OTHER INFORMATION: Nb159

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Met Tyr
            20                  25                  30

Cys Met Ala Trp Phe Arg Gln Ala Pro Gly Lys Glu Arg Glu Gly Val
        35                  40                  45

Ala Ala Ile Asn Ser Gly Gly Pro Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Ile Met Asn Ser Leu Lys Pro Glu Asp Thr Ala Ile Tyr Tyr Cys
                85                  90                  95

Ala Ala Asp Pro Gln Arg Cys Gly Ser Trp Ser Trp Ala Asn Met Tyr
            100                 105                 110

Glu Tyr Asn Tyr Trp Gly Gln Gly Thr Gln Val Thr Val Ser Ser
        115                 120                 125

<210> SEQ ID NO 19
<211> LENGTH: 127
<212> TYPE: PRT
<213> ORGANISM: artificial sequence
<220> FEATURE:
<223> OTHER INFORMATION: Nbp25

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Met Tyr
            20                  25                  30

Cys Met Gly Trp Phe Arg Gln Ala Pro Gly Lys Glu Arg Glu Gly Val
        35                  40                  45

Ala Ala Ile Asn Ser Gly Asn Gly Asn Thr Tyr Tyr Ala Asp Ser Val
    50                  55                  60

Lys Gly Arg Phe Thr Ile Ser Gln Asp Asn Ala Lys Asn Thr Met Tyr
65                  70                  75                  80

Leu Leu Met Asn Ser Leu Lys Pro Glu Asp Thr Ala Ile Tyr Tyr Cys
                85                  90                  95

Ala Ala Asp Pro Gln Arg Cys Gly Ser Trp Thr Trp Ala Gly Val Phe
            100                 105                 110

Glu Tyr Asn Tyr Trp Gly Gln Gly Thr Gln Val Thr Val Ser Ser
        115                 120                 125

<210> SEQ ID NO 20
<211> LENGTH: 125
<212> TYPE: PRT
<213> ORGANISM: artificial sequence
<220> FEATURE:
<223> OTHER INFORMATION: Nb172
```

<400> SEQUENCE: 20

Gln Val Gln Leu Gln Glu Ser Gly Gly Gly Ser Val Gln Ala Gly Glu
1               5                   10                  15

Ser Leu Arg Leu Ser Cys Thr Ala Ser Gly Ile Thr Phe Ser Asp Tyr
            20                  25                  30

Phe Met Asn Trp Phe Arg Gln Ala Gln Gly Lys Glu Cys Glu Arg Val
        35                  40                  45

Ser Met Ile Ser Met Asn Gly Ala Asp Thr His Tyr Ala Asp Ser Val
    50                  55                  60

Lys Gly Arg Phe Thr Ile Ser Arg Asp Asn Thr Lys Ser Thr Leu His
65                  70                  75                  80

Leu Gln Met Asn Asn Leu Arg Pro Asp Asp Thr Ala Val Tyr Tyr Cys
                85                  90                  95

Ala Ala Gly Ala Leu Leu Pro Ser Tyr Asn His Cys Pro Pro Pro Gly
            100                 105                 110

Ala Tyr Phe Gly Gln Gly Thr Gln Val Thr Val Ser Ser
        115                 120                 125

<210> SEQ ID NO 21
<211> LENGTH: 129
<212> TYPE: PRT
<213> ORGANISM: artificial sequence
<220> FEATURE:
<223> OTHER INFORMATION: Nb122

<400> SEQUENCE: 21

Gln Val Gln Leu Gln Glu Ser Gly Gly Gly Ser Val Gln Gly Gly Gly
1               5                   10                  15

Ser Leu Arg Leu Ser Cys Ala Val Ser Gly Tyr Arg Phe Ser Ser Tyr
            20                  25                  30

Ala Met Ala Trp Phe Arg Gln Ala Pro Gly Lys Glu Arg Glu Ala Val
        35                  40                  45

Ala Ala Tyr Tyr Arg Gly Phe Gly Gly Ala Gln His Ser Thr His Tyr
    50                  55                  60

Ala Ala Ser Val Thr Gly Arg Phe Thr Ile Thr Gln Asn Asp Ala Leu
65                  70                  75                  80

Asn Thr Gly Tyr Leu Gln Met Asn Asn Leu Lys Pro Glu Asp Thr Ala
                85                  90                  95

Met Tyr Tyr Cys Ala Leu Ser Thr Ala Asp Asp Asp Trp His Ser
            100                 105                 110

Leu Arg Arg Tyr Asn Tyr Trp Gly Gln Gly Thr Gln Val Thr Val Ser
        115                 120                 125

Ser

<210> SEQ ID NO 22
<211> LENGTH: 129
<212> TYPE: PRT
<213> ORGANISM: artificial sequence
<220> FEATURE:
<223> OTHER INFORMATION: Nb15

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Ala Thr Ser Gly Tyr Thr Leu Arg Pro Tyr
            20                  25                  30

```
Cys Met Gly Trp Phe Arg Gln Ala Pro Gly Lys Glu Arg Glu Gly Val
            35                  40                  45

Ala Thr Ile Thr Arg Ser Gly Asp Arg Thr Tyr Tyr Ala Asp Ala Val
 50                      55                  60

Lys Gly Arg Phe Thr Ile Ser Gln Asp Thr Ala Lys Asn Thr Val Tyr
 65                  70                  75                  80

Leu Gln Met Asn Asn Leu Lys Ser Glu Asp Ala Ala Asn Tyr Tyr Cys
                 85                  90                  95

Ala Ala Ser Phe Asn Tyr Leu Pro Thr Tyr Leu Thr Cys Gly Ser Arg
            100                 105                 110

Thr Ala Glu Tyr Asn Phe Trp Gly Gln Gly Thr Gln Val Thr Val Ser
            115                 120                 125

Ser
```

```
<210> SEQ ID NO 23
<211> LENGTH: 129
<212> TYPE: PRT
<213> ORGANISM: artificial sequence
<220> FEATURE:
<223> OTHER INFORMATION: Nbp77

<400> SEQUENCE: 23

Gln Val Gln Leu Gln Glu Ser Gly Gly Gly Ser Val Gln Ala Gly Gly
 1               5                  10                  15

Ser Leu Arg Leu Ser Cys Thr Thr Ser Gly Tyr Thr Leu Arg Pro Tyr
             20                  25                  30

Cys Met Gly Trp Phe Arg Gln Ala Pro Gly Lys Glu Arg Glu Gly Val
            35                  40                  45

Ala Thr Ile Thr Arg Ser Gly Asp Arg Thr Ser Tyr Ala Asp Ala Val
 50                      55                  60

Lys Gly Arg Phe Thr Ile Ser Gln Asp Thr Ala Lys Asn Thr Val Tyr
 65                  70                  75                  80

Leu Gln Met Asn Asn Leu Lys Ser Glu Asp Ala Ala Asn Tyr Tyr Cys
                 85                  90                  95

Ala Ala Ser Phe Asn Tyr Arg Pro Thr Tyr Val Thr Cys Asn Ser Arg
            100                 105                 110

Thr Ala Glu Tyr Asn Phe Trp Gly Gln Gly Thr Gln Val Thr Val Ser
            115                 120                 125

Ser
```

```
<210> SEQ ID NO 24
<211> LENGTH: 135
<212> TYPE: PRT
<213> ORGANISM: artificial sequence
<220> FEATURE:
<223> OTHER INFORMATION: Nb34

<400> SEQUENCE: 24

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Tyr Ser Ser Tyr
             20                  25                  30

Cys Met Gly Trp Phe Arg Gln Ala Pro Gly Lys Glu Arg Glu Gly Val
            35                  40                  45

Ala Thr Ile Asp Ser Gly Ser Gly Arg Thr Tyr Tyr Ala Asp Ser Val
 50                      55                  60
```

```
Lys Gly Arg Phe Thr Ile Ser Arg Asp Asn Ala Lys Asp Thr Val Tyr
 65                  70                  75                  80

Leu Leu Met Asn Asn Leu Lys Pro Glu Asp Thr Ala Ile Tyr Tyr Cys
                 85                  90                  95

Ala Ala Val Gly Ala Asn Ser Gly Gly Leu Trp Ser Ser Cys Gly Tyr
            100                 105                 110

Cys Tyr Gly Gly Leu Cys Gly Asp Asp Phe Gly Tyr Trp Gly Gln Gly
        115                 120                 125

Thr Gln Val Thr Val Ser Ser
        130                 135

<210> SEQ ID NO 25
<211> LENGTH: 135
<212> TYPE: PRT
<213> ORGANISM: artificial sequence
<220> FEATURE:
<223> OTHER INFORMATION: Nb80

<400> SEQUENCE: 25

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Tyr Ser Ser Tyr
             20                  25                  30

Cys Met Gly Trp Phe Arg Gln Ala Pro Gly Lys Glu Arg Glu Gly Val
         35                  40                  45

Ala Thr Ile Asp Ser Gly Ser Gly Arg Thr Tyr Tyr Ala Asp Ser Val
     50                  55                  60

Lys Gly Arg Phe Thr Ile Ser Gln Asp Asn Ala Lys Asn Thr Val Tyr
 65                  70                  75                  80

Leu Leu Met Asn Asn Leu Lys Pro Glu Asp Thr Ala Ile Tyr Tyr Cys
                 85                  90                  95

Ala Ala Val Gly Ala Asn Ser Gly Gly Leu Trp Ser Ser Cys Gly Tyr
            100                 105                 110

Cys Tyr Gly Gly Leu Cys Glu Asp Asp Phe Gly Tyr Trp Gly Gln Gly
        115                 120                 125

Thr Gln Val Thr Val Ser Ser
        130                 135

<210> SEQ ID NO 26
<211> LENGTH: 122
<212> TYPE: PRT
<213> ORGANISM: artificial sequence
<220> FEATURE:
<223> OTHER INFORMATION: Nb38

<400> SEQUENCE: 26

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr His Ser Ile Asn
             20                  25                  30

Leu Met Gly Trp Phe Arg Gln Ala Pro Gly Lys Glu Arg Glu Gly Val
         35                  40                  45

Ala Thr Ile Tyr Thr Val Gly Ser Ser Ser Tyr Tyr Ala Asp Ser
     50                  55                  60

Val Lys Gly Arg Phe Thr Ile Ser Leu Asp Asn Ala Lys Asn Thr Val
 65                  70                  75                  80
```

```
Tyr Leu Arg Met Asn Ser Leu Lys Pro Glu Asp Thr Ala Met Tyr Tyr
                85                  90                  95

Cys Ala Ala Gly Val Gly Trp Leu Ser Asn Ser Glu Tyr Asn Tyr Trp
            100                 105                 110

Gly Gln Gly Thr Gln Val Thr Val Ser Ser
        115                 120

<210> SEQ ID NO 27
<211> LENGTH: 120
<212> TYPE: PRT
<213> ORGANISM: artificial sequence
<220> FEATURE:
<223> OTHER INFORMATION: Nb137

<400> SEQUENCE: 27

Gln Val Gln Leu Gln Glu Ser Gly Gly Gly Ser Val Gln Ala Gly Gly
1               5                   10                  15

Ser Leu Lys Leu Ser Cys Arg Val Tyr Gly Tyr Ile Ala Ser Gln Cys
            20                  25                  30

Gly Met Gly Trp Tyr Arg Gln Ala Pro Gly Lys Gly Arg Glu Leu Val
            35                  40                  45

Thr Thr Ile Ser Ser Asp Gly Ser Thr Thr Tyr Ala Asp Ser Ile Lys
        50                  55                  60

Gly Arg Phe Thr Ile Ser Arg Asp Asn Val Glu Asn Thr Leu Tyr Leu
65                  70                  75                  80

Gln Met Asn Asn Leu Lys Pro Glu Asp Thr Ala Val Tyr Tyr Cys Ala
                85                  90                  95

Ala Asp Pro Leu Gly Asn Ser Cys Pro Gly Leu Ser Tyr Ser Ala Gln
            100                 105                 110

Gly Thr Gln Val Thr Val Ser Ser
        115                 120

<210> SEQ ID NO 28
<211> LENGTH: 128
<212> TYPE: PRT
<213> ORGANISM: artificial sequence
<220> FEATURE:
<223> OTHER INFORMATION: Nb139

<400> SEQUENCE: 28

Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Arg Asn
            20                  25                  30

Cys Met Gly Trp Phe Arg Gln Ala Pro Gly Lys Glu Arg Glu Gly Val
            35                  40                  45

Ala Ala Ile Tyr Thr Gly Ser Gly Asn Thr Asn Tyr Ala Asp Ser Val
        50                  55                  60

Lys Gly Arg Phe Thr Ile Ala Gln Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Ala Arg Asn Ser Gly Ser Trp Trp Arg Pro Ser Cys Asn Phe Asp
            100                 105                 110

Ser Asp Phe Gly Tyr Trp Gly Gln Gly Thr Gln Val Thr Val Ser Ser
            115                 120                 125
```

<210> SEQ ID NO 29
<211> LENGTH: 128
<212> TYPE: PRT
<213> ORGANISM: artificial sequence
<220> FEATURE:
<223> OTHER INFORMATION: Nbp12

<400> SEQUENCE: 29

```
Gln Val Gln Leu Gln Glu Ser Gly Gly Gly Ser Val Gln Ala Gly Gly
1               5                   10                  15

Ser Leu Arg Leu Ser Cys Lys Ala Ser Thr Tyr Thr Asn Ser Phe
            20                  25                  30

Cys Met Gly Trp Phe Arg Gln Ala Pro Gly Lys Glu Arg Glu Gly Val
        35                  40                  45

Ala Val Ile Gln Pro Gly Arg Asn Ser Lys Asp Tyr Ala Asp Ser Val
    50                  55                  60

Lys Gly Arg Phe Thr Ile Ser Gln Asp Asn Ala Leu Asn Thr Val Tyr
65                  70                  75                  80

Leu Gln Met Asn Ser Leu Lys Pro Glu Asp Thr Ala Met Tyr Tyr Cys
                85                  90                  95

Ala Ser Thr Gly Leu Trp Ile Ser Ser Gly Ser Cys Gln Thr Ile Pro
            100                 105                 110

Asp Gln Tyr Ser Tyr Trp Gly Gln Gly Thr Gln Val Thr Val Ser Ser
        115                 120                 125
```

<210> SEQ ID NO 30
<211> LENGTH: 1000
<212> TYPE: PRT
<213> ORGANISM: Artificial
<220> FEATURE:
<223> OTHER INFORMATION: TRCPEG

<400> SEQUENCE: 30

```
Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Asn Thr
    130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ile Cys Asn Phe Lys Thr
                165                 170                 175

Thr Tyr Arg Ser Lys Lys Pro Ala Lys Asn Leu Lys Met Pro Gly Val
            180                 185                 190
```

```
Tyr Tyr Val Asp His Arg Leu Glu Arg Ile Lys Glu Ala Asp Lys Glu
            195                 200                 205

Thr Tyr Val Glu Gln His Glu Val Ala Val Ala Arg Tyr Cys Asp Leu
    210                 215                 220

Pro Ser Lys Leu Gly His Lys Leu Asn Gly Gly Ser Gly Gly Gly
225                 230                 235                 240

Gly Leu Ala Gly Arg Gly Val Ile Tyr Ile Pro Lys Asp Cys Gln Ala
                245                 250                 255

Asn Arg Tyr Leu Gly Thr Leu Asn Ile Arg Asp Met Ile Ser Asp Phe
            260                 265                 270

Lys Gly Val Gln Tyr Glu Lys Trp Ile Thr Ala Gly Leu Val Met Pro
        275                 280                 285

Thr Phe Lys Ile Val Ile Arg Leu Pro Ala Asn Ala Phe Thr Gly Leu
    290                 295                 300

Thr Trp Val Met Ser Phe Asp Ala Tyr Asn Arg Ile Thr Ser Arg Ile
305                 310                 315                 320

Thr Ala Ser Ala Asp Pro Val Tyr Thr Leu Ser Val Pro His Trp Leu
                325                 330                 335

Ile His His Lys Leu Gly Thr Phe Ser Cys Glu Ile Asp Tyr Gly Glu
            340                 345                 350

Leu Cys Gly His Ala Met Trp Phe Lys Ser Thr Thr Phe Glu Ser Pro
        355                 360                 365

Arg Leu His Phe Thr Cys Leu Thr Gly Asn Asn Lys Glu Leu Ala Ala
    370                 375                 380

Asp Trp Gln Ala Val Val Glu Leu Tyr Ala Glu Leu Glu Glu Ala Thr
385                 390                 395                 400

Ser Phe Leu Gly Lys Pro Thr Leu Val Phe Asp Pro Gly Val Phe Asn
                405                 410                 415

Gly Lys Phe Gln Phe Leu Thr Cys Pro Pro Ile Phe Phe Asp Leu Thr
            420                 425                 430

Ala Val Thr Ala Leu Arg Ser Ala Gly Leu Thr Leu Gly Gln Val Pro
        435                 440                 445

Met Val Gly Thr Thr Lys Val Tyr Asn Leu Asn Ser Thr Leu Val Ser
    450                 455                 460

Cys Val Leu Gly Met Gly Gly Thr Val Arg Gly Arg Val His Ile Cys
465                 470                 475                 480

Ala Pro Ile Phe Tyr Ser Ile Val Leu Trp Val Val Ser Glu Trp Asn
                485                 490                 495

Gly Thr Thr Met Asp Trp Asn Glu Leu Phe Lys Tyr Pro Gly Val Tyr
            500                 505                 510

Val Glu Glu Asp Gly Ser Phe Glu Val Lys Ile Arg Ser Pro Tyr His
        515                 520                 525

Arg Thr Pro Ala Arg Leu Leu Ala Gly Gln Ser Gln Arg Asp Met Ser
    530                 535                 540

Ser Leu Asn Phe Tyr Ala Ile Ala Gly Pro Ile Ala Pro Ser Gly Glu
545                 550                 555                 560

Thr Ala Gln Leu Pro Ile Val Val Gln Ile Asp Glu Ile Val Arg Pro
                565                 570                 575

Asp Leu Ser Leu Pro Ser Phe Glu Asp Asp Tyr Phe Val Trp Val Asp
            580                 585                 590

Phe Ser Glu Phe Thr Leu Asp Lys Glu Glu Ile Glu Ile Gly Ser Arg
        595                 600                 605
```

Phe Phe Asp Phe Thr Ser Asn Thr Cys Arg Val Ser Met Gly Glu Asn
    610                 615                 620

Pro Phe Ala Ala Met Ile Ala Cys His Gly Leu His Ser Gly Val Leu
625                 630                 635                 640

Asp Leu Lys Leu Gln Trp Ser Leu Asn Thr Glu Phe Gly Lys Ser Ser
            645                 650                 655

Gly Ser Val Thr Ile Thr Lys Leu Val Gly Asp Lys Ala Met Gly Leu
                660                 665                 670

Asp Gly Pro Ser His Val Phe Ala Ile Gln Lys Leu Glu Gly Thr Thr
            675                 680                 685

Glu Leu Leu Val Gly Asn Phe Ala Gly Ala Asn Pro Asn Thr Arg Phe
    690                 695                 700

Ser Leu Tyr Ser Arg Trp Met Ala Ile Lys Leu Asp Gln Ala Lys Ser
705                 710                 715                 720

Ile Lys Val Leu Arg Val Leu Cys Lys Pro Arg Pro Gly Phe Ser Phe
            725                 730                 735

Tyr Gly Arg Thr Ser Phe Pro Val Asp Pro Ala Phe Leu Tyr Lys Val
                740                 745                 750

Val Arg Ser Phe Gly Pro Ala Met Val Ser Lys Gly Glu Glu Leu Phe
            755                 760                 765

Thr Gly Val Val Pro Ile Leu Val Glu Leu Asp Gly Asp Val Asn Gly
    770                 775                 780

His Lys Phe Ser Val Ser Gly Glu Gly Glu Gly Asp Ala Thr Tyr Gly
785                 790                 795                 800

Lys Leu Thr Leu Lys Phe Ile Cys Thr Thr Gly Lys Leu Pro Val Pro
            805                 810                 815

Trp Pro Thr Leu Val Thr Thr Leu Thr Tyr Gly Val Gln Cys Phe Ser
                820                 825                 830

Arg Tyr Pro Asp His Met Lys Gln His Asp Phe Phe Lys Ser Ala Met
            835                 840                 845

Pro Glu Gly Tyr Val Gln Glu Arg Thr Ile Phe Phe Lys Asp Asp Gly
    850                 855                 860

Asn Tyr Lys Thr Arg Ala Glu Val Lys Phe Glu Gly Asp Thr Leu Val
865                 870                 875                 880

Asn Arg Ile Glu Leu Lys Gly Ile Asp Phe Lys Glu Asp Gly Asn Ile
            885                 890                 895

Leu Gly His Lys Leu Glu Tyr Asn Tyr Asn Ser His Asn Val Tyr Ile
                900                 905                 910

Met Ala Asp Lys Gln Lys Asn Gly Ile Lys Val Asn Phe Lys Ile Arg
            915                 920                 925

His Asn Ile Glu Asp Gly Ser Val Gln Leu Ala Asp His Tyr Gln Gln
    930                 935                 940

Asn Thr Pro Ile Gly Asp Gly Pro Val Leu Leu Pro Asp Asn His Tyr
945                 950                 955                 960

Leu Ser Thr Gln Ser Ala Leu Ser Lys Asp Pro Asn Glu Lys Arg Asp
            965                 970                 975

His Met Val Leu Leu Glu Phe Val Thr Ala Ala Gly Ile Thr Leu Gly
                980                 985                 990

Met Asp Glu Leu Tyr Lys Thr Ser
    995                 1000

<210> SEQ ID NO 31
<211> LENGTH: 385

```
<212> TYPE: PRT
<213> ORGANISM: Artificial
<220> FEATURE:
<223> OTHER INFORMATION: Nb23EGFP

<400> SEQUENCE: 31
```

| | | | | | | | | | | | | | | |
|---|---|---|---|---|---|---|---|---|---|---|---|---|---|---|
| Gln | Val | Gln | Leu | Gln | Glu | Ser | Gly | Gly | Gly | Ser | Val | Gln | Val | Gly | Gly |
| 1 | | | | 5 | | | | | 10 | | | | | 15 |

| Ser | Leu | Arg | Val | Ala | Cys | Ala | Ala | Ser | Gly | Asp | Thr | Phe | Ser | Gly | Tyr |
| | | | 20 | | | | | 25 | | | | | 30 | |

| Leu | Ala | Ala | Trp | Phe | Arg | Gln | Ala | Pro | Gly | Lys | Gly | Arg | Glu | Gly | Val |
| | | 35 | | | | | 40 | | | | | 45 | | |

| Ala | Ala | Ile | Asn | Ser | Lys | Arg | His | Thr | Thr | Ser | Tyr | Ala | Asp | Ser | Val |
| | 50 | | | | | 55 | | | | | 60 | | | | |

| Lys | Gly | Arg | Phe | Thr | Ile | Ser | Lys | Asp | Asn | Ala | Asp | Asn | Ile | Met | Tyr |
| 65 | | | | | 70 | | | | | 75 | | | | | 80 |

| Leu | Glu | Met | Asn | Ser | Leu | Lys | Pro | Glu | Asp | Thr | Ala | Ile | Tyr | Tyr | Cys |
| | | | | 85 | | | | | 90 | | | | | 95 | |

| Ala | Ala | Ala | Asp | Ala | Ile | Gly | Leu | Ala | Glu | Tyr | Trp | Ser | Thr | Pro | Thr |
| | | | 100 | | | | | 105 | | | | | 110 | | |

| Leu | Ser | Ala | Ala | Arg | Tyr | Lys | Tyr | Trp | Gly | Gln | Gly | Thr | Gln | Val | Thr |
| | | 115 | | | | | 120 | | | | | 125 | | | |

| Val | Ser | Ser | Gly | Gly | Gly | Ser | Gly | Gly | Gly | Met | Val | Ser | Lys | Gly | Glu |
| | 130 | | | | | 135 | | | | | 140 | | | | |

| Glu | Leu | Phe | Thr | Gly | Val | Val | Pro | Ile | Leu | Val | Glu | Leu | Asp | Gly | Asp |
| 145 | | | | | 150 | | | | | 155 | | | | | 160 |

| Val | Asn | Gly | His | Lys | Phe | Ser | Val | Ser | Gly | Glu | Gly | Glu | Gly | Asp | Ala |
| | | | | 165 | | | | | 170 | | | | | 175 | |

| Thr | Tyr | Gly | Lys | Leu | Thr | Leu | Lys | Phe | Ile | Cys | Thr | Thr | Gly | Lys | Leu |
| | | | 180 | | | | | 185 | | | | | 190 | | |

| Pro | Val | Pro | Trp | Pro | Thr | Leu | Val | Thr | Thr | Leu | Thr | Tyr | Gly | Val | Gln |
| | | 195 | | | | | 200 | | | | | 205 | | | |

| Cys | Phe | Ser | Arg | Tyr | Pro | Asp | His | Met | Lys | Gln | His | Asp | Phe | Phe | Lys |
| | 210 | | | | | 215 | | | | | 220 | | | | |

| Ser | Ala | Met | Pro | Glu | Gly | Tyr | Val | Gln | Glu | Arg | Thr | Ile | Phe | Phe | Lys |
| 225 | | | | | 230 | | | | | 235 | | | | | 240 |

| Asp | Asp | Gly | Asn | Tyr | Lys | Thr | Arg | Ala | Glu | Val | Lys | Phe | Glu | Gly | Asp |
| | | | | 245 | | | | | 250 | | | | | 255 | |

| Thr | Leu | Val | Asn | Arg | Ile | Glu | Leu | Lys | Gly | Ile | Asp | Phe | Lys | Glu | Asp |
| | | | 260 | | | | | 265 | | | | | 270 | | |

| Gly | Asn | Ile | Leu | Gly | His | Lys | Leu | Glu | Tyr | Asn | Tyr | Asn | Ser | His | Asn |
| | | 275 | | | | | 280 | | | | | 285 | | | |

| Val | Tyr | Ile | Met | Ala | Asp | Lys | Gln | Lys | Asn | Gly | Ile | Lys | Val | Asn | Phe |
| | 290 | | | | | 295 | | | | | 300 | | | | |

| Lys | Ile | Arg | His | Asn | Ile | Glu | Asp | Gly | Ser | Val | Gln | Leu | Ala | Asp | His |
| 305 | | | | | 310 | | | | | 315 | | | | | 320 |

| Tyr | Gln | Gln | Asn | Thr | Pro | Ile | Gly | Asp | Gly | Pro | Val | Leu | Leu | Pro | Asp |
| | | | | 325 | | | | | 330 | | | | | 335 | |

| Asn | His | Tyr | Leu | Ser | Thr | Gln | Ser | Ala | Leu | Ser | Lys | Asp | Pro | Asn | Glu |
| | | | 340 | | | | | 345 | | | | | 350 | | |

| Lys | Arg | Asp | His | Met | Val | Leu | Leu | Glu | Phe | Val | Thr | Ala | Ala | Gly | Ile |
| | | 355 | | | | | 360 | | | | | 365 | | | |

-continued

Thr Leu Gly Met Asp Glu Leu Tyr Lys Thr Ser His His His His
            370                 375                 380

His
385

<210> SEQ ID NO 32
<211> LENGTH: 686
<212> TYPE: PRT
<213> ORGANISM: Artificial
<220> FEATURE:
<223> OTHER INFORMATION: Nb23ALP

<400> SEQUENCE: 32

Gln Val Gln Leu Gln Glu Ser Gly Gly Gly Ser Val Gln Val Gly Gly
1               5                   10                  15

Ser Leu Arg Val Ala Cys Ala Ala Ser Gly Asp Thr Phe Ser Gly Tyr
            20                  25                  30

Leu Ala Ala Trp Phe Arg Gln Ala Pro Gly Lys Gly Arg Glu Gly Val
        35                  40                  45

Ala Ala Ile Asn Ser Lys Arg His Thr Thr Ser Tyr Ala Asp Ser Val
    50                  55                  60

Lys Gly Arg Phe Thr Ile Ser Lys Asp Asn Ala Asp Asn Ile Met Tyr
65                  70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser Gly Gly Gly Ser Gly Gly Gly Val Lys Gln Ser Thr Ile
    130                 135                 140

Ala Leu Ala Leu Leu Pro Leu Leu Phe Thr Pro Val Thr Lys Ala Arg
145                 150                 155                 160

Thr Pro Glu Met Pro Leu Gln Thr Gln Ala Thr Ser Arg Glu Glu Pro
                165                 170                 175

Pro Arg Leu Pro Ser Lys His Arg Pro Gly Val Lys Thr Gln Ala Thr
            180                 185                 190

Ser Arg Glu Glu Pro Pro Arg Leu Pro Ser Lys His Arg Pro Gly Val
        195                 200                 205

Lys Thr Gln Ala Thr Ser Arg Glu Glu Pro Pro Arg Leu Pro Ser Lys
    210                 215                 220

His Arg Pro Gly Val Lys Thr Gln Ala Thr Ser Arg Glu Glu Pro Pro
225                 230                 235                 240

Arg Leu Pro Ser Lys His Arg Pro Gly Val Lys Thr Gln Ala Thr Ser
                245                 250                 255

Leu Glu Val Leu Glu Asn Arg Ala Ala Gln Gly Asp Ile Thr Ala Pro
            260                 265                 270

Gly Gly Ala Arg Arg Leu Thr Gly Asp Gln Thr Ala Ala Leu Arg Asp
        275                 280                 285

Ser Leu Ser Asp Lys Pro Ala Lys Asn Ile Ile Leu Leu Ile Gly Asp
    290                 295                 300

Gly Met Gly Asp Ser Glu Ile Thr Ala Ala Arg Asn Tyr Ala Glu Gly
305                 310                 315                 320

Ala Gly Gly Phe Phe Lys Gly Ile Asp Ala Leu Pro Leu Thr Gly Gln
                325                 330                 335

```
Tyr Thr His Tyr Ala Leu Asn Lys Lys Thr Gly Lys Pro Asp Tyr Val
            340                 345                 350

Thr Asp Ser Ala Ala Ser Ala Thr Ala Trp Ser Thr Gly Val Lys Thr
        355                 360                 365

Tyr Asn Gly Ala Leu Gly Val Asp Ile His Glu Lys Asp His Pro Thr
    370                 375                 380

Ile Leu Glu Met Ala Lys Ala Ala Gly Leu Ala Thr Gly Asn Val Ser
385                 390                 395                 400

Thr Ala Glu Leu Gln Asp Ala Thr Pro Ala Ala Leu Val Ala His Val
            405                 410                 415

Thr Ser Arg Lys Cys Tyr Gly Pro Ser Ala Thr Ser Glu Lys Cys Pro
        420                 425                 430

Gly Asn Ala Leu Glu Lys Gly Gly Lys Gly Ser Ile Thr Glu Gln Leu
    435                 440                 445

Leu Asn Ala Arg Ala Asp Val Thr Leu Gly Gly Ala Lys Thr Phe
450                 455                 460

Ala Glu Thr Ala Thr Ala Gly Glu Trp Gln Gly Lys Thr Leu Arg Glu
465                 470                 475                 480

Gln Ala Gln Ala Arg Gly Tyr Gln Leu Val Ser Asp Ala Ala Ser Leu
            485                 490                 495

Asn Ser Val Thr Glu Ala Asn Gln Gln Lys Pro Leu Leu Gly Leu Phe
        500                 505                 510

Ala Asp Gly Asn Met Pro Val Arg Trp Leu Gly Pro Lys Ala Thr Tyr
    515                 520                 525

His Gly Asn Ile Asp Lys Pro Ala Val Thr Cys Thr Pro Asn Pro Gln
530                 535                 540

Arg Asn Asp Ser Val Pro Thr Leu Ala Gln Met Thr Asp Lys Ala Ile
545                 550                 555                 560

Glu Leu Leu Ser Lys Asn Glu Lys Gly Phe Phe Leu Gln Val Glu Gly
            565                 570                 575

Ala Ser Ile Asp Lys Gln Asp His Ala Ala Asn Pro Cys Gly Gln Ile
        580                 585                 590

Gly Glu Thr Val Asp Leu Asp Glu Ala Val Gln Arg Ala Leu Glu Phe
    595                 600                 605

Ala Lys Lys Glu Gly Asn Thr Leu Val Ile Val Thr Ala Asp His Ala
610                 615                 620

His Ala Ser Gln Ile Val Ala Pro Asp Thr Lys Ala Pro Gly Leu Thr
625                 630                 635                 640

Gln Ala Leu Asn Thr Lys Asp Gly Ala Val Met Val Met Ser Tyr Gly
            645                 650                 655

Asn Ser Glu Glu Asp Ser Gln Glu His Thr Gly Ser Gln Leu Arg Ile
        660                 665                 670

Ala Ala Tyr Gly Pro His Ala Ala His His His His His
    675                 680                 685

<210> SEQ ID NO 33
<211> LENGTH: 686
<212> TYPE: PRT
<213> ORGANISM: artificial sequence
<220> FEATURE:
<223> OTHER INFORMATION: Nb122:ALP

<400> SEQUENCE: 33

Met Ala Gln Val Gln Leu Gln Glu Ser Gly Gly Gly Ser Val Gln Gly
1               5                   10                  15
```

-continued

```
Gly Gly Ser Leu Arg Leu Ser Cys Ala Val Ser Gly Tyr Arg Phe Ser
             20                  25                  30

Ser Tyr Ala Met Ala Trp Phe Arg Gln Ala Pro Gly Lys Glu Arg Glu
             35                  40                  45

Ala Val Ala Ala Tyr Tyr Arg Gly Phe Gly Gly Ala Gln His Ser Thr
 50                  55                  60

His Tyr Ala Ala Ser Val Thr Gly Arg Phe Thr Ile Thr Gln Asn Asp
 65                  70                  75                  80

Ala Leu Asn Thr Gly Tyr Leu Gln Met Asn Asn Leu Lys Pro Glu Asp
             85                  90                  95

Thr Ala Met Tyr Tyr Cys Ala Leu Ser Thr Ala Asp Asp Asp Asp Trp
            100                 105                 110

His Ser Leu Arg Arg Tyr Asn Tyr Trp Gly Gln Gly Thr Gln Val Thr
            115                 120                 125

Val Ser Ser Gly Gly Gly Ser Gly Gly Gly Val Lys Gln Ser Thr Ile
130                 135                 140

Ala Leu Ala Leu Leu Pro Leu Leu Phe Thr Pro Val Thr Lys Ala Arg
145                 150                 155                 160

Thr Pro Glu Met Pro Leu Gln Thr Gln Ala Thr Ser Arg Glu Glu Pro
            165                 170                 175

Pro Arg Leu Pro Ser Lys His Arg Pro Gly Val Lys Thr Gln Ala Thr
            180                 185                 190

Ser Arg Glu Glu Pro Pro Arg Leu Pro Ser Lys His Arg Pro Gly Val
            195                 200                 205

Lys Thr Gln Ala Thr Ser Arg Glu Glu Pro Pro Arg Leu Pro Ser Lys
210                 215                 220

His Arg Pro Gly Val Lys Thr Gln Ala Thr Ser Arg Glu Glu Pro Pro
225                 230                 235                 240

Arg Leu Pro Ser Lys His Arg Pro Gly Val Lys Thr Gln Ala Thr Ser
            245                 250                 255

Leu Glu Val Leu Glu Asn Arg Ala Ala Gln Gly Asp Ile Thr Ala Pro
            260                 265                 270

Gly Gly Ala Arg Arg Leu Thr Gly Asp Gln Thr Ala Ala Leu Arg Asp
            275                 280                 285

Ser Leu Ser Asp Lys Pro Ala Lys Asn Ile Ile Leu Leu Ile Gly Asp
            290                 295                 300

Gly Met Gly Asp Ser Glu Ile Thr Ala Ala Arg Asn Tyr Ala Glu Gly
305                 310                 315                 320

Ala Gly Gly Phe Phe Lys Gly Ile Asp Ala Leu Pro Leu Thr Gly Gln
            325                 330                 335

Tyr Thr His Tyr Ala Leu Asn Lys Lys Thr Gly Lys Pro Asp Tyr Val
            340                 345                 350

Thr Asp Ser Ala Ala Ser Ala Thr Ala Trp Ser Thr Gly Val Lys Thr
            355                 360                 365

Tyr Asn Gly Ala Leu Gly Val Asp Ile His Glu Lys Asp His Pro Thr
            370                 375                 380

Ile Leu Glu Met Ala Lys Ala Ala Gly Leu Ala Thr Gly Asn Val Ser
385                 390                 395                 400

Thr Ala Glu Leu Gln Asp Ala Thr Pro Ala Ala Leu Val Ala His Val
            405                 410                 415

Thr Ser Arg Lys Cys Tyr Gly Pro Ser Ala Thr Ser Glu Lys Cys Pro
            420                 425                 430
```

```
Gly Asn Ala Leu Glu Lys Gly Lys Gly Ser Ile Thr Glu Gln Leu
            435                 440                 445

Leu Asn Ala Arg Ala Asp Val Thr Leu Gly Gly Ala Lys Thr Phe
    450                 455                 460

Ala Glu Thr Ala Thr Ala Gly Glu Trp Gln Gly Lys Thr Leu Arg Glu
465                 470                 475                 480

Gln Ala Gln Ala Arg Gly Tyr Gln Leu Val Ser Asp Ala Ala Ser Leu
                485                 490                 495

Asn Ser Val Thr Glu Ala Asn Gln Gln Lys Pro Leu Leu Gly Leu Phe
            500                 505                 510

Ala Asp Gly Asn Met Pro Val Arg Trp Leu Gly Pro Lys Ala Thr Tyr
    515                 520                 525

His Gly Asn Ile Asp Lys Pro Ala Val Thr Cys Thr Pro Asn Pro Gln
530                 535                 540

Arg Asn Asp Ser Val Pro Thr Leu Ala Gln Met Thr Asp Lys Ala Ile
545                 550                 555                 560

Glu Leu Leu Ser Lys Asn Glu Lys Gly Phe Phe Leu Gln Val Glu Gly
                565                 570                 575

Ala Ser Ile Asp Lys Gln Asp His Ala Ala Asn Pro Cys Gly Gln Ile
            580                 585                 590

Gly Glu Thr Val Asp Leu Asp Glu Ala Val Gln Arg Ala Leu Glu Phe
    595                 600                 605

Ala Lys Lys Glu Gly Asn Thr Leu Val Ile Val Thr Ala Asp His Ala
610                 615                 620

His Ala Ser Gln Ile Val Ala Pro Asp Thr Lys Ala Pro Gly Leu Thr
625                 630                 635                 640

Gln Ala Leu Asn Thr Lys Asp Gly Ala Val Met Val Met Ser Tyr Gly
                645                 650                 655

Asn Ser Glu Glu Asp Ser Gln Glu His Thr Gly Ser Gln Leu Arg Ile
            660                 665                 670

Ala Ala Tyr Gly Pro His Ala Ala His His His His His
    675                 680                 685

<210> SEQ ID NO 34
<211> LENGTH: 5
<212> TYPE: PRT
<213> ORGANISM: artificial sequence
<220> FEATURE:
<223> OTHER INFORMATION: CDR1 Nb23

<400> SEQUENCE: 34

Gly Tyr Leu Ala Ala
1               5

<210> SEQ ID NO 35
<211> LENGTH: 17
<212> TYPE: PRT
<213> ORGANISM: artificial sequence
<220> FEATURE:
<223> OTHER INFORMATION: CDR2 Nb23

<400> SEQUENCE: 35

Ala Ile Asn Ser Lys Arg His Thr Thr Ser Tyr Ala Asp Ser Val Lys
1               5                   10                  15

Gly

<210> SEQ ID NO 36
<211> LENGTH: 22
```

```
<212> TYPE: PRT
<213> ORGANISM: artificial sequence
<220> FEATURE:
<223> OTHER INFORMATION: CDR3 Nb23

<400> SEQUENCE: 36

Ala Asp Ala Ile Gly Leu Ala Glu Tyr Trp Ser Thr Pro Thr Leu Ser
1               5                   10                  15

Ala Ala Arg Tyr Lys Tyr
            20

<210> SEQ ID NO 37
<211> LENGTH: 5
<212> TYPE: PRT
<213> ORGANISM: artificial sequence
<220> FEATURE:
<223> OTHER INFORMATION: CDR1 Nbp75

<400> SEQUENCE: 37

Ser Thr Ala Met Ala
1               5

<210> SEQ ID NO 38
<211> LENGTH: 17
<212> TYPE: PRT
<213> ORGANISM: artificial sequence
<220> FEATURE:
<223> OTHER INFORMATION: CDR2 Nbp75

<400> SEQUENCE: 38

Ala Ile Asn Ser Val Arg His Thr Thr Ser Tyr Ala Asp Ser Val Lys
1               5                   10                  15

Gly

<210> SEQ ID NO 39
<211> LENGTH: 22
<212> TYPE: PRT
<213> ORGANISM: artificial sequence
<220> FEATURE:
<223> OTHER INFORMATION: CDR3 Nbp75

<400> SEQUENCE: 39

Ala Asp Ala Ile Gly Leu Ala Glu Tyr Trp Ser Thr Pro Thr Leu Ser
1               5                   10                  15

Ala Ala Arg Tyr Lys Tyr
            20

<210> SEQ ID NO 40
<211> LENGTH: 5
<212> TYPE: PRT
<213> ORGANISM: artificial sequence
<220> FEATURE:
<223> OTHER INFORMATION: CDR1 Nb101

<400> SEQUENCE: 40

Gly Tyr Leu Ala Ala
1               5

<210> SEQ ID NO 41
<211> LENGTH: 17
<212> TYPE: PRT
<213> ORGANISM: artificial sequence
<220> FEATURE:
<223> OTHER INFORMATION: CDR2 Nb101
```

-continued

```
<400> SEQUENCE: 41

Ala Ile Asn Ser Val Arg His Thr Thr Ser Tyr Ala Asp Ser Val Lys
1               5                   10                  15

Gly

<210> SEQ ID NO 42
<211> LENGTH: 22
<212> TYPE: PRT
<213> ORGANISM: artificial sequence
<220> FEATURE:
<223> OTHER INFORMATION: CDR3 Nb101

<400> SEQUENCE: 42

Ala Asp Ala Ile Gly Leu Ala Glu Tyr Trp Ser Thr Pro Thr Leu Ser
1               5                   10                  15

Ala Ala Arg Tyr Lys Tyr
            20

<210> SEQ ID NO 43
<211> LENGTH: 5
<212> TYPE: PRT
<213> ORGANISM: artificial sequence
<220> FEATURE:
<223> OTHER INFORMATION: CDR1 Nb126

<400> SEQUENCE: 43

Gly Tyr Leu Ala Ala
1               5

<210> SEQ ID NO 44
<211> LENGTH: 17
<212> TYPE: PRT
<213> ORGANISM: artificial sequence
<220> FEATURE:
<223> OTHER INFORMATION: CDR2 Nb126

<400> SEQUENCE: 44

Ala Ile Asn Ser Val Arg His Thr Thr Ser Tyr Ala Asn Ser Val Lys
1               5                   10                  15

Gly

<210> SEQ ID NO 45
<211> LENGTH: 22
<212> TYPE: PRT
<213> ORGANISM: artificial sequence
<220> FEATURE:
<223> OTHER INFORMATION: CDR3 Nb126

<400> SEQUENCE: 45

Ala Asp Ala Ile Gly Leu Ala Glu Tyr Trp Ser Thr Pro Thr Leu Ser
1               5                   10                  15

Ala Ala Arg Tyr Lys Tyr
            20

<210> SEQ ID NO 46
<211> LENGTH: 5
<212> TYPE: PRT
<213> ORGANISM: artificial sequence
<220> FEATURE:
<223> OTHER INFORMATION: CDR1 Nbp71
```

```
<400> SEQUENCE: 46

Asn Gly Tyr Met Ala
1               5

<210> SEQ ID NO 47
<211> LENGTH: 17
<212> TYPE: PRT
<213> ORGANISM: artificial sequence
<220> FEATURE:
<223> OTHER INFORMATION: CDR2 Nbp71

<400> SEQUENCE: 47

Ala Ile Asn Ser Val Arg His Thr Thr Ser Tyr Ala Asp Ser Val Lys
1               5                   10                  15

Gly

<210> SEQ ID NO 48
<211> LENGTH: 22
<212> TYPE: PRT
<213> ORGANISM: artificial sequence
<220> FEATURE:
<223> OTHER INFORMATION: CDR3 Nbp71

<400> SEQUENCE: 48

Ala Asp Ala Ile Gly Leu Ala Glu Tyr Trp Ser Thr Pro Thr Leu Ser
1               5                   10                  15

Ala Ala Arg Tyr Lys Tyr
            20

<210> SEQ ID NO 49
<211> LENGTH: 5
<212> TYPE: PRT
<213> ORGANISM: artificial sequence
<220> FEATURE:
<223> OTHER INFORMATION: CDR1 Nbp59

<400> SEQUENCE: 49

Ser Tyr Cys Met Gly
1               5

<210> SEQ ID NO 50
<211> LENGTH: 17
<212> TYPE: PRT
<213> ORGANISM: artificial sequence
<220> FEATURE:
<223> OTHER INFORMATION: CDR2 Nbp59

<400> SEQUENCE: 50

His Ile Ser Thr Gly Val Ile Ser Pro Gly Tyr Asn Lys Phe Ser Glu
1               5                   10                  15

Gly

<210> SEQ ID NO 51
<211> LENGTH: 17
<212> TYPE: PRT
<213> ORGANISM: artificial sequence
<220> FEATURE:
<223> OTHER INFORMATION: CDR3 Nbp59

<400> SEQUENCE: 51

Arg Thr Gly Tyr Cys Ser Gly Ser Trp Gly Val Ala Asp Ser Phe Asn
1               5                   10                  15

Gly
```

```
<210> SEQ ID NO 52
<211> LENGTH: 5
<212> TYPE: PRT
<213> ORGANISM: artificial sequence
<220> FEATURE:
<223> OTHER INFORMATION: CDR1 Nb125

<400> SEQUENCE: 52

Met Tyr Cys Met Ala
1               5

<210> SEQ ID NO 53
<211> LENGTH: 17
<212> TYPE: PRT
<213> ORGANISM: artificial sequence
<220> FEATURE:
<223> OTHER INFORMATION: CDR2 Nb125

<400> SEQUENCE: 53

Ala Ile Asn Ser Gly Asn Arg Ser Thr Tyr Tyr Ala Asp Ser Val Lys
1               5                   10                  15
Gly

<210> SEQ ID NO 54
<211> LENGTH: 18
<212> TYPE: PRT
<213> ORGANISM: artificial sequence
<220> FEATURE:
<223> OTHER INFORMATION: CDR3 Nb125

<400> SEQUENCE: 54

Asp Pro Gln Arg Cys Gly Ser Trp Thr Trp Ala Asn Met Tyr Glu Tyr
1               5                   10                  15
Asn Tyr

<210> SEQ ID NO 55
<211> LENGTH: 5
<212> TYPE: PRT
<213> ORGANISM: artificial sequence
<220> FEATURE:
<223> OTHER INFORMATION: CDR1 Nb155

<400> SEQUENCE: 55

Asp Tyr Ile Met Asn
1               5

<210> SEQ ID NO 56
<211> LENGTH: 17
<212> TYPE: PRT
<213> ORGANISM: artificial sequence
<220> FEATURE:
<223> OTHER INFORMATION: CDR2 Nb155

<400> SEQUENCE: 56

Met Ile Ile Gln Asn Gly Gly Asp Thr His Tyr Ala Asp Ser Val Lys
1               5                   10                  15
Gly

<210> SEQ ID NO 57
<211> LENGTH: 16
<212> TYPE: PRT
<213> ORGANISM: artificial sequence
<220> FEATURE:
<223> OTHER INFORMATION: CDR3 Nb155
```

```
<400> SEQUENCE: 57

Gly Ala Leu Leu Pro Thr Phe Asn His Cys Pro Pro Gly Ala Tyr
1               5                   10                  15

<210> SEQ ID NO 58
<211> LENGTH: 5
<212> TYPE: PRT
<213> ORGANISM: artificial sequence
<220> FEATURE:
<223> OTHER INFORMATION: CDR1 Nb37

<400> SEQUENCE: 58

Ser Tyr Cys Met Gly
1               5

<210> SEQ ID NO 59
<211> LENGTH: 17
<212> TYPE: PRT
<213> ORGANISM: artificial sequence
<220> FEATURE:
<223> OTHER INFORMATION: CDR2 Nb37

<400> SEQUENCE: 59

His Ile Ser Thr Asn Asn Ile Ser Pro Ala Tyr Asn Lys Phe Arg Glu
1               5                   10                  15

Gly

<210> SEQ ID NO 60
<211> LENGTH: 17
<212> TYPE: PRT
<213> ORGANISM: artificial sequence
<220> FEATURE:
<223> OTHER INFORMATION: CDR3 Nb37

<400> SEQUENCE: 60

Arg Thr Gly Tyr Cys Ser Gly Ser Trp Gly Val Ala Asp Ser Phe Asn
1               5                   10                  15

Gly

<210> SEQ ID NO 61
<211> LENGTH: 5
<212> TYPE: PRT
<213> ORGANISM: artificial sequence
<220> FEATURE:
<223> OTHER INFORMATION: CDR1 Nb77

<400> SEQUENCE: 61

Ser Tyr Cys Met Gly
1               5

<210> SEQ ID NO 62
<211> LENGTH: 17
<212> TYPE: PRT
<213> ORGANISM: artificial sequence
<220> FEATURE:
<223> OTHER INFORMATION: CDR2 Nb77

<400> SEQUENCE: 62

His Ile Ser Thr Gly Val Ile Ser Pro Gly Tyr Asn Lys Phe Ala Glu
1               5                   10                  15

Gly

<210> SEQ ID NO 63
```

```
<211> LENGTH: 17
<212> TYPE: PRT
<213> ORGANISM: artificial sequence
<220> FEATURE:
<223> OTHER INFORMATION: CDR3 Nb77

<400> SEQUENCE: 63

Arg Thr Gly Ser Cys Ser Gly Ser Trp Gly Val Ala Asp Ser Phe Asn
1               5                   10                  15

Gly

<210> SEQ ID NO 64
<211> LENGTH: 5
<212> TYPE: PRT
<213> ORGANISM: artificial sequence
<220> FEATURE:
<223> OTHER INFORMATION: CDR1 Nb171

<400> SEQUENCE: 64

Ser Tyr Cys Met Gly
1               5

<210> SEQ ID NO 65
<211> LENGTH: 17
<212> TYPE: PRT
<213> ORGANISM: artificial sequence
<220> FEATURE:
<223> OTHER INFORMATION: CDR2 Nb 171

<400> SEQUENCE: 65

Arg Ile Ser Thr Gly Val Ile Ser Pro Gly Tyr Asn Lys Phe Ala Glu
1               5                   10                  15

Gly

<210> SEQ ID NO 66
<211> LENGTH: 17
<212> TYPE: PRT
<213> ORGANISM: artificial sequence
<220> FEATURE:
<223> OTHER INFORMATION: CDR3 Nb171

<400> SEQUENCE: 66

Arg Thr Gly Ser Cys Ser Gly Ser Trp Gly Val Ala Asp Ser Phe Asn
1               5                   10                  15

Gly

<210> SEQ ID NO 67
<211> LENGTH: 5
<212> TYPE: PRT
<213> ORGANISM: artificial sequence
<220> FEATURE:
<223> OTHER INFORMATION: CDR1 Nb159

<400> SEQUENCE: 67

Met Tyr Cys Met Ala
1               5

<210> SEQ ID NO 68
<211> LENGTH: 17
<212> TYPE: PRT
<213> ORGANISM: artificial sequence
<220> FEATURE:
<223> OTHER INFORMATION: CDR2 Nb159
```

```
<400> SEQUENCE: 68

Ala Ile Asn Ser Gly Gly Pro Ser Thr Tyr Tyr Ala Asp Ser Val Lys
1               5                   10                  15

Gly

<210> SEQ ID NO 69
<211> LENGTH: 18
<212> TYPE: PRT
<213> ORGANISM: artificial sequence
<220> FEATURE:
<223> OTHER INFORMATION: CDR3 Nb159

<400> SEQUENCE: 69

Asp Pro Gln Arg Cys Gly Ser Trp Ser Trp Ala Asn Met Tyr Glu Tyr
1               5                   10                  15

Asn Tyr

<210> SEQ ID NO 70
<211> LENGTH: 5
<212> TYPE: PRT
<213> ORGANISM: artificial sequence
<220> FEATURE:
<223> OTHER INFORMATION: CDR1 Nbp25

<400> SEQUENCE: 70

Met Tyr Cys Met Gly
1               5

<210> SEQ ID NO 71
<211> LENGTH: 17
<212> TYPE: PRT
<213> ORGANISM: artificial sequence
<220> FEATURE:
<223> OTHER INFORMATION: CDR2 Nbp25

<400> SEQUENCE: 71

Ala Ile Asn Ser Gly Asn Gly Asn Thr Tyr Tyr Ala Asp Ser Val Lys
1               5                   10                  15

Gly

<210> SEQ ID NO 72
<211> LENGTH: 18
<212> TYPE: PRT
<213> ORGANISM: artificial sequence
<220> FEATURE:
<223> OTHER INFORMATION: CDR3 NBp25

<400> SEQUENCE: 72

Asp Pro Gln Arg Cys Gly Ser Trp Thr Trp Ala Gly Val Phe Glu Tyr
1               5                   10                  15

Asn Tyr

<210> SEQ ID NO 73
<211> LENGTH: 5
<212> TYPE: PRT
<213> ORGANISM: artificial sequence
<220> FEATURE:
<223> OTHER INFORMATION: CDR1 Nb172

<400> SEQUENCE: 73

Asp Tyr Phe Met Asn
1               5
```

<210> SEQ ID NO 74
<211> LENGTH: 17
<212> TYPE: PRT
<213> ORGANISM: artificial sequence
<220> FEATURE:
<223> OTHER INFORMATION: CDR2 Nb172

<400> SEQUENCE: 74

Met Ile Ser Met Asn Gly Ala Asp Thr His Tyr Ala Asp Ser Val Lys
1               5                   10                  15

Gly

<210> SEQ ID NO 75
<211> LENGTH: 16
<212> TYPE: PRT
<213> ORGANISM: artificial sequence
<220> FEATURE:
<223> OTHER INFORMATION: CDR3 Nb172

<400> SEQUENCE: 75

Gly Ala Leu Leu Pro Ser Tyr Asn His Cys Pro Pro Pro Gly Ala Tyr
1               5                   10                  15

<210> SEQ ID NO 76
<211> LENGTH: 5
<212> TYPE: PRT
<213> ORGANISM: artificial sequence
<220> FEATURE:
<223> OTHER INFORMATION: CDR1 Nb122

<400> SEQUENCE: 76

Ser Tyr Ala Met Ala
1               5

<210> SEQ ID NO 77
<211> LENGTH: 21
<212> TYPE: PRT
<213> ORGANISM: artificial sequence
<220> FEATURE:
<223> OTHER INFORMATION: CDR2 Nb122

<400> SEQUENCE: 77

Ala Tyr Tyr Arg Gly Phe Gly Gly Ala Gln His Ser Thr His Tyr Ala
1               5                   10                  15

Ala Ser Val Thr Gly
            20

<210> SEQ ID NO 78
<211> LENGTH: 16
<212> TYPE: PRT
<213> ORGANISM: artificial sequence
<220> FEATURE:
<223> OTHER INFORMATION: CDR3 Nb122

<400> SEQUENCE: 78

Ser Thr Ala Asp Asp Asp Asp Trp His Ser Leu Arg Arg Tyr Asn Tyr
1               5                   10                  15

<210> SEQ ID NO 79
<211> LENGTH: 5
<212> TYPE: PRT
<213> ORGANISM: artificial sequence
<220> FEATURE:
<223> OTHER INFORMATION: CDR1 Nb15

```
<400> SEQUENCE: 79

Pro Tyr Cys Met Gly
1               5

<210> SEQ ID NO 80
<211> LENGTH: 17
<212> TYPE: PRT
<213> ORGANISM: artificial sequence
<220> FEATURE:
<223> OTHER INFORMATION: CDR2 Nb15

<400> SEQUENCE: 80

Thr Ile Thr Arg Ser Gly Asp Arg Thr Tyr Tyr Ala Asp Ala Val Lys
1               5                   10                  15

Gly

<210> SEQ ID NO 81
<211> LENGTH: 20
<212> TYPE: PRT
<213> ORGANISM: artificial sequence
<220> FEATURE:
<223> OTHER INFORMATION: CDR3 Nb15

<400> SEQUENCE: 81

Ser Phe Asn Tyr Leu Pro Thr Tyr Leu Thr Cys Gly Ser Arg Thr Ala
1               5                   10                  15

Glu Tyr Asn Phe
            20

<210> SEQ ID NO 82
<211> LENGTH: 5
<212> TYPE: PRT
<213> ORGANISM: artificial sequence
<220> FEATURE:
<223> OTHER INFORMATION: CDR1 Nbp77

<400> SEQUENCE: 82

Pro Tyr Cys Met Gly
1               5

<210> SEQ ID NO 83
<211> LENGTH: 17
<212> TYPE: PRT
<213> ORGANISM: artificial sequence
<220> FEATURE:
<223> OTHER INFORMATION: CDR2 Nbp77

<400> SEQUENCE: 83

Thr Ile Thr Arg Ser Gly Asp Arg Thr Ser Tyr Ala Asp Ala Val Lys
1               5                   10                  15

Gly

<210> SEQ ID NO 84
<211> LENGTH: 20
<212> TYPE: PRT
<213> ORGANISM: artificial sequence
<220> FEATURE:
<223> OTHER INFORMATION: CDR3 Nbp77
```

```
<400> SEQUENCE: 84

Ser Phe Asn Tyr Arg Pro Thr Tyr Val Thr Cys Asn Ser Arg Thr Ala
1               5                   10                  15

Glu Tyr Asn Phe
            20

<210> SEQ ID NO 85
<211> LENGTH: 5
<212> TYPE: PRT
<213> ORGANISM: artificial sequence
<220> FEATURE:
<223> OTHER INFORMATION: CDR1 Nb34

<400> SEQUENCE: 85

Ser Tyr Cys Met Gly
1               5

<210> SEQ ID NO 86
<211> LENGTH: 17
<212> TYPE: PRT
<213> ORGANISM: artificial sequence
<220> FEATURE:
<223> OTHER INFORMATION: CDR2 Nb34

<400> SEQUENCE: 86

Thr Ile Asp Ser Gly Ser Gly Arg Thr Tyr Tyr Ala Asp Ser Val Lys
1               5                   10                  15

Gly

<210> SEQ ID NO 87
<211> LENGTH: 26
<212> TYPE: PRT
<213> ORGANISM: artificial sequence
<220> FEATURE:
<223> OTHER INFORMATION: CDR3 Nb34

<400> SEQUENCE: 87

Val Gly Ala Asn Ser Gly Gly Leu Trp Ser Ser Cys Gly Tyr Cys Tyr
1               5                   10                  15

Gly Gly Leu Cys Gly Asp Asp Phe Gly Tyr
            20                  25

<210> SEQ ID NO 88
<211> LENGTH: 5
<212> TYPE: PRT
<213> ORGANISM: artificial sequence
<220> FEATURE:
<223> OTHER INFORMATION: CDR1 Nb80

<400> SEQUENCE: 88

Ser Tyr Cys Met Gly
1               5

<210> SEQ ID NO 89
<211> LENGTH: 17
<212> TYPE: PRT
<213> ORGANISM: artificial sequence
<220> FEATURE:
<223> OTHER INFORMATION: CDR2 Nb80
```

```
<400> SEQUENCE: 89

Thr Ile Asp Ser Gly Ser Gly Arg Thr Tyr Tyr Ala Asp Ser Val Lys
1               5                   10                  15

Gly

<210> SEQ ID NO 90
<211> LENGTH: 26
<212> TYPE: PRT
<213> ORGANISM: artificial sequence
<220> FEATURE:
<223> OTHER INFORMATION: CDR3 Nb80

<400> SEQUENCE: 90

Val Gly Ala Asn Ser Gly Gly Leu Trp Ser Ser Cys Gly Tyr Cys Tyr
1               5                   10                  15

Gly Gly Leu Cys Glu Asp Asp Phe Gly Tyr
            20                  25

<210> SEQ ID NO 91
<211> LENGTH: 5
<212> TYPE: PRT
<213> ORGANISM: artificial sequence
<220> FEATURE:
<223> OTHER INFORMATION: CDR1 Nb38

<400> SEQUENCE: 91

Ile Asn Leu Met Gly
1               5

<210> SEQ ID NO 92
<211> LENGTH: 18
<212> TYPE: PRT
<213> ORGANISM: artificial sequence
<220> FEATURE:
<223> OTHER INFORMATION: CDR2 Nb38

<400> SEQUENCE: 92

Thr Ile Tyr Thr Val Gly Ser Ser Ser Thr Tyr Tyr Ala Asp Ser Val
1               5                   10                  15

Lys Gly

<210> SEQ ID NO 93
<211> LENGTH: 12
<212> TYPE: PRT
<213> ORGANISM: artificial sequence
<220> FEATURE:
<223> OTHER INFORMATION: CDR3 Nb38

<400> SEQUENCE: 93

Gly Val Gly Trp Leu Ser Asn Ser Glu Tyr Asn Tyr
1               5                   10

<210> SEQ ID NO 94
<211> LENGTH: 5
<212> TYPE: PRT
<213> ORGANISM: artificial sequence
<220> FEATURE:
<223> OTHER INFORMATION: CDR1 Nb137

<400> SEQUENCE: 94

Gln Cys Gly Met Gly
1               5
```

```
<210> SEQ ID NO 95
<211> LENGTH: 16
<212> TYPE: PRT
<213> ORGANISM: artificial sequence
<220> FEATURE:
<223> OTHER INFORMATION: CDR2 Nb137

<400> SEQUENCE: 95

Thr Ile Ser Ser Asp Gly Ser Thr Thr Tyr Ala Asp Ser Ile Lys Gly
1               5                   10                  15

<210> SEQ ID NO 96
<211> LENGTH: 12
<212> TYPE: PRT
<213> ORGANISM: artificial sequence
<220> FEATURE:
<223> OTHER INFORMATION: CDR3 Nb137

<400> SEQUENCE: 96

Asp Pro Leu Gly Asn Ser Cys Pro Gly Leu Ser Tyr
1               5                   10

<210> SEQ ID NO 97
<211> LENGTH: 5
<212> TYPE: PRT
<213> ORGANISM: artificial sequence
<220> FEATURE:
<223> OTHER INFORMATION: CDR1 Nb139

<400> SEQUENCE: 97

Arg Asn Cys Met Gly
1               5

<210> SEQ ID NO 98
<211> LENGTH: 17
<212> TYPE: PRT
<213> ORGANISM: artificial sequence
<220> FEATURE:
<223> OTHER INFORMATION: CDR2 Nb139

<400> SEQUENCE: 98

Ala Ile Tyr Thr Gly Ser Gly Asn Thr Asn Tyr Ala Asp Ser Val Lys
1               5                   10                  15
Gly

<210> SEQ ID NO 99
<211> LENGTH: 19
<212> TYPE: PRT
<213> ORGANISM: artificial sequence
<220> FEATURE:
<223> OTHER INFORMATION: CDR3 Nb139

<400> SEQUENCE: 99

Arg Asn Ser Gly Ser Trp Trp Arg Pro Ser Cys Asn Phe Asp Ser Asp
1               5                   10                  15
Phe Gly Tyr

<210> SEQ ID NO 100
<211> LENGTH: 5
<212> TYPE: PRT
<213> ORGANISM: artificial sequence
<220> FEATURE:
<223> OTHER INFORMATION: CDR1 Nbp12
```

<400> SEQUENCE: 100

Ser Phe Cys Met Gly
1               5

<210> SEQ ID NO 101
<211> LENGTH: 17
<212> TYPE: PRT
<213> ORGANISM: artificial sequence
<220> FEATURE:
<223> OTHER INFORMATION: CDR2 Nbp12

<400> SEQUENCE: 101

Val Ile Gln Pro Gly Arg Asn Ser Lys Asp Tyr Ala Asp Ser Val Lys
1               5                   10                  15

Gly

<210> SEQ ID NO 102
<211> LENGTH: 19
<212> TYPE: PRT
<213> ORGANISM: artificial sequence
<220> FEATURE:
<223> OTHER INFORMATION: CDR3 Nbp12

<400> SEQUENCE: 102

Thr Gly Leu Trp Ile Ser Ser Gly Ser Cys Gln Thr Ile Pro Asp Gln
1               5                   10                  15

Tyr Ser Tyr

<210> SEQ ID NO 103
<211> LENGTH: 30
<212> TYPE: PRT
<213> ORGANISM: artificial sequence
<220> FEATURE:
<223> OTHER INFORMATION: FR1
<220> FEATURE:
<221> NAME/KEY: MISC_FEATURE
<222> LOCATION: (11)..(11)
<223> OTHER INFORMATION: Xaa is a serine or an alanine residue
<220> FEATURE:
<221> NAME/KEY: MISC_FEATURE
<222> LOCATION: (14)..(14)
<223> OTHER INFORMATION: Xaa is a valine, a proline or an alanine
      residue
<220> FEATURE:
<221> NAME/KEY: MISC_FEATURE
<222> LOCATION: (19)..(19)
<223> OTHER INFORMATION: Xaa is an arginine or a lysine residue
<220> FEATURE:
<221> NAME/KEY: MISC_FEATURE
<222> LOCATION: (20)..(20)
<223> OTHER INFORMATION: Xaa is a valine or a leucine residue
<220> FEATURE:
<221> NAME/KEY: MISC_FEATURE
<222> LOCATION: (21)..(21)
<223> OTHER INFORMATION: Xaa is an alanine or a serine residue
<220> FEATURE:
<221> NAME/KEY: MISC_FEATURE
<222> LOCATION: (23)..(23)
<223> OTHER INFORMATION: Xaa is an alanine, a glutamate or a valine
      residue
<220> FEATURE:
<221> NAME/KEY: MISC_FEATURE
<222> LOCATION: (26)..(26)
<223> OTHER INFORMATION: Xaa is a glycine, a glutamate or a threonine
<220> FEATURE:
<221> NAME/KEY: MISC_FEATURE
<222> LOCATION: (27)..(27)
<223> OTHER INFORMATION: Xaa is an aspartate, a tyrosine, a leucine or
      an isoleucine
<220> FEATURE:

```
<221> NAME/KEY: misc_feature
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa is a phenylalanine, a proline, a serine, a
      tyrosine, a leucine, a histidine, an alanine or a threonine
<220> FEATURE:
<221> NAME/KEY: MISC_FEATURE
<222> LOCATION: (30)..(30)
<223> OTHER INFORMATION: Xaa is a serine, a glutamate, an asparagine, or
      an arginine

<400> SEQUENCE: 103

Gln Val Gln Leu Gln Glu Ser Gly Gly Gly Xaa Val Gln Xaa Gly Gly
1               5                   10                  15

Ser Leu Xaa Xaa Xaa Cys Xaa Ala Ser Xaa Xaa Xaa Xaa Xaa
            20                  25                  30

<210> SEQ ID NO 104
<211> LENGTH: 14
<212> TYPE: PRT
<213> ORGANISM: artificial sequence
<220> FEATURE:
<223> OTHER INFORMATION: FR2
<220> FEATURE:
<221> NAME/KEY: MISC_FEATURE
<222> LOCATION: (9)..(9)
<223> OTHER INFORMATION: Xaa is a glycine or a glutamate residue

<400> SEQUENCE: 104

Trp Phe Arg Gln Ala Pro Gly Lys Xaa Arg Glu Gly Val Ala
1               5                   10

<210> SEQ ID NO 105
<211> LENGTH: 32
<212> TYPE: PRT
<213> ORGANISM: artificial sequence
<220> FEATURE:
<223> OTHER INFORMATION: FR3
<220> FEATURE:
<221> NAME/KEY: MISC_FEATURE
<222> LOCATION: (12)..(12)
<223> OTHER INFORMATION: Xaa is a isoleucine or a methionine residue
<220> FEATURE:
<221> NAME/KEY: MISC_FEATURE
<222> LOCATION: (19)..(19)
<223> OTHER INFORMATION: Xaa is a serine or a glycine residue

<400> SEQUENCE: 105

Arg Phe Thr Ile Ser Lys Asp Asn Ala Asp Asn Xaa Met Tyr Leu Glu
1               5                   10                  15

Met Asn Xaa Leu Lys Pro Glu Asp Thr Ala Ile Tyr Tyr Cys Ala Ala
            20                  25                  30

<210> SEQ ID NO 106
<211> LENGTH: 11
<212> TYPE: PRT
<213> ORGANISM: artificial sequence
<220> FEATURE:
<223> OTHER INFORMATION: FR4

<400> SEQUENCE: 106

Trp Gly Gln Gly Thr Gln Val Thr Val Ser Ser
1               5                   10
```